(12) United States Patent
Herrema

(10) Patent No.: US 12,385,073 B2
(45) Date of Patent: *Aug. 12, 2025

(54) POLYHYDROXYALKANOATE PRODUCTION METHODS AND MATERIALS AND MICROORGANISMS USED IN SAME

(71) Applicant: Newlight Technologies, Inc., Huntington Beach, CA (US)

(72) Inventor: Markus D. Herrema, Venice, CA (US)

(73) Assignee: NEWLIGHT TECHNOLOGIES, INC., Huntington Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/609,707

(22) Filed: Mar. 19, 2024

(65) Prior Publication Data

US 2025/0043322 A1    Feb. 6, 2025

Related U.S. Application Data

(63) Continuation of application No. 17/365,351, filed on Jul. 1, 2021, now Pat. No. 11,965,203, which is a continuation of application No. 16/577,373, filed on Sep. 20, 2019, now Pat. No. 11,053,521, which is a continuation of application No. 15/643,905, filed on Jul. 7, 2017, now Pat. No. 10,450,592, which is a continuation of application No. 14/740,056, filed on Jun. 15, 2015, now Pat. No. 9,725,744, which is a continuation of application No. 13/802,622, filed on Mar. 13, 2013, now Pat. No. 9,085,784.

(60) Provisional application No. 61/617,534, filed on Mar. 29, 2012.

(51) Int. Cl.
  *C12P 7/625* (2022.01)

(52) U.S. Cl.
  CPC .................................. *C12P 7/625* (2013.01)

(58) Field of Classification Search
  CPC .................................. C12P 7/62; C12P 7/625
  See application file for complete search history.

(56) References Cited

U.S. PATENT DOCUMENTS

| | | | | |
|---|---|---|---|---|
| 9,040,267 | B2 * | 5/2015 | Herrema | C12P 7/625 |
| | | | | 435/135 |
| 9,085,784 | B1 * | 7/2015 | Herrema | C12P 7/625 |
| 9,725,744 | B2 * | 8/2017 | Herrema | C12P 7/625 |
| 10,450,592 | B2 * | 10/2019 | Herrema | C12P 7/625 |
| 11,053,521 | B2 * | 7/2021 | Herrema | C12P 7/625 |
| 11,965,203 | B2 * | 4/2024 | Herrema | C12P 7/625 |

* cited by examiner

*Primary Examiner* — Tekchand Saidha
(74) *Attorney, Agent, or Firm* — Snell & Wilmer LLP

(57) ABSTRACT

Embodiments of the invention relate generally to methods to generate microorganisms and/or microorganism cultures that exhibit the ability to produce polyhydroxyalkanoates (PHA) from carbon sources at high efficiencies. In several embodiments, preferential expression of, or preferential growth of microorganisms utilizing certain metabolic pathways, enables the high efficiency PHA production from carbon-containing gases or materials. Several embodiments relate to the microorganism cultures, and/or microorganisms isolated therefrom.

20 Claims, 1 Drawing Sheet

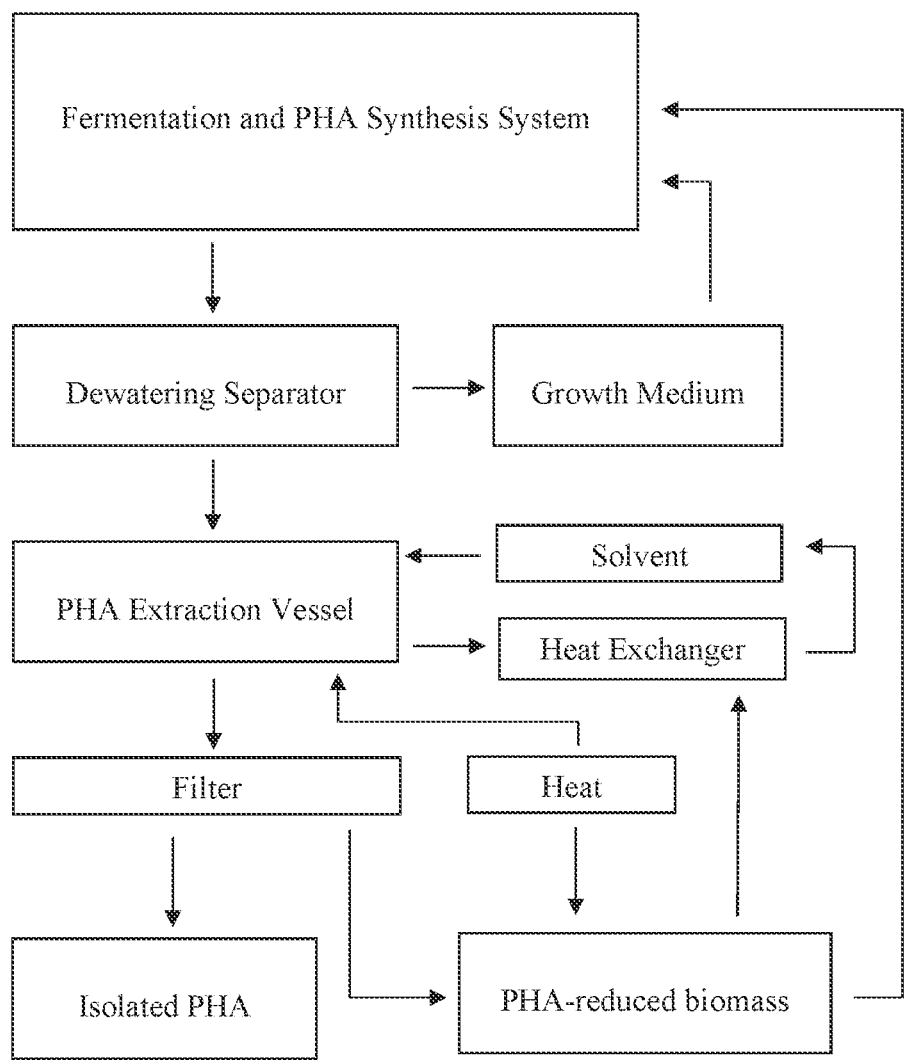

POLYHYDROXYALKANOATE PRODUCTION METHODS AND MATERIALS AND MICROORGANISMS USED IN SAME

RELATED CASES

This application is a continuation of U.S. patent application Ser. No. 17/365,351, filed Jul. 1, 2021, which is a continuation of U.S. patent application Ser. No. 16/577,373, filed Sep. 20, 2019 (now issued as U.S. Pat. No. 11,053,521), which is a continuation of U.S. patent application Ser. No. 15/643,905, filed Jul. 7, 2017, (now issued as U.S. Pat. No. 10,450,592), which is a continuation of U.S. patent application Ser. No. 14/740,056, filed Jun. 15, 2015 (now issued as U.S. Pat. No. 9,725,744), which is a continuation of U.S. patent application Ser. No. 13/802,622, filed Mar. 13, 2013 (now issued as U.S. Pat. No. 9,085,784), which claims the benefit of U.S. Provisional Application No. 61/617,534, filed on Mar. 29, 2012 the entire disclosure of each of which is incorporated in its entirety by reference herein.

BACKGROUND

Field of the Invention

Embodiments of the invention relate to an improved process for the production, processing, and functional modification of polyhydroxyalkanoates (PHAs), and specifically to processes for the production, processing, and functional modification of PHAs, wherein those PHAs may be made from carbon-containing gases and materials.

Description of the Related Art

Polyhydroxyalkanoates (PHAs) are thermoplastic polyesters that serve as carbon and energy storage vehicles in microorganisms. PHAs are naturally biodegradable in both aerobic and anaerobic conditions, are biocompatible with mammalian tissues, and, as thermoplastics, can be used as alternatives to fossil fuel-based synthetic plastics such as polypropylene, polyethylene, and polystyrene. In comparison to traditional petrochemical-based plastics, which are neither biodegradable nor made from sustainable sources of carbon, PHA plastics afford significant environmental benefits.

The utilization of food crop derived sugars in genetically engineered microorganism-based aqueous fermentation systems is often regarded as the most efficient and economical platform for PHA production. Specifically, sugar-based PHA production processes are capable of generating high density fermentation cultures and high PHA inclusion concentrations, and, by maximizing the cell culture density and PHA inclusion concentration therein, it is believed that carbon, chemical, and energy efficiencies are also maximized. For example, comparing a low cell and PHA concentration process to a high cell and PHA concentration process, a low concentration process requires significantly more, per given unit of PHA-containing biomass, i) energy for dewatering cells prior to PHA extraction treatment, ii) liquid culture volume, and associated chemicals, mixing energy, and heat removal energy, and iii) both energy and chemicals for separating PHA from biomass. Accordingly, whereas the sugar-based genetically-engineered microorganism PHA process yields maximized cell densities and PHA concentrations relative to low concentration processes, it is also regarded as the most carbon, chemical, energy, and, thus, cost efficient PHA production method.

Unfortunately, despite these maximized efficiency advantages, sugar-based PHA production remains more expensive than fossil fuel-based plastics production. Thus, given the apparent efficiency maximization of the high density sugar-derived PHA production process, PHAs are generally considered to be unable to compete with fossil fuel-based plastics on energy, chemical, and cost efficiency.

SUMMARY

Despite the environmental advantages of PHAs, the high cost of PHA production relative to the low cost of fossil fuel-based plastics production has significantly limited the industrial production and commercial adoption of PHAs.

To reduce the carbon input cost of the PHA production process, carbon-containing industrial off-gases, such as carbon dioxide, methane, and volatile organic compounds, have been proposed as an alternative to food crop-based and plant-based sources of carbon. In addition to the wide availability and low cost of carbon-containing gases, carbon-containing gases also do not present the environmental challenges associated with food crop and plant-derived sources of carbon. Specifically, whereas food crop- and plant-based carbon substrates require land, fertilizers, pesticides, and fossil fuels to produce, and also generate greenhouse gas emissions during the course of production, carbon-containing off-gases do not require new inputs of land, fertilizers, or pesticides to generate. Thus, on both an economic and environmental basis, the utilization of carbon emissions for the production of PHA would appear to offer significant advantages over sugar-based PHA production processes.

Unfortunately, the fermentation or biotechnological conversion of carbon-containing gases into PHAs presents technical challenges and stoichiometric limitations that have, in the past, rendered the gas-to-PHA production process significantly more energy and chemical intensive, and thus more costly, than the food crop-based PHA production process. These technical challenges and stoichiometric limitations include, but are not limited to low mass transfer rates, low microorganism growth rates, extended polymerization times, low cell densities, high oxygen demand, low PHA cellular inclusion concentrations, low polymer production per unit of biocatalyst production, low biocatalyst yield per unit gas input, poor polymer functionality, and/or high downstream functionalization costs. Whereas sugar-based fermentation or bioconversion systems have the ability to generate high cellular densities and PHA inclusion concentrations, based on cell morphology and mass transfer constraints, carbon-containing gas-based fermentation or bioconversion processes typically generate 10-70% of the biomass and intracellular PHA inclusion concentrations achieved in sugar-based processes. As a result, the ratio of energy-to-PHA required to carry out upstream carbon mass transfer, oxygen mass transfer, and culture mixing, as well as downstream PHA processing and/or purification, significantly exceeds the energy-to-PHA ratio required for sugar-based PHA production methods, thereby rendering the emissions-based process uncompetitive when compared to both petroleum-based plastics and sugar-based PHAs.

In light of the potential environmental advantages and carbon cost efficiencies of utilizing carbon-containing gases as a source of carbon for PHA production, there exists a significant need to reduce the energy, chemical, and carbon input-to-PHA output ratio in a carbon emissions-based PHA production system, and thereby render carbon gas-derived PHA economically competitive with petrochemical-based plastics.

Thus, in several embodiments, there is provided a methanotrophic microorganism (or a culture of such microorganisms) that are capable of generating PHA, particularly at high efficiency levels, thereby resulting in increased PHA production yield (e.g., high PHA concentrations per unit mass of microorganism or unit weight of culture).

In several embodiments, there is provided a methanotrophic microorganism characterized by a lack of the genetic material encoding soluble methane monooxygenase (sMMO), presence of genetic material encoding the ethylmalonyl-CoA pathway, transcription of DNA encoding the ethylmalonyl-CoA pathway, and translation of mRNA encoding the ethylmalonyl-CoA pathway and, the capability of producing polyhydroxyalkanoate (PHA).

In several embodiments, the methanotrophic microorganism possesses genetic material encoding the sMMO enzyme, but fails to either transcribe DNA encoding sMMO or translate mRNA encoding sMMO, and/or fails to produce a functional sMMO enzyme.

In several embodiments, the methanotrophic microorganism is from a genus selected from a group consisting of: *Methylosinus, Methylocystis, Methylococcus, Methylobacterium*, and *Pseudomonas*. In several embodiments, the methanotrophic microorganism is derived from a methanotrophic microorganism of one of such genera.

In several embodiments, the methanotrophic microorganism exhibits particulate methane monooxygenase activity in the presence of copper ion concentrations between 0.001 micromolar and 1000 micromolar, while in some embodiments the methanotrophic microorganism exhibits ethylmalonyl-CoA pathway activity in the presence of copper concentrations between 0.001 micromolar and 1000 micromolar. In several embodiments, both particulate methane monooxygenase activity and ethylmalonyl-CoA pathway activity are exhibited in the same or similar conditions. In several embodiments, the methanotrophic microorganism exhibits little or no soluble methane monooxygenase activity under the same or similar conditions.

In several embodiments, the methanotrophic microorganism obtains the recited characteristics due to one or more of mutation, genetically-engineered mutation, and/or selection-pressure-induced mutation. Selection-pressure-induced mutation, as used herein, shall be given its ordinary meaning and shall also refer to conditions in which the methanotrophic microorganism is cultured that favor one or more microorganisms having certain characteristics. Depending on the embodiments, this may be, for example, ability to upregulate or utilize a particular biochemical or metabolic pathway in response to one or more variables in the culture environment (e.g., nutrients, population density, pH, temperature, salinity, etc.). In several embodiments, the selection-pressure-induced mutation shall also refer to conditions that exploit certain competitive advantages possessed by certain methanotrophic microorganisms and not by others (or possessed or exploited to a lesser extent).

In several embodiments, the methanotrophic microorganism is capable of producing PHA at intracellular PHA concentrations with a ratio of PHA to non-PHA biomass exceeding 3:1 on a dry weight basis. In several embodiments, the methanotrophic microorganism are capable of producing PHA at a concentration (based on dry weight of a microbial culture of the methanotrophic microorganisms of at least about 51%. In several embodiments, the PHA is produced at least about 71%, or at least about 81% of the total dry cell weight of the methanotrophic microorganisms.

In several embodiments, there is provided an isolated or purified culture of microorganisms having the characteristics described herein.

In several embodiments, there is also provided a method for enhanced PHA production by a culture of methanotrophic microorganisms, comprising, (a) providing a culture medium comprising methane, copper, and at least one additional nutrient, (b) providing a culture comprising methanotrophic microorganisms, (c) culturing the methanotrophic microorganisms in the culture medium, (d) controlling the concentration of copper in the medium to result in a copper concentration suitable for methanotrophic microorganisms to produce soluble methane monooxygenase (sMMO), (e) reducing, for a first period of time, the concentration of the at least one additional nutrient in the medium to cause the methanotrophic microorganisms to produce PHA, (f) increasing, for a second period of time, the concentration of the at least one additional nutrient of step (e) to cause the methanotrophic microorganisms to reproduce using essentially only particulate methane monooxygenase (pMMO), and (g) subjecting the culture of methanotrophic microorganisms to at least two repetitions of steps (d), (e), and (f). In several embodiments, the at least two repetitions result in the culture of methanotrophic microorganisms producing PHA at concentrations exceeding those produced absent the at least two repetitions.

In several embodiments, the culturing is performed under non-sterile conditions, though PHA production can also be performed, optionally, in sterile or semi-sterile conditions.

In several embodiments, PHA is produced at concentrations are at least about 51% of total dry cell weight of the methanotrophic microorganisms. In several embodiments the PHA produced is at least about 71% of the total dry cell weight of the methanotrophic microorganisms, while in still additional embodiments, the PHA produced is at least about 81% of total dry cell weight of the methanotrophic microorganisms In several embodiments, the copper concentration is controlled (e.g., increased, decreased, held etc.) to be between about 0.001 micromolar and about 1000 micromolar.

In several embodiments, the first period of time ranges from about 2 to 24 hours, including about 2 to about 6, about 6 to about 10, about 10 to about 14, about 14 to about 16, about 16 to about 20, about 20 to about 24 hours, and overlapping ranges thereof. In several embodiments, the second period of time ranges from about 12 to 24 hours, including about 12 to about 16, about 16 to about 20, about 20 to about 24, and overlapping ranges thereof. Longer or shorter time periods may be used for the first period of time, the second period of time, and/or for both the first and the second period of time, depending on the embodiment.

In several embodiments, the additional nutrient comprises at least one of the nutrients selected from the group consisting of aluminum, boron, calcium, carbon, carbon dioxide, cobalt, iron, magnesium, molybdenum, nitrogen, oxygen, phosphorus, potassium, sodium, and zinc. In one embodiment, the at least one additional nutrient comprises dissolved oxygen and the method further comprises increasing the concentration of dissolved oxygen in the culture media to preferentially select for methanotrophic microorganisms exhibiting reduced pigmentation.

In several embodiments, the at least two repetitions induce most or substantially all of the methanotrophic microorganisms to express pMMO and fail to express sMMO, contain the genetic material for sMMO, and/or produce a functional sMMO.

Additionally, in several embodiments, the present invention relates to novel processes for the conversion of carbon-containing gases into PHAs at previously unattainable energy and carbon PHA conversion ratios. Moreover, there are provided herein, systems, methods and materials for the production and processing of PHA that provide environmental advantages and carbon cost efficiencies (by utilizing carbon-containing gases as a source of carbon for PHA production). Several embodiments also reduce one or more of the energy, chemical, and carbon input-to-PHA output ratio for producing carbon emissions-based PHA. As such, in several embodiments, the systems, methods and materials disclosed herein render carbon gas-derived PHA economically competitive with petrochemical-based plastics.

In some embodiments, the invention also relates to a process that generates a carbon emissions-based PHA material that is cost-competitive with both food crop-based PHAs and fossil fuel-based thermoplastics.

While PHAs are widely considered to be noncompetitive with fossil fuel-based plastics on energy, chemical, and cost efficiency, several embodiments of the invention relate to a process for producing PHAs from carbon-containing gases that yields unexpectedly improved energy, carbon, chemical, and cost efficiencies over sugar-based PHA production methodologies.

Applicant has advantageously discovered that certain culturing or bioprocessing techniques disclosed herein are suitable for production of PHAs by methanotrophic, heterotrophic, and/or autotrophic microorganisms at efficiencies (e.g., intracellular PHA concentrations, PHA:non-PHA biomass ratios, or PHA:biocatalyst ratios) that previously were not considered achievable. In some embodiments, the techniques relate to the manipulation of the culture or biocatalyst operating environment (e.g., alteration of one or more of constituents of the culture or nutrient media, for example the increase, reduction, or elimination of a certain nutrient (or nutrients), alterations in carbon sources, alterations of times or temperatures that certain metabolic activities are underway, and the like).

As a result of such methods, there is provided herein, in several embodiments, a culture of methanotrophic microorganisms that (a) does not express or contain the genetic material encoding soluble methane monooxygenase, (b) expresses or contains the genetic material encoding the ethylmalonyl-CoA pathway, and (c) produces polyhydroxyalkanoate (PHA) at intracellular concentrations wherein the ratio of PHA to non-PHA biomass exceeds about 2:1, about 3:1, about 4:1, about 5:1, about 6:1, about 7:1, about 8:1, about 9:1 (or more) on a dry weight basis. Additionally, there is provided a composition comprising an isolated microorganism from such a culture.

There is also provided herein, in several embodiments, a culture of methanotrophic microorganisms consisting essentially of microorganisms that (a) do not express or contain the genetic material encoding soluble methane monooxygenase, (b) do express or contain the genetic material encoding the ethylmalonyl-CoA pathway, and (c) produce polyhydroxyalkanoate (PHA) at intracellular concentrations wherein the ratio of PHA to non-PHA biomass exceeds about 3:1, about 4:1, about 5:1, about 6:1, about 7:1, about 8:1, about 9:1 (or more) on a dry weight basis. Additionally, there is provided a composition comprising an isolated microorganism from such a culture.

There is additionally provided, in several embodiments, a culture of methanotrophic microorganisms having (a) particulate methane monooxygenase activity in the presence of copper ion concentrations between 0.001 micromolar and 1000 micromolar and (b) ethylmalonyl-CoA pathway activity in the presence of copper concentrations between 0.001 micromolar and 1000 micromolar, wherein said culture is suitable for generation of polyhydroxyalkanoate (PHA) at a ratio of PHA to non-PHA biomass exceeding about 2.9:1, about 3.9:1, about 4.9:1, about 5.9:1, about 6.9:1, about 7.9:1, about 8.9:1 (or more) on a dry weight basis. Additionally, there is provided a composition comprising an isolated microorganism from such a culture.

In several embodiments, the cultures comprise microorganisms of a genus selected from a group consisting of: *Methylosinus, Methylocystis, Methylococcus, Methylobacterium*, and *Pseudomonas*. In some embodiments, said microorganisms are mutants of microorganisms in the genera disclosed herein. As used herein, the term "mutant" shall be given its ordinary meaning and shall also include genetically-engineered mutants, genetically-manipulated variants, selection-pressure-induced mutants, and the like. Selection-pressure-induced mutation, as used herein, shall be given its ordinary meaning and shall also refer to conditions in which the methanotrophic microorganism is cultured that favor one or more microorganisms having certain characteristics. Depending on the embodiments, this may be, for example, ability to upregulate or utilize a particular biochemical or metabolic pathway in response to one or more variables in the culture environment (e.g., nutrients, population density, pH, temperature, salinity, etc.). In several embodiments, the selection-pressure-induced mutation shall also refer to conditions that exploit certain competitive advantages possessed by certain methanotrophic microorganisms and not by others (or possessed or exploited to a lesser extent). In additional embodiments, said microorganisms are epigenetically modified, epigenetically engineered, and/or epigenetically mutated (to produce mutants) such that the microorganisms are capable of producing PHA from carbon-containing gas at high efficiency. As used herein, the terms epigenetic modification, epigenetic mutation, and epigenetic engineering shall be given their ordinary meaning and shall include modification of the expression of the genetic material comprising one or more microorganism, such that the microorganism is caused to produce functionally modified materials, such as enzymes, catalysts, de-coupled feedback loops, conditions-sensitive enzymes, and polymers. In one embodiment, epigenetic engineering is used to cause one or more microorganism to produce one or more biocatalytic pathway that is enhanced for high efficiency PHA production, such that the microorganism is capable of converting or caused to convert metabolized carbon into PHA rather than carbon dioxide, protein, or other non-PHA material. In one embodiment, epigenetic modification is used to cause a greenhouse-gas metabolizing microorganism to produce a biocatalytic pathway (e.g., a pathway of enzymes) that is able to produce PHA at high efficiency. In another embodiment, epigenetic modification is used to cause a greenhouse-gas metabolizing microorganism to produce a biocatalytic pathway (e.g., a pathway of enzymes) that has a deactivated PHA overproduction control mechanism, or functional equivalent thereof, such that the pathway is able to generate (and, in several embodiments, does generate) PHA at high concentrations relative to non-polymer material (e.g., about 1, about 2, about 3, about 4, about 5, about 6, about 7, about 8, about 9, about 10 or more units, by weight, of PHA per 1 unit of biomass), wherein such biocatalytic pathway is otherwise not able (in the absence of epigenetic engineering) to produce PHA at concentrations exceeding 0.5, 0.75, 1, 2, or 3 units PHA per 1 unit biomass (wherein biomass is, e.g., biocatalyst, non-polymer biomass, and/or enzymes produced by a microorganism). In one embodiment, epigenetic engineering is used to produce a biocatalytic pathway (wherein the biocatalyst or biocatalytic pathway comprises, e.g., a conglomerate of enzymes and/or associated feedback and/or production controls that may be contained inside of a microorganism, expressed on the surface of a microorganism, or produced and used as an extracellular or isolated enzyme or conglomerate of enzymes) containing a production control switch, or the functional equivalent thereof, wherein such switch may be regulated (e.g., turned up or down, on or off, low or high, and specifically, turned off to cause the overproduction of PHA relative to non-PHA biomass) according to the concentrations of various proximate factors, including, but not limited to nutrient/chemical concentrations (e.g., such as oxygen, carbon dioxide, methane, volatile organic compounds, methanol, ethanol, propane, ethane, acetic acid, nitrogen, phosphorus, calcium, magnesium, copper, iron, molybdenum, zinc, aluminum, cobalt, etc.), the relative ratio of nutrient/chemical concentrations, the concentration of proximate or comixed gases (dissolved or undissolved, gaseous or aqueous form, chemically bound or unbound, physically concentrated or physically unconcentrated), shear stress, and/or ultrasonic stress. In one embodiment, epigenetic modification is caused by modifying the environmental conditions impacting the methylation of microorganism DNA or other functional agent impacting the expression or replication of various components, such as gene segments, of microorganism DNA, such as stress conditions, e.g., ultrasonic induction or nutrient over/under addition, relative nutrient concentrations, which may be uniquely high, low, or unbalanced (e.g., nutrients such as oxygen, nitrogen, carbon, molybdenum, cobalt, iron, copper, phosphorus, magnesium, zinc, and aluminum). In additional embodiments, such DNA expression modification is used to produce a microorganism or a conglomerate of microorganisms that contains a genetically-enhanced metabolic pathway, wherein such pathway is capable of converting carbon into PHA at uniquely high PHA-to-biomass ratios. In another embodiment, such DNA expression modification via epigenetic mutation is used to cause microorganisms to produce enzymes that possess the ability to produce PHA at very high PHA-to-enzyme concentrations (e.g., above about 3:1, about 4:1, about 5:1, about 6:1, about 7:1, about 8:1, or greater) and at very high or efficient material synthesis rates, wherein such enzymes have a hypoactive PHA production control mechanism, wherein such enzymes have a PHA production control mechanism that can be turned off, reduced, suppressed, or regulated down, wherein such enzymes can be manipulated to produce PHA synthase that is not disabled by high PHA concentrations, wherein such enzymes can be rapidly switched from polymerization to protein production functions.

There are also provided herein, in several embodiments, methods for producing or mutating a microorganism culture such that the culture can produce polyhydroxyalkanoate (PHA) at intracellular or extracellular concentrations exceeding about 60, about 70, about 80, or about 90% by weight, the method comprising: (a) providing a nutrient/culture broth comprising methane, one or more nutrients comprising copper, oxygen, iron, magnesium, phosphorus, molybdenum, cobalt, sulfur, carbon, zinc, potassium, and/or other functional nutrients impacting microorganism metabolism, and a methanotrophic, heterotrophic, and/or autotrophic microorganism; (b) controlling the concentration of one or more nutrient, such as copper, oxygen, iron, magnesium, phosphorus, molybdenum, cobalt, sulfur, carbon, zinc, potassium, and/or other functional nutrients in said medium to a concentration that can enable the microorganism(s) to reproduce, and (c) increasing the concentration of one or more nutrient in said medium to cause said culture or bacterium to produce PHA or increase the production of PHA, including at the expense of carbon dioxide or protein.

There are also provided herein, in several embodiments, methods for producing or mutating a microorganism culture such that the culture can produce polyhydroxyalkanoate (PHA) at intracellular or extracellular concentrations exceeding about 60, about 70, about 80, or about 90% by weight, the method comprising: (a) providing a nutrient/culture broth comprising methane, one or more nutrients comprising copper, oxygen, iron, magnesium, phosphorus, molybdenum, cobalt, sulfur, carbon, zinc, potassium, and/or other functional nutrients impacting microorganism metabolism, and a methanotrophic, heterotrophic, and/or autotrophic microorganism; (b) controlling the concentration of one or more nutrient, such as copper, oxygen, iron, magnesium, phosphorus, molybdenum, cobalt, sulfur, carbon, zinc, potassium, and/or other functional nutrients in said medium to a concentration that can enable the microorganism(s) to produce enzymes, intracellularly or extracellularly, capable of synthesizing PHA, (c) increasing the concentration of one or more nutrient in said medium to cause said enzymes to produce PHA or increase the production of PHA relative to carbon dioxide or protein production, including at the expense of carbon dioxide or protein production.

There are also provided herein, in several embodiments, methods for producing or mutating a microorganism culture such that the culture can produce polyhydroxyalkanoate (PHA) at intracellular or extracellular concentrations exceeding about 60, about 70, about 80, or about 90% by weight, the method comprising: (a) providing a nutrient/culture broth comprising methane, one or more nutrients comprising copper, oxygen, iron, magnesium, phosphorus, molybdenum, cobalt, sulfur, carbon, zinc, potassium, and/or other functional nutrients impacting microorganism metabolism, and a methanotrophic, heterotrophic, and/or autotrophic microorganism; (b) controlling the concentration of one or more nutrient, such as copper, oxygen, iron, magnesium, phosphorus, molybdenum, cobalt, sulfur, carbon, zinc, potassium, and/or other functional nutrients in said medium to a concentration that can enable the microorganism(s) to intracellularly or extracellularly produce enzymes capable of synthesizing PHA, (c) separating the enzymes from the microorganism, (d) contacting carbon with the enzymes, and (e) increasing the concentration of one or more nutrient in said medium to cause said enzymes to produce PHA or increase the production of PHA relative to carbon dioxide or protein production, including at the expense of carbon dioxide or protein production.

There are also provided herein, in several embodiments, methods for producing or mutating a methanotrophic culture or bacterium such that the culture or bacterium can produce polyhydroxyalkanoate (PHA) at intracellular concentrations exceeding about 60, about 70, about 71, about 80, or about 90% by weight in a non-sterile environment, the method comprising: (a) providing a culture broth comprising methane, a medium comprising one or more nutrients comprising copper, and a methanotrophic culture or bacterium; (b) controlling the concentration of copper in said medium to a concentration that can enable methanotrophic microorganisms to produce sMMO, (c) reducing the concentration of one or more nutrient in said medium to cause said culture or bacterium to produce PHA, (d) increasing the concentration of said one or more nutrient of step (c) to cause said culture or bacterium to reproduce using essentially only pMMO, and (e) subjecting said culture or bacterium to at least two repetitions of steps (b), (c), and (d).

In several embodiments, there is provided PHA produced by the cultures or bacterium disclosed herein. In some embodiments, there is provided PHA comprising a culture or bacterium as disclosed herein.

In several embodiments, there is provided the use of microorganisms having the characteristics of (a) producing no soluble methane monooxygenase (or no detectable soluble methane monooxygenase) at any copper concentration, and/or not expressing or containing the genetic material encoding soluble methane monooxygenase; (b) expressing the ethylmalonyl-CoA metabolic pathway; and (c) the capability of producing polyhydroxyalkanoate at intracellular concentrations exceeding about 72% by dry weight, wherein said microorganisms are selected from the group of genera consisting of *Methylosinus, Methylocystis, Methylococcus, Methylobacterium, Pseudomonas*, and mutants thereof, to produce polyhydroxyalkanoate.

In several embodiments, there is also provided the use of microorganisms having the characteristics: (a) producing no soluble methane monooxygenase (or no detectable soluble methane monooxygenase) at any copper concentration (or do not express or contain the genetic material encoding soluble methane monooxygenase); (b) express the ethylmalonyl-CoA metabolic pathway; and (c) the capability to produce polyhydroxyalkanoate at intracellular concentrations exceeding about 57% by dry weight; wherein said microorganisms are selected from the group of genera consisting of *Methylosinus, Methylocystis, Methylococcus, Methylobacterium, Pseudomonas*, and mutants thereof, to produce polyhydroxyalkanoate There is also provided the use of microorganisms having the characteristics (a) produce no soluble methane monooxygenase (or no detectable soluble methane monooxygenase) at any copper concentration (or do not express or contain the genetic material encoding soluble methane monooxygenase); (b) express the ethylmalonyl-CoA metabolic pathway; and (c) capable of producing polyhydroxyalkanoate at intracellular concentrations exceeding about 23% by dry weight; wherein said microorganisms are selected from the a group consisting of *Methylosinus, Methylocystis, Methylococcus, Methylobacterium, Pseudomonas*, and mutants thereof, to produce polyhydroxyalkanoate.

There is provided, in several embodiments, a method for enhancing polyhydroxyalkanoate (PHA) generation in a methanotrophic culture by reducing copper concentrations to effect particulate methane monooxygenase (pMMO) production comprising contacting a culture of methanotrophic microorganisms with a medium comprising copper, one or more additional nutrients, and a carbon-containing gas that can be metabolized by the culture, incubating the culture in the medium to cause growth of the culture, inducing a selection pressure in the culture to transform the culture into a culture that generates PHA preferentially through pMMO by: (i) reducing the concentration of copper in the medium to cause production of soluble methane monooxygenase (sMMO) and/or particulate methane monooxygenase by the culture, wherein the concentration of copper causes the production of sMMO in some methanotrophic microorganisms; (ii) reducing the concentration of one or more the nutrient in the medium to cause the culture to generate PHA from the carbon-containing gas using the sMMO or the pMMO, wherein PHA is generated by pMMO at a greater rate as compared to sMMO, (iii) returning the culture to the growth conditions, wherein microorganisms having higher intracellular concentrations of pMMO and PHA grow at a greater rate as compared to those with lower intracellular pMMO and PHA concentrations; and (iv) repeating steps (ii) and (iii), wherein the repetitions selectively favor growth of microorganisms that produce PHA via pMMO, thereby facilitating the pMMO-mediated production of PHA at reduced copper concentrations, and resulting in a culture comprising essentially only microorganisms that use pMMO to produce PHA.

There is also provided a method for enhancing particulate methane monooxygenase (pMMO) mediated polyhydroxyalkanoate (PHA) generation comprising contacting a culture of methanotrophic microorganisms with a medium comprising copper, nitrogen, one or more additional nutrients, and a carbon-containing gas that can be metabolized by the culture, incubating the culture in the medium to cause growth of the culture; and transforming the culture into a culture that generates PHA preferentially through pMMO by: (i) reducing the concentration of copper in the medium to cause production of soluble methane monooxygenase (sMMO) and particulate methane monooxygenase by the culture, wherein the concentration of copper favors the production of sMMO; (ii) reducing the concentration of nitrogen to cause the culture to generate PHA from the carbon-containing gas using the sMMO or the pMMO, wherein PHA is generated by pMMO at a more rapid rate as compared to sMMO, resulting in a portion of the microorganisms having higher intracellular concentrations of PHA as compared to those using sMMO; and (iii) returning the culture to the growth conditions, wherein the microorganisms having higher intracellular concentrations of PHA grow at a greater rate as compared to those with lower intracellular PHA concentrations; and (iv) repeating steps (ii) and (iii), wherein the repetitions selectively favor growth of microorganisms that produce PHA via pMMO, thereby facilitating the pMMO-mediated production of PHA.

There is also provided, in several embodiments, a method for converting a carbon-containing material into a polyhydroxyalkanoate (PHA), the method comprising (a) contacting a culture of methanotrophic microorganisms with a medium comprising copper, one or more additional nutrients, and a carbon-containing material that can be metabolized by the culture, thereby inducing growth of the culture (b) reducing or controlling the concentration of copper in the medium to cause at least a portion of the culture to produce soluble methane monooxygenase (sMMO) and/or particulate methane monooxygenase (pMMO), wherein the copper concentration can cause one or more methanotrophic microorganism to produce sMMO, (c) reducing the concentration of at least one of the nutrients in the medium to cause at least a portion of the culture to utilize the produced sMMO or the produced pMMO to convert the carbon from the carbon-containing material into PHA, (d) repeating steps (a) through (c) a plurality of times, wherein the portion of the culture utilizing the pMMO to generate PHA grows and/or generates PHA at a greater rate than the portion of the culture utilizing the sMMO to generate PHA, thereby inducing a selective pressure in the culture resulting in a culture comprising essentially only microorganisms that use pMMO to produce PHA.

In several embodiments, the induced selection pressure selects for microorganisms in which the presence and/or expression of the gene encoding the sMMO is reduced. This is unexpected, in several embodiments, as the copper concentrations are such that sMMO production would typically be favored. When employed in combination with periods of growth, PHA production, and growth, the selection pressure unexpectedly and advantageously allows those microorganisms operating through the pMMO pathway to become grow more quickly, thereby outcompeting many, if not all, organisms using an alternate MMO pathway. In several embodiments, as the growth-polymerization-growth cycles are repeated in conjunction with the existence of conditions favoring pMMO metabolism, the expression of the gene encoding the soluble methane monooxygenase enzyme is reduced. Thus, the growth advantage of those microorganisms utilizing pMMO provides, in each cycle, at least a marginal gain with respect to the sMMO-utilizing microorganisms increasing their percentage contribution to the overall demographics of the culture. With each successive round, pMMO-utilizing microorganisms outcompete the sMMO-utilizing microorganisms, thereby eventually being the primary, if not only, microorganism in the culture. As a result this process, the "weaker" sMMO-utilizing microorganisms will be reduced in number, and in some cases may undergo an evolutionary-pressure induced change to reduce/eliminate sMMO expression in favor of pMMO.

In additional embodiments, alternative methods may be used to achieve a reduction in the presence and/or expression of the sMMO gene and/or protein. For example, as disclosed herein genetically modified (also referred to herein as genetically-engineered) microorganisms may be used in certain embodiments. Thus, prior to a culturing process in which PHA would be produced, in some embodiments, microbiological techniques are used to excise the genetic material encoding sMMO from the genome of the microorganism. Similarly, microorganisms having the genetic material for sMMO could be cultured with (e.g., bred with) an alternative strain of microorganisms having genetic material for a metabolically favorable (e.g., more active) pMMO. After successive rounds of crossbreeding, microorganisms are selected based on a combination of limited sMMO expression and robust high activity pMMO expression. In additional embodiments, methods can be used to suppress one or more of the expression where the activity of the sMMO enzyme, rather than manipulating the microorganism on genomic level. For example, RNA interference or antisense RNA could be used to suppress expression and/or function of sMMO. Similarly site directed mutagenesis could be used such that a microorganism would produce a mutant (e.g., nonfunctional or minimally functional) sMMO. Site directed mutagenesis can also be employed to introduce a specific mutation in the sMMO gene such that a truncated and/or nonfunctional (or reduced function) S MMO is produced. For example, the introduction of mutation that results in early placement of a stop codon in the sMMO gene would result in a truncated, and likely non-functional enzyme (if any enzyme and all were in fact be produced). In addition to, or in place of such approaches, inducible or repressible promoters could be employed such that sMMO would only be expressed under certain conditions (e.g., the addition of an inducing agent to the culture media) or alternatively would normally be repressed absent the removal of repressing agent from the media. Akin to gene therapy approaches, microorganisms could be modified to carry exogenous DNA that produces a repressor of sMMO function (or alternatively, a promoter of pMMO function).

In some embodiments, the actual and/or bioavailable concentration of the copper in the medium is reduced to a concentration less than about 0.001 mg/L, less than about 0.5 micromolar, less than about 0.1 mg per dry weight gram of the microorganisms, less than about 100 mg/L, or less than about 1 mg/L. In some embodiments, the concentration of copper is maintained at the reduced level. In some embodiments, the copper concentration is returned to initial concentrations. In several embodiments, reduction of one or more additional nutrient comprises a substantial depletion of nitrogen from the media. Substantial depletion comprises, in some embodiments, depletion of nitrogen concentrations by about 50%, about 60%, about 70%, about 80%, about 90%, about 95%, or more. In other embodiments, depending on the metabolic status of the culture, smaller reductions in nitrogen, another nutrient in the media, or combinations thereof may be used to effect PHA polymerization.

In several embodiments, the carbon-containing gas that the culture uses as a source of carbon to generate PHA comprises methane. In some embodiments, the carbon-containing gas comprises carbon dioxide. In some embodiments, the carbon-containing gas comprises one or more volatile organic compounds. In some embodiments, one or more of methane, carbon dioxide, volatile organic compounds, and other gasses or compounds may be present in the carbon-containing gas.

In some embodiments, the carbon source need not be a gas. A carbon-containing material comprising a non-gaseous material (either alone or in combination with a gas) may also be used in certain embodiments. For example, in some embodiments, the non-gaseous material comprises one or more volatile fatty acids, methanol, acetate, acetone or acetic acid, formate, formaldehyde or formic acid, propane, ethane, or combinations thereof (or in combination with other metabolizable carbonaceous materials). In addition, in some embodiments, the non-gaseous material comprises microorganism biomass removed from one polymerization stage and added to the medium in a subsequent growth stage. In one embodiment, methanotrophic microorganisms are exposed to acetic acid and/or acetate to cause said microorganisms to reproduce or generate chemicals, such as PHA. In another embodiment, methanotrophic microorganisms are exposed to acetic acid and/or acetate together with methane, independent of methane, or periodically with methane and periodically without methane, wherein said acetate or acetic acid may be derived by chemically, electrochemically, and/or biologically converting carbon dioxide into acetic acid or acetate, wherein non-obligate (facultative) methanotrophic microorganisms use such acetic acid or acetate to produce biomass, protein, PHA, methanol, butanol, cartenoids, chemicals, or other materials. In one embodiment, electrical current is added to a methanotrophic culture to cause the culture to produce higher amounts of PHA than the culture would produce without the addition of an electrical current. In another embodiment, methanotrophic microorganisms are exposed to concentrations of nitrogen, potassium, magnesium, carbon dioxide, methane, dinitrogen, or other chemicals, and particularly carbon dioxide, that induce said microorganisms to produce one or more chemicals, such as methanol, butanol, ethanol, or other alcohols, and particularly methanol, wherein said alcohol is excreted extracellularly, wherein the concentration of gases/nutrients, such as carbon dioxide, nitrogen, potassium, magnesium, methane, dinitrogen, or other chemicals, is used to induce, control (e.g., maintain), and/or increase the extracellular production of alcohol or other chemicals from said microorganisms. In another embodiment, a culture of methanotrophic, heterotrophic, and/or autotrophic microorganisms are contacted with an electric current or other agent, wherein carbon dioxide is converted to acetic acid or acetate, wherein such acetic acid or acetate is subsequently utilized as a source of carbon by said microorganisms to produce PHA, chemicals, proteins, or other materials, wherein such carbon dioxide may or may not be derived as a metabolic byproduct of methanotrophic metabolism. In another embodiment, a method is provided for converting carbon dioxide into PHA or other materials using a methanotrophic microorganism, the method comprising converting carbon dioxide into acetic acid or acetate and inducing a methanotrophic microorganism to convert such acetic acid or acetate into biomass, protein, PHA, methanol, butanol, or other materials, wherein such process of converting carbon dioxide to acetic acid or acetate (or other carbon-containing chemical that can be assimilated and metabolized by either a methanotrophic microorganism or other microorganism, such as a heterotrophic microorganism) and subsequently converting such acetic acid, acetate, or carbon-containing chemical into PHA, biomass, methanol, butanol, or another chemical takes place in one, two, or multiple vessel(s). In one embodiment, methanotrophic microorganisms are caused to increase the production of extracellularly excreted methanol, butanol, ethanol, other liquids or volatile organic compounds, lipids, PHAs, or proteins, which can be excreted in media or gas, by increasing the actual or relative concentration of a nutrient, wherein such nutrient may be one or more of carbon, hydrogen ions, hydroxide ions, oxygen, hydrogen, carbon dioxide, methane, nitrogen, dinitrogen, urea, acetic acid, volatile organic compounds, organic compounds, inorganic compounds, silicon, magnesium, sodium, EDTA, calcium, phosphorus, zinc, cobalt, cadmium, aluminum, potassium, electrons, or other nutrient or metabolism-influencing material, and particularly carbon dioxide, magnesium, electrons, and/or sodium, thereby, in one embodiment, inducing a metabolic shift in the proclivity or ability of a methanotroph to produce or use methanol-metabolizing enzymes. In one embodiment, such extracellularly excreted chemical (such as methanol, ethanol, or PHA) is harvested by heating the liquid media, subjecting the liquid media or proximate gas to a scrubber, such as a water scrubber to absorb, e.g., alcohols, subjecting liquid media to a vacuum to cause such chemical to vaporize, subjecting the media to a pervaporator, and/or subsequently reducing the concentration of water in the chemical, or reducing the concentration of chemical in the water, or reducing the concentration of chemical in the proximate gas stream. In one embodiment, the production of proteins, PHAs, or other chemicals, such as diesel, methanol, gasoline, butanol, vaccines, therapeutics, and other chemicals, may be carried out using methanotrophic microorganisms as a method to avoid one or more Maillard reactions. Since methanotrophic metabolism neither requires nor inherently produces sugars, methanotrophy, in one embodiment, is used as a platform to avoid Maillard reactions in the production of proteins and other chemicals. In one embodiment, methanotrophic microorganisms are used to produce materials that are currently challenged by the occurrence (and resulting hindrance) of one or more Maillard reactions, such as in the production of antibiotics, antibodies, pharmaceuticals, and/or platform chemicals. In one embodiment, methanotrophic microorganisms are employed to produce materials in processes while avoiding Maillard reactions or the products of glycation.

Advantageously, the methods disclosed herein allow production PHA at high intracellular concentrations. The concentrations, in some embodiments, are at least 70% of the dry biomass weight of the microorganisms. In some embodiments, the concentrations are particularly advantageous because the high intracellular PHA concentration enables more rapid growth of those microorganisms. Thus, a feed-forward cycle exists, in some embodiments, in that a microorganism that is selected for by the induced pressures produces PHA more rapidly through the pMMO pathway, thereby having a greater concentration of PHA, which further imparts the ability to grow more rapidly (vis-à-vis those microorganisms with lower PHA concentrations, such as those utilizing the sMMO pathway). As the process is repeated, the pMMO-utilizing microorganisms possess a growth advantage at (at least) two stages in the process, thereby allowing their dominance in the culture. As such, in several embodiments, the culture comprising essentially only microorganisms that use pMMO to produce PHA comprises a culture wherein over about 50% of the culture uses pMMO to produce PHA. Additionally, in several embodiments, the culture comprising essentially only microorganisms that use pMMO to produce PHA comprises over 80% of the culture. In several embodiments, the microorganisms in the culture are from the genus *Methylocystis*.

In addition, several embodiments, the repeated cycling between growth, copper reduction to favor pMMO production, PHA production and back to growth also favors the production of microorganisms that possess the genetic material encoding the ethylmalonyl-CoA pathway. Advantageously, this pathway allows, in some embodiments, additional carbon sources to be used by the culture, thereby broadening the range of substrates that can eventually be used as substrates for the generation of PHA.

A method for converting a carbon-containing material into a polyhydroxyalkanoate is also provided in several embodiments, the method comprising: (a) contacting a methanotrophic culture with a medium comprising one or more nutrients and a carbon-containing material that can be metabolized by the culture, (b) controlling the concentration of the one or more nutrients in the medium to cause at least a portion of the culture to produce sMMO and/or pMMO, (c) controlling the concentration of the one or more nutrients in the medium to cause the culture to produce PHA; (d) repeating steps (a) through (c) a plurality of times.

In several embodiments, the nutrient of step (b) and the nutrient of step (c) are the same nutrient, while in other embodiments, the nutrient of step (b) and the nutrient of step (c) are different nutrients. In one embodiment, the nutrient is selected from the group consisting of copper, methane, oxygen, phosphorus, potassium, magnesium, boron, sodium, calcium, nitrogen, iron, carbon dioxide, and combinations thereof.

Also provided for in several embodiments herein is a method for converting a carbon-containing material into a polyhydroxyalkanoate (PHA), the method comprising: (a) providing a microorganism culture, (b) providing a medium comprising one or more nutrient comprising a carbon-containing material that can be metabolized by the culture, (c) controlling the concentration of the one or more nutrient in the medium to cause the cellular replication of one or more microorganisms in the culture, wherein the genetic material encoding the ethylmalonyl-CoA pathway is present in the one or more microorganisms, (d) controlling the concentration of the one or more nutrient in the medium to cause the culture to produce PHA, and (e) repeating steps (a) through (d).

In several embodiments, the nutrient is copper, and step (c) comprises periodically or permanently reducing the concentration of the copper in the medium. In several embodiments, the actual and/or bioavailable concentration of the copper in the medium to be less than about 0.001 mg/L, less than about 0.5 micromolar, less than about 0.1 mg per dry weight gram of the microorganisms, less than about 100 mg/L, or less than about 1 mg/L. In several embodiments, controlling the actual and/or bioavailable concentration of the copper in the medium effects the production of microorganisms that do not possess the gene encoding soluble methane monooxygenase or express sMMO at reduced amounts. In other embodiments, the organisms have the gene, but the enzyme is not expressed.

In some embodiments, the nutrient is selected from the group consisting of copper, methane, oxygen, phosphorus, potassium, magnesium, boron, sodium, calcium, nitrogen, iron, carbon dioxide, and combinations thereof, and step (c) comprises periodically or permanently increasing, reducing, or maintaining the concentration of the nutrient in the medium to effect the production of microorganisms that do not possess the gene encoding soluble methane monooxygenase. In several embodiments, the nutrient of step (c) and the nutrient of step (d) are the same nutrient, while in other embodiments, the of nutrient of step (c) and the nutrient of step (d) are different nutrients.

In several embodiments, steps (a) through (d) are repeated a plurality of times and the concentration of the one or more microorganisms in the culture increases as the steps (a) through (d) are repeated.

There is also provided, in several embodiments, a method for converting a carbon-containing material into a polyhydroxyalkanoate (PHA), the method comprising: (a) providing a microorganism culture, (b) providing a medium comprising one or more nutrient comprising a carbon-containing material that can be metabolized by the culture, (c) controlling the concentration of the one or more nutrient in the medium to cause the cellular replication of one or more microorganisms in the culture, wherein the genetic material encoding the ethylmalonyl-CoA pathway is present in the one or more microorganisms, and wherein the expression of soluble methane monooxygenase is reduced in the one or more microorganisms as compared to a first instance of step (a), (d) controlling the concentration of the one or more nutrient in the medium to cause the culture to produce PHA, and (e) repeating steps (a) through (d).

Copper concentrations can be reduced, in several embodiments, as discussed herein, e.g., to concentrations less than about 0.001 mg/L, less than about 0.5 micromolar, less than about 0.1 mg per dry weight gram of the microorganisms, less than about 100 mg/L, or less than about 1 mg/L. Also as discussed above, the nutrients can be the same in various steps, or alternatively they may be different. In one embodiment, for example, the nutrient of step (c) is selected from the group consisting of methane, oxygen, phosphorus, potassium, magnesium, boron, sodium, calcium, nitrogen, iron, carbon dioxide, and combinations thereof and the nutrient of step (d) is selected from the group consisting of methane, oxygen, phosphorus, potassium, magnesium, boron, sodium, calcium, nitrogen, iron, carbon dioxide, and combinations thereof, but is not the same as the nutrient of step (c).

There is also provided a method for controlling the functional characteristics of polyhydroxyalkanoate (PHA) produced by a methanotrophic culture exposed to methane and one or more non-methane materials that influence the metabolism of the culture, the method comprising: (a) providing a methanotrophic culture in a medium comprising one or more nutrients, (b) controlling the concentration of one or more of the nutrients in the medium to cause the culture to produce soluble methane monooxygenase (sMMO) and/or particulate methane monooxygenase (pMMO), (c) controlling the concentration of the one or more nutrients in the medium to cause the culture to produce PHA, and (d) repeating steps (a) through (c), wherein the concentration of sMMO relative to pMMO in step (c) is substantially the same in each repetition, wherein one or more functional characteristics of the PHA produced by the culture are controlled in multiple PHA production repetitions, and wherein the culture selectively generates microorganisms that synthesize PHA at high efficiency.

In several embodiments, the concentration of the sMMO relative to the pMMO in the culture is substantially the same in step (c) in at least two consecutive repetitions. Advantageously, this consistency results in a more defined and predictable PHA. For example, in several embodiments, PHA produced by the culture exhibits substantially the same of one or more of the following characteristics in one or more the repetitions: molecular weight, polydispersity, impact strength, elasticity, elongation, and/or modulus. As discussed above, a variety of carbon sources may be used. In some embodiments, non-methane sources are used, such as carbon dioxide, volatile organic compounds, volatile fatty acids, methanol, acetate, acetone, and acetic acid, formate, formaldehyde, and formic acid, propane, ethane, oxygen, a carbon-containing material that can be metabolized by the culture, or combinations thereof.

In one embodiment, at least about 60% of microorganisms in the culture produce only the pMMO, while in one embodiment at least about 60% of microorganisms in the culture produce only the sMMO. In still additional embodiments, the culture comprises an equal concentration of the sMMO and the pMMO. In one embodiment, the concentration of the sMMO is more than 2 times greater than the concentration of the pMMO in the culture. In one embodiment, the concentration of the sMMO is more than 5 times greater than the concentration of the pMMO in the culture. In one embodiment, the concentration of the sMMO is more than 10 times greater than the concentration of the pMMO in the culture. In other embodiments, the concentration of the pMMO is more than 2 times greater than the concentration of the sMMO in the culture. In one such embodiment, the concentration of the pMMO is more than 5 times greater than the concentration of the sMMO in the culture.

There is also provided a method for modifying the functional characteristics of a polyhydroxyalkanoate (PHA) material, comprising the steps of: (a) providing a PHA and a biomass, (b) subjecting the PHA and/or the biomass to a processing step in order to render the at least a portion of the biomass miscible with the PHA, (c) combining the PHA and the biomass in a mixture to form a compound, (d) heating the compound to between 50 degrees Celsius and 250 degrees Celsius, and (e) causing the biomass to effect a functional modification of the PHA, wherein the functional modification comprises plasticization, nucleation, compatibilization, melt flow modification, strengthening, reduction of PHA crystallinity or rate of crystallization, increase in optical clarity, and/or elasticization. In one embodiment, there is also provided a method for modifying the functional characteristics of a polyhydroxyalkanoate (PHA) material, comprising the steps of: (a) providing a PHA and a biomass, (b) subjecting the PHA and/or the biomass to a processing and modification step wherein the PHA and the biomass are subject to temperatures between at least 20 degrees Celsius and 250 degrees Celsius and to pressures of at least between 1 atmosphere and 350 atmospheres, thereby causing the modified biomass to effect a functional modification of the PHA material, wherein the functional modification comprises an increase in plasticization, nucleation, compatibilization, melt flow modification, strengthening, and/or elasticization. In one embodiment, the ratio of biomass to PHA in said PHA material may be between about 1:1000 and about 1000:1, including between about 1:1000 and about 1:500, about 1:500 and about 1:100, about 1:100 and about 1:10, about 1:10 and about 1:9, about 1:9 and about 1:8, about 1:8 and about 1:5, about 1:5 and about 1:3, about 1:3 and about 1:1, about 1:1 and about 2:1, about 2:1 and about 5:1, about 5:1 and about 10:1, about 10:1 and about 100:1, about 100:1 and about 500:1, and about 500:1 about 1000:1, and overlapping ratios therein. In one embodiment, the temperature, in degree Celsius, of the modification step may range from about 20 to about 40, about 40 to about 60, about 60 to about 80, about 80 to about 100, about 100 to about 120, about 120 to about 140, about 140 to about 200, about 140 to about 160, about 160 to about 180, about 180 to about 200, about 200 to about 220, about 220 to about 250, about 250 to about 300, about 90 to 200, about 140 to about 220, about −50 to about 400, and overlapping ranges thereof. In one embodiment, the pressure, pounds per square inch, of the modification step may range from about −30 to about 50,000, about −30 to about 0, about 0 to about 50, about 0 to about 3,000, about 0 to about 200, about 0 to about 10,000, about 0 to about 5,000, about 0 to about 20,000, about 20,000 to about 50,000, about 10,000 to about 40,000, about 25,000 to about 30,000, about 0 to about 500, about 0 to about 1000, about 0 to about 2,000, about 40,000 to about 50,000, and overlapping ranges thereof. In one embodiment, the modification step may be used to eliminate the need for one or more of additional plasticization, nucleation, compatibilization, melt flow modification, strengthening, reduction of PHA crystallinity or rate of crystallization, increase in optical clarity, and/or elasticization.

Advantageously, a variety of types of biomass may be used, for example, one or more of methanotrophic, autotrophic, and heterotrophic biomass are used in several embodiments. In one embodiment, the processing comprises treating the PHA and/or the biomass with one or more of the treatments selected from the group consisting of: heat, shear, pressure, solvent extraction, washing, filtration, centrifugation, sonication, enzymatic treatment, super critical material treatment, cellular dissolution, flocculation, acid and/or base treatment, drying, lysing, and chemical treatment.

The biomass may be present at varied concentrations, depending on the embodiment. For example in one embodiment, the biomass is present in the compound at a concentration of more than 0.001%, while in other embodiments, the biomass is present in the mixture at a concentration of more than 0.01%. In still other embodiments, depending on the make-up of the biomass and the characteristics of the PHA, greater or lesser concentrations may also be used.

The functional characteristics of PHA may also be modified through the melting and cooling of the PHA polymer in the presence of a dual-miscible biomass agent and a second polymer by a method provided in several embodiments herein, the method comprising, comprising the steps of: (a) providing a first polymer, a biomass, and a second polymer, wherein the first polymer is a PHA, (b) subjecting the biomass to a processing step comprising heat, pressure, solvent washing, filtration, centrifugation, super critical solvent extraction, and/or shear, wherein the processing step renders at least a portion of the biomass miscible with the first polymer and the second polymer, (c) contacting the first polymer with the biomass and the second polymer to form a compound, (d) heating the compound to between about 50 degrees Celsius and about 250 degrees Celsius and adding pressure to the compound between about 0 and about 50,000 pounds per square inch, thereby causing the biomass to effect a functional modification of the first polymer, the second polymer, and the combination of the first polymer and the second polymer, wherein the functional modification comprises plasticization, nucleation, compatibilization, melt flow modification, strengthening, reduction of PHA crystallinity or rate of crystallization, increase in optical clarity, and/or elasticization. In one embodiment, PHA may be mixed and/or co-melted with a miscible agent to reduce the crystallinity, increase the clarity, increase the flexibility, and/or lower the melting point of the PHA, wherein such PHA may be PHB, PHBV, PHHX, PHO, or other PHA polymer. In one embodiment, such miscible agents include plasticizers that reduce crystallinity, increase clarity, increase flexibility, and reduce the melt temperature of PHA, in concentrations ranging from about 0 to about 100%, about 0 to about 30%, about 0 to about 20%, about 0 to about 15%, about 0 to about 10%, about 5 to about 10%, about 0to about 5%, or other concentration. In one embodiment, the degradation temperature of PHB or PHBV may be increased by purifying (at least partially) the PHB or PHBV, wherein purifying the PHB or PHBV comprises reducing the concentration of proximate salts, biomass, or other non-PHA materials, thereby reducing the loss of PHA molecular weight induced by the presence of such non-PHA materials in a high temperature condition. In another embodiment, PHA may be degraded into low molecular weight PHA, such as low molecular weight (MW) PHB, to produce oligomers, dendrimers, or other low MW derivatives, such that such low MW PHA can be used as a plasticizer, compatibilizer, or functional modification agent in PHA, PVC, polyproylene, polyethylene, ABS, TPU, polystyrene, or other chemicals or polymers; such low MW PHA provides surprisingly useful features as a plasticizer, compatibilizer, and/or as a miscible agent, including compatibilization and/or plasticization with non-PHA materials, such as polyolefins. In another embodiment, PHA may be degraded into low molecular weight PHA, crotonic acid, PHA monomers (e.g., such as hydroxybutyrate), or other PHA derivative by thermal degradation, enzymatic degradation, or otherwise, and such low MW PHA or PHA derivatives may be reconstructed as building blocks into a polymer or other chemical through the use of a catalyst, compatibilizer, cross-linker, nucleating point, star-block creating polymer, random co-polymer, chemical intermediary, or other chemical agent that serves to use PHA, low MW PHA, or PHA derivatives as units for polymerization or chemical construction. In one embodiment, miscible agents, such as chemicals with acetic acid or acetyl or acetic groups, are added to PHA to reduce crystallinity and/or increase clarity, wherein a PHA is rendered more amorphous. In other embodiments, the clarity of PHA itself, or the mixture of PHA with other non-PHA polymers, such as polyolefins, PLA, or other polymers, is increased by adjusting the refractive index of either PHA or the non-PHA polymers, such that the refractive indices of the various polymers are caused to come into closer proximity. In other embodiments, the crystal sizes and domains of PHA are reduced through the addition of one or more nucleating agents, such as boron nitride (including various grades of boron nitride, including from various manufacturers providing varying degrees of clarity, including from about 0to about 1%, about 0 to about 0.2%, about 0to about 3%, about 0to about 0.1%, about 0 to about 10%, about 0to about 20%, about 1 to about 2%, and various overlapping ranges therein); suitable nucleating agents may also include miscible agents or plasticizers that are caused to dissolve into PHA or otherwise produce a homogenous mixture, including nucleating agents that come out of solution below the melt temperature of PHA but form a soluble mixture with PHA at or above the melting temperature of PHA, thereby forming highly dispersed, fine, or otherwise effective nucleation points, which may reduce crystallinity, reduce haze, increase compatibilization with non-PHA materials, increase clarity, reduce brittleness, improve toughness, increase crystallization temperature, and/or reduce secondary crystallization. In one embodiment, secondary crystallization in a PHA is reduced or eliminated by increasing the PHA crystallization temperature by reducing or eliminating the crystallinity of PHA through the use, e.g., of plasticization, comixing PHA with other miscible agents, comixing PHA with polyolefins, adding antioxidants to PHA, or adding compatibilization agents to PHA. In one embodiment, PHAs are comixed and/or melt blended with other non-PHA polymers or materials, such as polypropylene (homopolymer, copolymer, random copolymer, wherein random copolymers are particularly useful by increasing the ethylene content of the material to lower melt temperature, increase co-compatibilization, reduce crystallinity, and increase toughness), glass fibers, organic fibers, inorganic fibers, wood fibers, calcium carbonate (at various particle size distributions and at various injection points, such that $CaCO_3$ at low/fine particle size will be more functional as part of a PHA blend than higher particle size $CaCO_3$), polyethylene (including linear low density polyethylene, low density PE, high density PE, wherein PE reduces the crystallinity of PHA, including PHB, reduces the melt temperature, and reduces secondary crystallization), ABS, glass-filled PP, TPU (including with TPU-PHA compatibilizers), polystyrene (including high impact polystyrene), PET, PMMA, biomass, wood, hemp fibers, polyolefins, other non-PHA polymers, and/or antioxidants. In some embodiments, PHAs are functionally modified and/or enhanced through the addition/compounding with: 1) plasticizers, such as tributyl citrate, at a variety of concentrations, 2) nucleating agents, such as boron nitride, 3) antioxidants, 4) fibers, 5) cross-linking agents (such as peroxides), 6) low or high glass transition temperature materials that may be miscible with PHA, 7) low MW PHAs, such as low MW PHB or PHBV, 8) biomass, and/or biomass derivatives, and/or 8) non-PHA polymers or non-PHA materials. In one embodiment, the non-PHA polymer or material consists of one or more of the following solvents, cell dissolution agents, cell metabolizing agents, polymers, plasticizers, compatibilization agents, miscible agents, and nucleating agents: polypropylene, polyethylene, polystyrene, polycarbonate, acrylonitrile butadiene styrene, polyethylene terephthalate, polyvinyl chloride, fluoropolymers, liquid crystal polymers, acrylic, polyamide/imide, polyarylate, acetal, polyetherimide, polyetherketone, nylon, polyphenylene sulfide, polysulfone, cellulosics, polyester, polyurethane, polyphenylene oxide, polyphenylene ether, styrene acrylonitrile, styrene maleic anhydride, thermoplastic elastomer, ultra high molecular weight polyethylene, epoxy, melamine molding compound, phenolic, unsaturated polyester, polyurethane isocyanates, urea molding compound, vinyl ester, polyetheretherketone, polyoxymethylene plastic, polyphenylene sulfide, polyetherketone, polysulphone, polybutylene terephthalate, polyacrylic acid, cross-linked polyethylene, polyimide, ethylene vinyl acetate, polyvinyl chloride, polyvinyl acetate, polyvinyl acetate co-polyvinylpyrrolidone, polyvinylpyrrolidone, polyvinyl alcohol, cellulose, lignin, cellulose acetate butyrate, polypropylene, polypropylene carbonate, propylene carbonate, polyethylene, ethyl alcohol, ethylene glycol, ethylene carbonate, glycerol, polyethylene glycol, pentaerythritol, polyadipate, dioctyl adipate, triacetyl glycerol, triacetyl glycerol-co-polyadipate, tributyrin, triacetin, chitosan, polyglycidyl methacrylate, polyglycidyl methacrylate, oxypropylated glycerine, polyethylene oxide, lauric acid, trilaurin, citrate esters, triethyl citrate, tributyl citrate, acetyl tri-n-hexyl citrate, saccharin, boron nitride, thymine, melamine, ammonium chloride, talc, lanthanum oxide, terbium oxide, cyclodextrin, organophosphorus compounds, sorbitol, sorbitol acetal, sodium benzoate, clay, calcium carbonate, sodium chloride, titanium dioxide, metal phosphate, glycerol monostearate, glycerol tristearate, 1,2-hydroxystearate, cellulose acetate propionate, polyepichlorohydrin, polyvinylphenol, polymethyl methacrylate, polyvinylidene fluoride, polymethyl acrylate, polyepichlorohydrin-co-ethylene oxide, polyvinyl idene chloride-co-acrylonitrile, polycyclohexyl methacrylate, cellulose acetate butyrate, cellulose, starch, cellulose acetate butyrate-g-polyethyelene glycol, polyvinylidene chloride co-acrylonitrile, polyvinyl acetate, polyethylene glycol b-poly(e-caprolactone), R-PHB-OH, S-PHB-OH, polyphenol poly(4,4'-dihydroxydiphenyl ester, 4-tert-butylphenol, polyglutamate, acrylonitrile-butadiene-styrene, polystyrene, styrene acrylonitrile, polyethylene 2,6-napthalate, polypropylene oxide, polyethylene terepthalate, polybutylacrylate, poly-y-benzyl-1-glutamate, starch-b-PPG-urethane, ethylene propylene rubber-g-sodium acrylate EPR-g-SA, polypropylene carbonate, polypropylene carbonate-co-polyvinyl acetate, natural starch, starch adipate, starch-b-polyester-urethane, starch-b-PEG-urethane, PHBV, polycaprolactone, PLLA, polyoxymethylene, polyvinyl acetate-co-vinyl alcohol, ethylene-propylene rubber, ethylene-vinyl-acetate copolymer, synthetic poly3-hydroxybutyrate, poly-3-hydroxybutyrate-co-poly-3-hydroxyvalerate, poly-3-hydroxypropionate, polybutylene succinate-co-butylene adipate, polybutylene succinate-co-caprolactone, phenol poly(4,4'-dihydroxydiphenyl ester, styrene maleic anhydride, styrene-acrylonitrile, poly(methyl methacrylate), polytetrafluoroethylene, polybutylene. polylactic acid, polyvinylidene chloride, and/or other similar materials or combinations of these materials, including mold release agents, plasticizers, solvents, solvent-grafted polymer, salts, nucleating agents, cross-linking agents, filaments, water, antioxidants, compatibilizers, co-polymers, peroxides, alcohols, ketones, polyolefins, chlorinated solvents, non-chlorinated solvents, aliphatic hydrocarbons, hydrophilic agents, impact modifiers, such as rubber, epoxidized rubber, maleated rubber, Engage™, Loditer, and other such materials, hydrophobic agents, enzymes, PHA miscible agents, pigments, stabilizers, and/or rubbers. In additional embodiments, copolymers and/or other compatibilizers comprise random copolymer polypropylene or other polymers that include two or more monomers, wherein one of the polymer of monomer groups may have a higher miscibility or compatibility than PHA than the other polymer or monomer. In several embodiments, the additional of one or more of such non-PHA polymer or material advantageously improves the post-production handling of PHA. In one embodiment, PHA, such as PHB or PHBV, is mixed with one or more of PP, PE, PVC, ABS, PS, TPU, PET, HIPS, BOPP, PP (random copolymer), PP (homopolymer), PP (copolymer), PP (clarified), PE (linear low density), PE (low density), PE (high density), PS (high impact), PS (crystalline), PS (semi-crystalline), wherein the concentration of PHB is about 0.1 to about 99.9%, including about 1%, about 3%, about 5%, about 8%, about 9%, about 10%, about 15%, about 20%, about 25%, about 30%, about 50%, about 70%, about 90%, about 99.9%, or percentages between these percentages, wherein an impact modifier is added at about 0.01% to about 99%, including about 0.01%, about 2%, about 0.1%, about 5%, about 20%, about 90%, or percentages between these percentages, a pigment or pigment altering substance, including a clarifying pigment, such as blue, red, yellow, green, white, or clear nucleation (to provide clarity), a filler, fiber, or composite-generating material (such as wood fiber, rubber, calcium carbonate, glass, glass fiber, long glass fiber), and/or one or more antioxidant, stabilizer, plasticizer, or compatibilizer. In one embodiment, a compound is provided comprising, by weight, about 88% PP (random copolymer), about 9% PHB (molecular weight between approximately 1000 and approximately 5,000,000 Daltons, wherein molecular weight may be adjusted to improve the compatibility of PHB with PP, or improve the clarity of the compound, or cause PHB to act as a plasticizer for the PP phase), wherein one advantage of this percentage is that it does not impact the recyclability and/or biodegradability of the compound, about 2% Engage impact modifier, and about 1% clarifying (nucleating) pigment. In one embodiment, a compound is provided comprising, by weight, about 87% PP (random copolymer), about 10% PHB (molecular weight between approximately 1000 and approximately 5,000,000 Daltons, wherein molecular weight may be adjusted to improve the compatibility of PHB with PP, or improve the clarity of the compound, or cause PHB to act as a plasticizer for the PP phase), wherein one advantage of this percentage is that it does not impact the recyclability and/or biodegradability of the compound, about 2% Engage impact modifier, and about 1% clarifying (nucleating) pigment. In one embodiment, the molecular weight of the PHA, including PHB or PHBV, is specifically tailored to between about 100 and about 3,000,000 Daltons to provide optimal clarity, functionality, and/or compatibility with the non-PHA material, such as PP, PE, PVC, ABS, PET, fillers, pigments, impact modifiers, plasticizers, or other functional modification materials. In one embodiment, the molecular weight of PHA is controlled by inducing a heat treatment step to reduce molecular weight and thereby improve the compatibility of PHA with other materials, including PHA and non-PHA materials. In another embodiment, PHA is functionally enhanced by increasing the polydispersity of the PHA material to above about 1 and less than about 5, thereby causing the PHA to exhibit reduced crystallinity and/or improved performance and/or compatibilization with PHA or non-PHA materials by causing parts of the PHA to act as self-plasticizer, self-nucleator, self-compatibilizer (e.g., improving the strength of the bonds between the PHA molecules), self-impact modifier, and/or plasticizer, nucleator, compatibilizer, or impact modifier.

In additional embodiments, the clarity of PHA is increased through a function of directed or passive crystal orientation, whereby crystals may be oriented parallel to or perpendicular from, for example, a film processing extrusion die. In one embodiment, a biaxial orientation machine used for the production of biaxially oriented polypropylene may be employed to produce high clarity PHA films or other materials. In one embodiment, the crystals of PHA may also be oriented to increase clarity in an extruder and/or pelletization system via directed stretching, cooling, chemical treatment, electrical treatment, sonic treatment, or other treatment that causes PHA crystals to align in such a manner that less or smaller crystals are formed, or the crystal formations enable greater material flexibility. In an additional embodiment, the clarity and/or miscibility of PHA with other PHAs or non-PHA polymers is increased by reducing the molecular weight of the PHA and/or increasing the polydispersity of PHA. In one embodiment, the molecular weight and/or polydisperity of PHA is lowered (e.g., from about 500,000 Daltons to less than about 100,000 Daltons) to increase the clarity and/or miscibility of PHA. Without being limited by theory, PHA with low MW or high polydispersity can surprisingly act as a self-nucleating and/or self-plasticizing material, which yields surprisingly useful functional improvements, such as increased clarity, increased flexibility, increased miscibility, increased plasticity, and increased toughness.

If incorporating biomass, the biomass may be present at varied concentrations, depending on the embodiment. For example in one embodiment, the biomass is present in the compound at a concentration of more than about 0.001%, while in other embodiments, the biomass is present in the mixture at a concentration of more than about 0.01%. In still other embodiments, depending on the make-up of the biomass and the characteristics of the PHA, greater or lesser concentrations may also be used. Advantageously, a variety of types of biomass may be used, for example, one or more of methanotrophic, autotrophic, and heterotrophic biomass are used in several embodiments.

Also provided for herein is a method for the synthesis of a polyhydroxyalkanoate (PHA) in a biomass material, comprising the steps of: (a) providing a medium comprising a biomass capable of metabolizing a source of carbon, and (b) increasing the concentration of one or more nutrients in the medium to cause the biomass to synthesize PHA or increase the synthesis rate of PHA relative to the synthesis rate of non-PHA material.

Advantageously, a variety of types of biomass may be used, for example, one or more of methanotrophic, autotrophic, and heterotrophic biomass are used in several embodiments.

In several embodiments, the step of increasing the concentration of a nutrient in the medium causes a reduction in the rate of production of non-PHA biomass relative to the rate of production of the PHA in the biomass. This relative increase in efficiency (e.g., the reduction of metabolic resources spent producing non-PHA biomass) advantageously increases the PHA production capacity of the biomass material (e.g., by increasing the overall output, increasing the per unit biomass output or concentration).

In several embodiments, the nutrient is selected from the group consisting of: ethylenediaminetetraacetic acid (EDTA), citric acid, iron, copper, magnesium, manganese, zinc, chromium, nickel, boron, molybdenum, calcium, potassium, boron, methane, phosphorus, oxygen, nitrogen, carbon dioxide and combinations thereof.

There is also provided a method for the synthesis of a polyhydroxyalkanoate (PHA) in a biomass material, comprising the steps of: (a) providing a medium comprising a biomass and one or more nutrients, and (b) increasing the concentration of one or more of the nutrients in the medium to cause the biomass to metabolically synthesize PHA by using the biomass as a source of carbon for the production of the PHA. In several embodiments, the nutrient is selected from the group consisting of magnesium, iron, copper, zinc, nickel, chromium, phosphorus, oxygen, calcium, methane, carbon dioxide, hydroxyl ions, hydrogen ions, sulfate, nitrogen, and combinations thereof. Various types of biomass may be used, for example, one or more of methanotrophic, autotrophic, methanogenic and heterotrophic biomass are used in several embodiments Complementary to the methods, processes, and systems for PHA production, there is also provided herein a process for extracting a polyhydroxyalkanoate from a PHA-containing biomass slurry comprising PHA, non-PHA biomass, and a liquid, comprising: a) controlling the pressure and temperature of the liquid to cause the non-PHA biomass to become soluble in the liquid, and b) reducing the amount of the liquid in the slurry.

Depending on the embodiment, the liquid in the slurry may be one or more of methanol, water, carbon dioxide, or another a solvent, super critical fluid, polymer, additive, plasticizer, and/or other fluid (e.g., methylene chloride, acetone, methanol, sodium hypochlorite, hypochlorite, chloroform, or dichloroethane). Various pressures are used, depending on the embodiment, including pressure above atmospheric pressure and pressure below atmospheric pressure. In still additional embodiments, phases or sequential changes between sub-atmospheric and supra-atmospheric pressures are used. In conjunction with the pressure, temperatures may be varied, in some embodiments, ranging between 0 and 250 degrees Celsius. In other embodiments, a broader range of temperatures is used, for example −40 degrees Celsius to about 500 degrees Celsius, including about −20, about −4, about 4, about 20, about 37, about 100, about 150 about 200, about 300, or about 400 degrees Celsius. In one embodiment, the temperature is between 0 and 200 degrees Celsius and the pressure is between −30 mmHg and 30,000 psi. In several embodiments, temperatures are maintained between 0 and 400 degrees Celsius, 20 and 80 degrees Celsius, 10 and 100 degrees Celsius, 5 and 200 degrees Celsius, 100 and 200 degrees Celsius, or 0 and 300 degrees Celsius. In several embodiments, different combinations of temperature and pressure may be used, depending on the makeup of the slurry, the concentration of PHA in the slurry and other factors. Also depending on the characteristics of the slurry and other factors, the step of reducing the amount of the liquid in the slurry comprises reducing the amount of the liquid in the biomass slurry before, during, and/or after the step (a).

Reduction in the amount of the liquid can be achieved in a variety of ways, used either alone or in combination (e.g., sequentially) such as for example, centrifugation, filtration, distillation, spray drying, flash drying, lyophilization, air drying, and/or oven drying. These processes can reduce the amount of liquid in the slurry by about 0.1 to about 100%. In several embodiments, the reduction is over 50%, over 90%, or over 95%. Which method is chosen depends, in some embodiments, on the state of the slurry at that time. Some methods are more efficient at removal of liquid that others, and as such, may be better suited to slurries with a higher liquid content.

In some, embodiments, it may be necessary to increase the amount of liquid in the slurry (e.g., to effect a more efficient downstream step), which depending on the embodiment can be done before, during, and/or after the step (a). Various amounts of liquid may be added, depending on the embodiment, for example such that the solids concentration in the slurry of less than about 1 g/L, less than about 5 g/L, less than about 100 g/L, less than about 250 g/L, less than about 500 g/L, less than about 750 g/L, less than about 1000 g/L. or about 1300 g/L. In some embodiments, supercritical (SC) fluids, such as $SC-CO_2$ or SC-water are used to purify PHA, such that proteins and/or non-PHA materials are rendered at least partially solubilized in $SC-CO_2$, SC-water, high temperature or high pressure water, and/or mixtures thereof. In some embodiments, compatibilizing extraction agents may be used, such as non-PHA polymers that maintain miscibility with PHA and high solubility in SC-fluids, such that the PHA, miscible polymer, and SC-fluid produce a low viscosity solution allowing separation of PHA from non-PHA material.

There is also provided a method for improving the functional characteristics of a polyhydroxyalkanoate (PHA) material, comprising the steps of: (a) providing a PHA, a biomass, and a non-PHA polymer, (b) combining the PHA, the non-PHA polymer, and the biomass in a mixture to form a compound, (c) heating the compound to between about 100 degrees Celsius and about 250 degrees Celsius. Depending on the embodiment, the biomass is present in the mixture at a concentration of between about 0.1 and about 0.8%, between about 0.1 and about 20%, between about 0.1 and about 40%, between about 0.1 and about 60%, between about 0.1 and about 80%, and overlapping ranges thereof.

In several embodiments the biomass is methanotrophic biomass, while in other embodiments, the biomass is autotrophic biomass, heterotrophic biomass, in combination, alone or with methanotrophic and/or methanogenic biomass.

In several embodiments, the non-PHA polymer is one or more of the following: polypropylene, polyethylene, polystyrene, polycarbonate, acrylonitrile butadiene styrene, polyethylene terephthalate, polyvinyl chloride, fluoropolymers, liquid crystal polymers, acrylic, polyamide/imide, polyarylate, acetal, polyetherimide, polyetherketone, nylon, polyphenylene sulfide, polysulfone, cellulosics, polyester, polyurethane, polyphenylene oxide, polyphenylene ether, styrene acrylonitrile, styrene maleic anhydride, thermoplastic elastomer, ultra high molecular weight polyethylene, epoxy, melamine molding compound, phenolic, unsaturated polyester, polyurethane isocyanates, urea molding compound, vinyl ester, polyetheretherketone, polyoxymethylene plastic, polyphenylene sulfide, polyetherketone, polysulphone, polybutylene terephthalate, polyacrylic acid, cross-linked polyethylene, polyimide, ethylene vinyl acetate, styrene maleic anhydride, styrene-acrylonitrile, poly(methyl methacrylate), polytetrafluoroethylene (including PTFE that is modified to increase miscibility with a PHA, such as a PHB or PHBV, including PTFE with molecular weight between about 1 and about 5,000, about 1 and about 10,000, about 5 and about 50,000, or above about 50,000), polybutylene, (including polybutylene that is modified to increase miscibility with a PHA, such as a PHB or PHBV, including polybutylene with molecular weight between about 1 and about 5,000, about 1 and about 10,000, about 5 and about 50,000, or above about 50,000), polylactic acid (including polylactic acid that is modified to increase miscibility with a PHA, such as a PHB or PHBV, including PLA with molecular weight between about 1 and about 5,000, about 1 and about 10,000, about 5 and about 50,000, or above about 50,000), polyvinyl chloride (including polyvinyl chloride that is modified to increase miscibility with a PHA, such as a PHB or PHBV, including PVC with molecular weight between about 1 and about 5,000, about 1 and about 10,000, about 5 and about 50,000, or above about 50,000), polyvinyl acetate (including polyvinyl acetate that is modified to increase miscibility with a PHA, such as a PHB or PHBV, including PVAc with molecular weight between about 1 and about 5,000, about 1 and about 10,000, about 5 and about 50,000, or above about 50,000), polyvinyl acetate co-polyvinylpyrrolidone (including Polyvinyl acetate co-Polyvinylpyrrolidone that is modified to increase miscibility with a PHA, such as a PHB or PHBV, including Polyvinyl acetate co-Polyvinylpyrrolidone with molecular weight between about 1 and about 5,000, about 1 and about 10,000, about 5 and about 50,000, or above about 50,000), polyvinylpyrrolidone (including Polyvinylpyrrolidone that is modified to increase miscibility with a PHA, such as a PHB or PHBV, including Polyvinylpyrrolidone with molecular weight between about 1 and about 5,000, about 1 and about 10,000, about 5 and about 50,000, or above about 50,000), polyvinyl alcohol (including Polyvinyl alcohol that is modified to increase miscibility with a PHA, such as a PHB or PHBV, including Polyvinyl alcohol with molecular weight between about 1 and about 5,000, about 1 and about 10,000, about 5 and about 50,000, or above about 50,000), cellulose, lignin, cellulose acetate butryate, polypropylene, polypropylene carbonate, propylene carbonate, polyethylene, ethyl alcohol, ethylene glycol, ethylene carbonate, glycerol, polyethylene glycol, pentaerythritol, polyadipate, dioctyl adipate, triacetyl glycerol, triacetyl glycerol-co-polyadipate, tributyrin, triacetin, chitosan, polyglycidyl methacrylate, polyglycidyl methacrylate, oxypropylated glycerine, polyethylene oxide, lauric acid, citric acid, trilaurin, citrate esters, triethyl citrate, tributyl citrate, acetyl tri-n-hexyl citrate, saccharin, boron nitride, thymine, melamine, ammonium chloride, talc, lanthanum oxide, terbium oxide, cyclodextrin, organophosphorus compounds, sorbitol, sorbitol acetal, sorbitol-based nucleating agent, sorbital-like nucleating agent, sodium benzoate, clay, nanoclay, calcium carbonate (including calcium carbonate that is included at various particle sizes or particle distribution sizes, including calcium carbonate that is included at very small particle size and optionally introduced at various points in an extrusion process, including (but not limited to) mostly at the beginning, middle, or end, to minimize the processing time of the calcium carbonate), sodium chloride, titanium dioxide, metal phosphate, glycerol monostearate, glycerol tristearate, 1,2-hydroxystearate, cellulose acetate propionate, polyepichlorohydrin, polyvinylphenol, polymethyl methacrylate, polyvinylidene fluoride, polymethyl acrylate, polyepichlorohydrin-co-ethylene oxide, polyvinyl idene chloride-co-acrylonitrile, polycyclohexyl methacrylate, cellulose acetate butryate, cellulose, starch, cellulose acetate butyrate-g-polyethyelene glycol, polyvinylidene chloride co-acrylonitrile, polyvinyl acetate, polyethylene glycol b-poly(e-caprolactone), R-PHB-OH, S-PHB-OH, polyphenol poly(4,4'-dihydroxydiphenyl ester, 4-tert-butylphenol, polyglutamate, acrylonitrile-butadiene-styrene, polystyrene, styrene acrylonitrile, polyethylene 2,6-naphtalate, polypropylene oxide, polyethylene terepthalate, polybutylacrylate, poly-y-benzyl-1-glutamate, starch-b-PPG-urethane, ethylene propylene rubber-g-sodium acrylate EPR-g-SA, polypropylene carbonate, polypropylene carbonate-co-polyvinyl acetate, natural starch, starch adipate, starch-b-polyester-urethane, starch-b-PEG-urethane, PHBV, polycaprolactone, PLLA, polyoxymethylene, polyvinyl acetate-co-vinyl alcohol, ethylene-propylene rubber, ethylene-vinyl-acetate copolymer, synthetic poly3-hydroxybutyrate, poly-3-hydroxybutyrate-co-poly-3-hydroxyvalerate, poly-3-hydroxypropionate, polybutylene succinate-co-butylene adipate, polybutylene succinate-co-caprolactone, phenol poly(4,4'-dihydroxydiphenyl ester, and/or polyvinylidene chloride.

There is also provided, in several embodiments, a method for the synthesis of polyhydroxyalkanoate (PHA) in a biomass material, comprising providing a medium comprising a biomass metabolizing a source of carbon, and increasing or maintaining above a minimum, the concentration of an element in the medium to cause the biomass to synthesize PHA and/or increase the synthesis rate of PHA relative to the synthesis rate of non-PHA material. In several embodiments the PHA is polyhydroxybutyrate (PHB), while in other embodiments other types of PHA are produced. In several embodiments, the biomass is one or more microorganisms. In one embodiment, the biomass comprises one or more recycled microorganisms (e.g., those that have already been processed through a PHA synthesis process). In one embodiment, the microorganisms have been processed to remove at least a portion of the PHA they produced in the prior synthesis process.

In several embodiments, the increase in the concentration of an element in the medium above a minimum concentration (or maintenance above that minimum) causes a reduction in the concentration or production of sugar, lipids, nucleic acids, saccharides, polysaccharides, methanobactin, and/or pigments in the biomass relative to the concentration or production of PHA in the biomass. In several embodiments, the element that is increased or maintained is one or more of phosphorus, oxygen, or nitrogen. In additional embodiments, the element is one or more of EDTA, citric acid, iron, copper, magnesium, manganese, zinc, calcium, potassium, boron, methane, or carbon dioxide.

In still additional embodiments, the PHA synthesis rate is increased relative to the synthesis rate of PHA in the biomass in the absence of the increase or maintenance above a minimum the concentration of an element in the medium.

There is also provided a method for the synthesis of polyhydroxyalkanoate (PHA) in a biomass material, comprising the steps of: (a) providing a medium comprising a biomass and an element, and (b) maintaining above a minimum concentration or increasing the concentration of the element in the medium to cause the biomass material to metabolically synthesize PHA at the expense of alternative biomass energy and/or carbon storage materials.

In several embodiments, the element that is increased (or maintained) is one or more of phosphorus, oxygen, magnesium, calcium, copper, iron, methane, carbon dioxide, hydroxyl ions, hydrogen ions, or nitrogen. In some embodiments, the amount of increase (or maintenance) that is required of one element is altered when more than one element is manipulated. For example, if phosphorous is increased in combination with another element, the overall amount of phosphorous needed is reduced as compared to the addition of phosphorous alone (e.g., the combination of elements potentiates the effect).

In several embodiments, the biomass comprises one or more microorganisms, such as for example, methanotrophic microorganisms, heterotrophic microorganisms, autotrophic microorganisms, methanogenic microorganisms, or combinations thereof.

More specifically, certain embodiments of the invention provide high efficiency, high density, high PHA concentration processes for the production of PHA from carbon-containing gases, comprising the steps of: (a) providing a microorganism culture comprising PHA-containing biomass, (b) removing a portion of the PHA-containing biomass from the culture, (c) extracting a portion of PHA from the removed culture to produce isolated PHA and PHA-reduced biomass, (d) purifying the isolated PHA, and (e) returning the PHA-reduced biomass to the culture to cause the culture to convert the carbon within the PHA-reduced biomass into PHA. In several embodiments, carbon output from the system is wholly or substantially only in the form of PHA.

In several embodiments, a system for using a microorganism culture to convert a carbon-containing gas into PHA at high efficiencies is provided. Microorganisms are cultured using a combination of one or more carbon-containing gases and PHA-reduced biomass, or derivatives thereof, as sources of carbon to produce PHA-containing biomass. A portion of the PHA-containing biomass is then removed from the culture, and PHA is extracted from the removed PHA-containing biomass to create substantially PHA-reduced biomass and substantially isolated PHA.

Typically, PHA is present in the PHA-containing biomass of gas-utilizing microorganisms at concentrations in the range of about 5%-60%, and approximately 40-95% of the PHA-containing biomass is discarded from the system following PHA extraction. In some cases, PHA is present in gas-utilization microorganisms in the range of about 1-90%, including at about 1%, about 3%, about 5%, about 7%, about 10%, about 15%, about 20%, about 25%, about 30%, about 35%, about 40%, about 45%, about 50%, about 60%, about 70%, about 80%, or about 90%, and approximately 10-99% of the PHA-containing biomass is discarded from the system following PHA extraction, including about 99%, about 97%, about 95%, about 93%, about 90%, about 85%, about 80%, about 75%, about 70%, about 65%, about 60%, about 55%, about 50%, about 40%, about 30%, about 20%, or about 10% of the PHA-containing biomass. Rather than discarding the remaining, e.g., 40-95% of the PHA-reduced biomass, in one embodiment of the invention, the PHA-reduced biomass is returned back to the microorganism culture to be regenerated as PHA by a microorganism culture capable of utilizing PHA-reduced biomass, or a derivative thereof, as a source of carbon for PHA production, thereby creating a regenerative closed-loop polymerization system. By using PHA-reduced biomass as a source of carbon for PHA production in microorganisms growing as or in association with gas-utilizing microorganisms, PHA can be produced from carbon-containing gases at surprisingly and unexpectedly improved carbon, energy, and chemical efficiencies, since carbon from carbon-containing gases that would otherwise be discarded is regenerated as PHA in a microorganism culture, and microorganisms that produce PHA from carbon-containing gases at low concentrations (e.g., 5-60% PHA by weight, or less than 70% PHA by weight) can, in some embodiments, be utilized to produce PHA at significantly increased carbon-to-PHA efficiencies. In some embodiments, the regeneration step is repeated to form an essentially closed-loop system. Thus, in some embodiments, the carbon output from the system is at least about 1%, 5%, 10%, 20%, 30%, 40%, 50%, 60%, 70%, 80%, 90%, 95%, 99% (or more) PHA In other words, at least about 1%, 5%, 10%, 20%, 30%, 40%, 50%, 70%, 80%, 90%, 95%, 99% (or more) of the carbon entering the system is converted into PHA. In other embodiments, about 1-5%, about 5-10%, about 10-20%, about 20-30%, about 30%-40%, about 40%-50%, about 50%-60%, about 60%-70%, about 70%-80%, about 80%-90%, about 90%-95%, about 95%-99% (and overlapping ranges thereof) of the carbon entering the system is converted to PHA. By regenerating PHA-reduced biomass as PHA in a microorganism culture, the percentage of carbon from a carbon containing gas that is converted to PHA is at least 2-fold, 3-fold, 4-fold, 5-fold, 6-fold, 7-fold, 8-fold, 9-fold, 10-fold, or greater than systems that do not employ the regenerative or closed-loop system disclosed herein. In some embodiments, the regeneration (e.g., return and/or recycling of the PHA-reduced biomass) step is repeated at least 2, 3, 4, 5, 6, 7, 8, 9, or 10 (or more) times. In some embodiments, the regeneration step is repeated until at least 90% to 95% of the carbon input into the system is converted into PHA. In some embodiments, the regeneration step is repeated as many times as desired to reach a particular percentage conversion of carbon to PHA.

Several embodiments of the invention provide for the production of PHA from carbon-containing gases at previously unattainable energy, carbon, and chemical efficiencies by way of providing a microorganism culture capable of metabolizing the carbon within both a carbon-containing gas and PHA-reduced biomass, manipulating the conditions of the culture to cause the culture to produce PHA, removing a portion of PHA-containing biomass from the culture, extracting the PHA within the removed PHA-containing biomass to create substantially isolated PHA and substantially PHA-reduced biomass, returning the PHA-reduced biomass to the culture and contacting the PHA-reduced biomass with the culture to cause the culture to metabolize the carbon within the PHA-reduced biomass into PHA, and purifying the isolated PHA. Thus, an advantage of several embodiments of the invention is the production of PHA from carbon-containing gases at significantly improved energy, carbon, and chemical efficiencies.

The process according to several embodiments disclosed herein yields a range of surprising benefits over current gas-based PHA production technologies. To begin, whereas the cell density of gas-based fermentation processes is traditionally limited by the mass transfer or diffusion rates of one or more factors, such as light, oxygen, carbon dioxide, methane, or volatile organic compounds, several embodiments disclosed herein enable the generation of cell densities that significantly exceed cell densities attainable in other current practices (e.g., by more than 1%, 10%, 20%, 30%, 50%, 80%, 100% or more), and thereby enables cost-efficient system mixing, aeration, heat control, and dewatering. For example, current methane-based PHA production systems are known to be capable (based on cell morphology and mass transfer characteristics) of generating approximately 60 g/L of biomass with an overall PHA concentration of 55%, or 33 g/L PHA. In contrast, in several embodiments of the invention, cell densities of approximately 135 g/L with an overall PHA concentration of 70%, or 94.5 g/L PHA are generated in a methane-based PHA production system. In some embodiments, cell densities of approximately 10 g/L, 20 g/L, 30 g/L, 60 g/L, 75 g/L, 100 g/L, 125 g/L, 135 g/L, 150 g/L or greater are achieved. In some embodiments, overall PHA concentration in such cultures ranges from approximately 1% to 20%, 20% to 30%, 30% to 55%, 55% to 60%, 65% to 70%, 70% to 80%, 80% to 90%, or 95% or greater, (and overlapping ranges thereof) result. In several embodiments, such PHA concentration ranges represent significant, unexpected, and surprising improvements over traditional processes, e.g., processes that are limited to low cell densities and/or PHA concentrations.

As a non-limiting example of the impact of this improvement on energy efficiency, the energy required, on an energy input-to-PHA output basis, to aerate, mix, and dewater a 135 g/L solution with a PHA concentration of 70% by weight is 186% less than the energy required to aerate, mix, and dewater a 60 g/L microorganism solution comprising 40% PHA by weight. In several embodiments, variations in the energy efficiency gains based on the systems and processes disclosed herein may occur, depending on the culture conditions, the strain or organisms used, and the concentration and/or purity of an initial gas stream or other carbon source. In several embodiments, even modest increases in efficiency have substantial benefits. For example, the ability to efficiently use an input gas having a low carbon concentration that would not otherwise be useful in PHA production may prevent the release of such a gas into the environment and/or reaction of the gas with other atmospheric compounds, thereby reducing the adverse impact of the low carbon concentration gas on the environment (e.g., destruction of ozone, greenhouse gas emission, pollution, etc.).

Additionally, whereas current gas-based PHA production systems produce significant carbon losses as a result of the low PHA inclusion concentrations of gas-utilizing microorganisms (e.g., a significant portion of carbon and energy input is lost as biomass), several embodiments of the invention enable the generation of overall carbon input yield efficiencies approaching maximum substrate values; e.g., 100% carbon input-to-PHA yield, minus respiration and/or downstream processing losses. In some embodiments, at least 5%, at least 10%, at least 30%, at least 50%, at least 70%, or at least 90%, carbon input-to-PHA yield is achieved. It is one important advantage of several embodiments of the invention that maximum carbon yield efficiencies are unexpectedly and surprisingly generated in a PHA production system employing gas-utilizing microorganisms, and particularly, in some embodiments, in PHA production systems employing gas-utilizing microorganisms that produce low biomass and/or PHA inclusion densities.

In some embodiments, the microorganism culture is a mixed culture, comprising heterotrophic microorganisms, methanotrophic microorganisms, autotrophic microorganisms, bacteria, yeast, fungi, algae, or combinations thereof. In other embodiments, the microorganism culture may be one or more cultures (e.g., a plurality of cultures). In some embodiments, the cultures are grown in one or more bioreactors. In some embodiments, the bioreactors utilize one or more culture conditions, including both aerobic and anaerobic conditions. In some embodiments, the microorganism culture converts PHA-reduced biomass to methane in an anaerobic process and subsequently to PHA in an aerobic process, such that PHA-reduced biomass is first anaerobically metabolized to methane and then used as methane to produce biomass and PHA in a methanotrophic culture.

In several embodiments, at least part of the microorganism culture is a mixed culture capable of metabolizing carbon-containing gases, including methane, carbon dioxide, greenhouse gases, and/or various other volatile organic compounds, into biomass and/or PHA. In some embodiments, the microorganism culture comprises a two phase system of anaerobic and anaerobic/aerobic metabolism, whereby carbon-containing gas is produced in a first substantially anaerobic phase and subsequently converted into PHA in a second phase, wherein the microorganism culture in the first phase is substantially anaerobic and the culture in the second phase is either anaerobic or aerobic, wherein the two phases may be operated in one single vessel or in multiple vessels.

In some embodiments, at least one or more of the microorganisms are contacted with artificial and/or natural light during one or more steps of the methods disclosed herein.

In some embodiments, at least one of more of the microorganisms is contacted with dissolved oxygen during one or more steps of the methods disclosed herein.

In some embodiments, at least one of more of the microorganisms is cultured at atmospheric, sub-atmospheric, or above-atmospheric pressures.

In some embodiments, at least one of more of the microorganisms can utilize only a carbon-containing gas as a source of carbon.

In several embodiments, at least one or more of the microorganisms can utilize carbon derived from a PHA-reduced biomass as a source of carbon. In other embodiments, at least one or more of the microorganisms is a heterotrophic microorganism capable of converting PHA-reduced biomass into, carbon dioxide, oxygen, biomass, and/or PHA.

In several embodiments, at least one or more of the microorganisms are cultured using carbon derived from both a carbon-containing gas and a PHA-reduced biomass.

In some embodiments, the microorganism culture is a pure culture. In some embodiments, the cultures are maintained in semi-sterile or sterile conditions.

In some embodiments, the microorganism culture is a mixed, non-sterile culture, including a naturally equilibrating consortium of microorganisms.

In several embodiments, the microorganism culture is at least partially comprised of genetically engineered microorganisms.

In some embodiments, the microorganism culture is a mixed culture comprising a combination of naturally occurring and genetically engineered microorganisms.

In several embodiments, the PHA is removed from the microorganism culture by solvent extraction, including solvent extraction at temperatures ranging from 0° C. to 200° C. and at pressures ranging from −30 psi to 30,000 psi.

In several embodiments, the PHA is removed from the microorganism culture through the utilization of ketones, alcohols, and/or chlorinated solvents.

In several embodiments, the PHA is removed from the microorganism culture by hypochlorite digestion and/or chlorine-based solvent extraction.

In several embodiments, the PHA is removed from the microorganism culture by supercritical carbon dioxide extraction.

In several embodiments, the PHA is removed from the microorganism culture by protonic non-PHA cell material dissolution.

In several embodiments, the PHA is partially removed from the microorganism culture to create a PHA-rich phase and a PHA-poor phase.

In several embodiments, the PHA is removed from the microorganism culture to render the PHA substantially free of non-PHA material, including substantially 5%, 10%, 20%, 30%-40%, 40%-50%, 50%-60%, 60%-70%, 70%-80%, 80-90%, 90-99% or more pure PHA by weight.

In several embodiments, the PHA is removed from the microorganism culture by manipulating the pH of the microorganism culture.

In certain embodiments, at least one or more of the microorganisms are contacted with methane, carbon dioxide, oxygen, and/or a combination thereof.

In several embodiments, multiple culture vessels are employed, such that microorganism growth, PHA synthesis, PHA-reduced biomass metabolism, and PHA removal are carried out in separate vessels.

In other embodiments, microorganism growth, PHA-reduced biomass metabolism, and PHA synthesis occurs in a single vessel.

In still other embodiments, microorganism growth and PHA synthesis occur in a single vessel and PHA extraction is carried out in one or more separate vessels.

In several embodiments of the process as disclosed herein, PHA synthesis is regulated by manipulating, increasing, decreasing, maintaining below a maximum threshold, or maintaining above a minimum threshold the concentration of a material in the process, wherein the material is one or more of oxygen, methane, carbon dioxide, nitrogen, phosphorus, copper, iron, manganese, carbon, magnesium, potassium, cobalt, aluminum, sulfate, chlorine, boron, citric acid, and EDTA.

In several embodiments, the microorganism culture comprises one or more strains of microorganisms collectively capable of converting the carbon within a carbon-containing gas into cellular biomass and the carbon from cellular biomass or methane into PHA.

In several embodiments, the microorganisms are subjected to filtration, centrifugation, settling, and/or density separation.

In several embodiments, the isolated PHA and/or the PHA-reduced biomass is subjected to filtration, centrifugation, settling, and/or density separation.

In some embodiments, the processes disclosed herein further comprise washing the recovered PHA with water or other liquid-based agents or solvents to purify the PHA.

In several embodiments, the process further comprises oxidizing the recovered PHA to purify the PHA.

In several embodiments, the process further comprises drying the recovered PHA to remove volatiles such as water and/or one or more solvents.

In several embodiments of the invention, methods for the production of PHA are provided. In one embodiment, the method comprises: (a) providing a microorganism culture comprising PHA-containing biomass, (b) removing a portion of the PHA-containing biomass from the culture, (c) extracting a portion of the PHA from the removed PHA-containing biomass to produce isolated PHA and PHA-reduced biomass, (d) returning the PHA-reduced biomass to the culture to cause the culture to convert the carbon within the PHA-reduced biomass into PHA, and (e) purifying the isolated PHA.

In one embodiment, the microorganism culture utilizes the PHA-reduced biomass, or derivatives thereof, such as carbon dioxide, methane, or volatile organic acids, volatile fatty acids, volatile organic compounds, non-methane organic compounds, and one or more carbon-containing gas as a source of carbon. In one embodiment, the gas is selected from the group consisting of methane, carbon dioxide, volatile organic compounds, hydrocarbons, and combinations thereof. In one embodiment, the gas is derived from one or more sources from the group consisting of: landfills, wastewater treatment plants, power production facilities or equipment, agricultural digesters, oil refineries, natural gas refineries, cement production facilities, and/or anaerobic organic waste digesters.

In some embodiments, the carbon in the PHA-reduced biomass is derived from one or more gases from the group consisting of: methane, biogas, carbon dioxide, volatile organic compounds, natural gas, wastewater treatment methane and VOCs, and hydrocarbons.

In some embodiments, natural and/or artificial light is utilized to induce the metabolism of the carbon dioxide by the culture.

In some embodiments, the microorganism culture comprises one strain, or a consortium of strains, of microorganisms, including one or more microorganisms selected from the group consisting of: bacteria, fungi, yeast, and algae, and combinations thereof.

In some embodiments, the microorganism culture comprises one or more microorganisms from the group consisting of: methanotrophic microorganisms, carbon-dioxide utilizing microorganisms, anaerobic microorganisms, methanogenic microorganisms, acidogenic microorganisms, acetogenic microorganisms, heterotrophic microorganisms, autotrophic microorganisms, cyanobacteria, and biomass-utilizing microorganisms, and combinations thereof.

In some embodiments, at least a portion of the microorganism culture is naturally occurring. In some embodiments, at least a portion of the microorganism culture is genetically engineered. In some embodiments, naturally occurring and genetically engineered microorganisms are both used in the culture. As used herein, the term genetically engineered shall be given its ordinary meaning and shall also refer to microorganisms which have been manipulated to contain foreign (e.g., not from that microorganism) genetic material and/or foreign proteins. In certain embodiments, microorganisms are genetically manipulated to express one or more enzymes or enzymatic pathways useful in PHA production. In certain embodiments, microorganisms are genetically manipulated to express a marker, enzyme, or protein useful allowing the selective identification of the genetically engineered microorganisms.

In some embodiments, the microorganism culture is at least partially maintained under above-atmospheric pressure.

In some embodiments, the PHA-containing biomass includes one or more microorganism-derived materials selected from the group consisting of: intracellular, cellular, and/or extracellular material, including a polymer, amino acid, nucleic acid, carbohydrate, lipid, sugar, polyhydroxyalkanoate, chemical, and/or metabolic derivative, intermediary, and/or end-product. In some embodiments, the PHA-containing biomass includes one or more microorganism-derived materials selected from the group consisting of: methane, volatile organic compounds, carbon dioxide, and organic acids.

In one embodiment, the PHA-containing biomass contains less than about 95% water, including less than about 90%, about 85%, about 80%, about 75%, or about 70% water.

In some embodiments, the PHA-containing biomass is mixed with one or more chemicals, including one or more chemicals from the group consisting of: methylene chloride, acetone, ethanol, methanol, ketones, alcohols, chloroform, and dichloroethane, or combinations thereof.

In one embodiment, the PHA-containing biomass is processed through homogenization, heat treatment, pH treatment, enzyme treatment, solvent treatment, spray drying, freeze drying, sonication, and microwave treatment, or combinations thereof.

In one embodiment, the PHA-reduced biomass includes the PHA-containing biomass wherein at least a portion of the PHA has been removed from the PHA-containing biomass. In another embodiment, the PHA-reduced biomass includes methane, carbon dioxide, and organic compounds produced from the PHA-reduced biomass.

In some embodiments, the PHA-reduced biomass is subject to dewatering, chemical treatment, sonication, additional PHA extraction, homogenization, heat treatment, pH treatment, hypochlorite treatment, microwave treatment, microbiological treatment, including both aerobic and anaerobic digestion, solvent treatment, water washing, solvent washing, and/or drying, including simple or fractional distillation, spray drying, freeze drying, and/or oven drying, or combinations thereof.

In several embodiments, the microorganism culture is maintained in a sterile, semi-sterile, or non-sterile environment.

In one embodiment, the PHA includes one or more PHA selected from the group consisting of: polyhydroxybutyrate (PHB), polyhydroxyvalerate (PHV), polyhydroxybutyrate-covalerate (PHB/V), polyhydroxyhexanoate (PHHx), and short chain length (SCL), medium chain length (MCL), and long chain length (LCL) PHAs.

In several embodiments, the metabolism, growth, reproduction, and/or PHA synthesis of the culture is controlled, manipulated, and/or affected by a growth medium. In some embodiments, the bioavailable and/or total concentration of nutrients within the growth medium, such as copper, iron, oxygen, methane, carbon dioxide, nitrogen, magnesium, potassium, calcium, phosphorus, EDTA, calcium, sodium, boron, zinc, aluminum, nickel, sulfur, manganese, chlorine, chromium, molybdenum, and/or combinations thereof are manipulated (e.g., increased, decreased, or maintained) in order to control the metabolism, growth, reproduction, and/or PHA synthesis of the culture In some embodiments, a single nutrient in the growth medium is manipulated, while in some embodiments, more than one nutrient in the growth medium is manipulated to achieve the desired effect on the culture. In several embodiments, manipulation of a nutrient (or other component of a culture medium) is performed, in several embodiments, in order to maintain the overall concentration of that nutrient in the medium over time within a certain desired range (e.g., if a nutrient is consumed by the microorganisms, a "replacement" amount of that nutrient is added to the medium).

In one embodiment, the conversion of the PHA-reduced biomass into the PHA is induced and/or controlled by manipulating the composition of the medium. As discussed herein, the conversion of PHA-reduced biomass into the PHA can be controlled in a time-dependent manner to maximize the efficiency of conversion. In some embodiments, conversion to PHA production is induced about 1-12 hours, about 5-15 hours, or about 8-24 hours after PHA-reduced biomass is re-introduced into the culture. In some embodiments, longer times, e.g., about 24 hours to several days or weeks, are employed.

In one embodiment, the conversion of the PHA-reduced biomass into the PHA is effected by manipulating the concentration one or more elements within a medium selected from the group consisting of: nitrogen, methane, carbon dioxide, phosphorus, oxygen, magnesium, potassium, iron, copper, hydrogen, hydrogen ions, hydroxyl, hydroxyl ions, sulfate, manganese, calcium, chlorine, boron, zinc, aluminum, nickel, and/or sodium, and combinations thereof.

Methods used in several embodiments disclosed herein to control the concentration of elements within the medium include, but are not limited to, automatic, continuous, batch, semi-batch, manual, injection, solid feed, liquid, or other methods of inputting one or more chemical into the medium, wherein the total and/or bioavailable concentration of elements is increased, decreased, maintained, adjusted, or otherwise controlled at one or more time and/or physical chemical adjustment points.

According to several embodiments, additional methods to adjust the total or bioavailable concentration of one or more elements within a mineral media include, but are not limited to, the directed precipitation, chelation, de-chelation, and de-precipitation of elements. In one embodiment, the directed precipitation or chelation of one or more element is utilized to reduce the total or bioavailable concentration of one or more element within a medium and thereby i) induce or increase PHA production in a biomass and/or ii) control the metabolism of microorganisms within a medium, including for the purpose of controlling the specification and/or functionality of PHA. In one embodiment, methanobactin is produced and/or utilized to chelate copper and/or iron in order to impact the metabolism of methanotrophic microorganisms.

In several embodiments, the concentration of one or more elements within a growth culture medium is increased, controlled, manipulated, or otherwise managed to induce or increase the rate of PHA production in biomass, including a microorganism culture. In one embodiment, the concentration of phosphorus within the medium is increased to induce or increase the rate of PHA production in a microorganism culture. In one embodiment, the concentration of an element, e.g., phosphorus, carbon dioxide, iron, copper, oxygen, methane, hydroxyl ions, hydrogen ions, and/or magnesium, within the medium is manipulated or increased to cause a metabolic shift in the microorganism culture, such that the production of non-PHA materials by the culture using carbon and/or nitrogen sources (e.g., nitrate, ammonia, ammonium, dinitrogen, urea, or amino acids) is reduced, inhibited, or otherwise impacted to enhance PHA production. In one embodiment, the concentration of phosphorus within the medium is manipulated or increased to reduce the utilization of nutrients, including nitrogen, oxygen, and/or carbon, for the production of non-PHA materials by the culture. In one embodiment, the concentration of phosphorus within the medium is manipulated or increased to reduce the utilization of nutrients for the production of non-PHA materials by the culture and induce or increase the rate of PHA production in the culture.

In several embodiments, an increase in the concentration of phosphorus causes a metabolic shift that favors the production of PHA at the expense of other non-PHA materials, including a reduction in the production of protein, nucleic acids, polysaccharides, sugars, methanobactin, lipids, particularly but not necessarily under growth-limiting conditions, including nitrogen (e.g., nitrate, ammonia, ammonium, dinitrogen, urea, or amino acids), oxygen, magnesium, potassium, iron, copper, or other nutrient-limiting conditions.

In several embodiments, depending on the strain of microorganism, an increase in the concentration of phosphorus above about 0.00 ppm, 0.01 ppm, 0.02 ppm, 0.05 ppm, 0.10 ppm, 0.20 ppm, 0.50 ppm, 1.00 ppm, 1.25 ppm, 1.50 ppm, 1.75 ppm, 2.00 ppm, 2.20 ppm, 2.40 ppm, 3 ppm, 4 ppm 5 ppm, 6 ppm, 8 ppm, 20 mM, 30 mM, 40 mM, 50 mM, 60 mM, 70 mM, 80 mM, 90 mM, 100 mM, 110 mM, 120 mM, 140 mM, 200 mM, 400 mM, 600 mM, 800 mM, or 1000 mM, or overlapping ranges between these concentrations, causes a reduction in the utilization of carbon and/or nitrogen sources for the production of non-PHA material, including proteins, non-PHA polymers, nucleic acids, lipids, pigments, polysaccharides, methanobactin, and/or carbon dioxide, and, under growth-limiting conditions, an increase in the utilization of carbon sources for the production of PHA material, as a result of metabolic changes in the culture and/or chemical interactions between chemicals within the media and/or culture induced by augmented concentrations of phosphorus. The elevation of phosphorus concentrations as a method to induce or increase the rate of PHA production in a biomass culture is contrary to the conventional wisdom in the field, which suggests that PHA production is induced or enhanced by reducing or eliminating the concentration of elements, such as, e.g., phosphorus in the mineral medium. The addition or controlled elevation of an element, such as, e.g., phosphorus to a biomass system to induce or increase PHA production produces an unexpected and surprising increase in PHA production in a biomass system. An element such as, e.g., phosphorus may be added to the mineral media using a variety of phosphorus sources, including phosphorus, phosphate, phosphoric acid, sodium phosphate, disodium phosphate, monosodium phosphate, and/or potassium phosphate, dissolved carbon dioxide, Fe(II) iron, Fe(III) iron, copper sulfate, Fe-EDTA, dissolved oxygen, dissolved methane, and/or magnesium sulfate, among other potential sources. In one embodiment, copper concentrations are manipulated or maintained above a minimum concentration, for at least a period of time, in order to reduce the concentration of methanobactin in the medium in order to increase the purity of PHA produced by and/or extraction from a methanotrophic microorganism culture.

In several embodiments of the invention, the concentrations of dissolved gases, such as methane, oxygen, carbon dioxide, and/or nitrogen, are manipulated to increase the rate of PHA production relative to the rate of cellular production of non-PHA materials and, specifically, to cause a reduction in the utilization of carbon or nitrogen sources for the production of non-PHA material, including proteins, non-PHA polymers, enzymes, nucleic acids, lipids, pigments, polysaccharides, methanobactin, and/or carbon dioxide, and, under some conditions, including growth-limiting conditions, further cause an increase in the utilization of carbon sources for the production of PHA material, as a result of metabolic changes in the culture and/or chemical interactions between chemicals within the media and/or culture induced by augmented concentrations of one or more of such dissolved gases. In one embodiment, the concentration of methane or dissolved methane is manipulated to above at least 0.01 ppm, 0.05 ppm, 0.1 ppm, 0.5 ppm, 1.0 ppm, 1.5 ppm, 1.75 ppm, 2.0 ppm, 2.5 ppm, 3.0 ppm, 3.5 ppm, 4.0 ppm, 4.5 ppm, 5.0 ppm, 6.0 ppm, 7.0 ppm, 8.0 ppm, 10 ppm, 15 ppm, 20 ppm, 30 ppm, 50 ppm, 100 ppm, 200 ppm, 300 ppm, 500 ppm, or 1000 ppm, or overlapping ranges between these concentrations to reduce the production of non-PHA materials relative to the production of PHA materials in a culture. In some embodiments, the concentration of oxygen or dissolved oxygen is manipulated to above at least 0.0001 ppm, 0.01 ppm, 0.05 ppm, 0.1, 0.2 ppm, 0.3 ppm, 0.4 ppm, 0.5 ppm, 0.6 ppm, 0.7 ppm, 0.8 ppm, 0.9 ppm, 1.0 ppm, 1.1 ppm, 1.2 ppm, 1.3 ppm, 1.4 ppm 1.5 ppm, 1.75 ppm, 2.0 ppm, 2.5 ppm, 3.0 ppm, 3.5 ppm, 4.0 ppm, 4.5 ppm, 5.0 ppm, 6.0 ppm, 7.0 ppm, 8.0 ppm, 10 ppm, 15 ppm, 20 ppm, 30 ppm, 50 ppm, 100 ppm, 200 ppm, 300 ppm, 500 ppm, 750 ppm, or 1000 ppm, or overlapping ranges between these concentrations to reduce the production of non-PHA materials relative to the production of PHA materials in a culture. In one embodiment, the concentration of carbon dioxide or dissolved carbon dioxide is manipulated to at least 0.01 ppm, 0.05 ppm, 0.1 ppm, 0.5 ppm, 1.0 ppm, 1.5 ppm, 1.75 ppm, 2.0 ppm, 2.5 ppm, 3.0 ppm, 3.5 ppm, 4.0 ppm, 4.5 ppm, 5.0 ppm, 6.0 ppm, 7.0 ppm, 8.0 ppm, 10 ppm, 15 ppm, 20 ppm, 30 ppm, 50 ppm, 100 ppm, 200 ppm, 500 ppm, 1000 ppm, 1500 ppm, 2000 ppm, 3000 ppm, 5000 ppm, 10,000 ppm, 20,000 ppm, or overlapping ranges between these concentrations to reduce the production of non-PHA materials relative to the production of PHA materials in a culture. In some embodiments, the concentration of nitrogen or dissolved nitrogen is manipulated to above at least 0.01 ppm, 0.05 ppm, 0.1 ppm, 0.5 ppm, 1.0 ppm, 1.5 ppm, 1.75 ppm, 2.0 ppm, 2.5 ppm, 3.0 ppm, 3.5 ppm, 4.0 ppm, 4.5 ppm, 5.0 ppm, 6.0 ppm, 7.0 ppm, 8.0 ppm, 10 ppm, 15 ppm, 20 ppm, 30 ppm, or 50 ppm or ranges between these concentrations to reduce the production of non-PHA materials relative to the production of PHA materials in a culture. In several embodiments, an increase in the concentration of methane, oxygen, carbon dioxide, and/or nitrogen causes a metabolic shift that favors the production of PHA at the expense of other non-PHA materials, including a reduction in the production of protein, nucleic acids, polysaccharides, sugars, and/or lipids, particularly, but not necessarily, under growth-limiting, that is, PHA synthesis, conditions.

In some embodiments, the PHA is at least partially removed from the PHA-containing biomass or otherwise purified using one or more extraction agents or mechanisms selected from the group consisting of: methylene chloride, acetone, ethanol, methanol, dichloroethane, supercritical carbon dioxide, sonication, homogenization, water, heat, distillation, spray drying, freeze drying, centrifugation, filtration, enzymes, polymers, surfactants, co-solvents, hydrolyzers, acids, bases, hypochlorite, peroxides, bleaches, ozone, EDTA, miscible agents, and/or combinations thereof.

In one embodiment, the extraction process is substantially carried out at intracellular temperatures less than 100° C. In other embodiments, temperatures for extraction range from about 10° C. to 30° C., from about 30° C. to 50° C., from about 50° C. to 70° C., from about 70° C. to 90° C., from about 90° C. to about 120° C., from about 100° C. to about 140° C., from about 20° C. to 150° C., or from about 120° C. to about 200° C., or higher. In another embodiment, cells are reused for polymerization following the extraction process as viable cells.

In some embodiments, PHA-containing biomass is treated with one or more chemical treatment steps to control, modify, or increase the concentration or functional characteristics (e.g., molecular weight, monomer composition, melt flow profile, purity, non-PHA residuals concentration, protein concentration, DNA concentration, antibody concentration, antioxidant concentration) of PHA in a PHA-containing material or biomass.

As used herein, the terms "functional properties" and "functional characteristics" shall be given their ordinary meanings and shall also refer to the specification, features, qualities, traits, or attributes of PHA. The functional characteristics of the generated PHA include, but are not limited to molecular weight, polydispersity and/or polydispersity index, melt flow and/or melt index, monomer composition, co-polymer structure, melt index, non-PHA material concentration, purity, impact strength, density, specific viscosity, viscosity resistance, acid resistance, mechanical shear strength, flexural modulus, elongation at break, freeze-thaw stability, processing conditions tolerance, shelf-life/stability, hygroscopicity, and color. As used herein, the term "polydispersity index" (or PDI), shall be given its ordinary meaning and shall be considered a measure of the distribution of molecular mass of a given polymer sample (calculated as the weight average molecular weight divided by the number average molecular weight). Advantageously, several embodiments of the processes disclosed herein may be carried out in sterile, semi-sterile, or non-sterile conditions. In several embodiments, consistency in more than one of these functional properties is achieved. For example, in some embodiments, consistent molecular weight, polydispersity, and combinations thereof are achieved. In one embodiment, temperature is used to control, modify, reduce, or optimize the molecular weight, polydispersity, melt flow, and other characteristics of PHA. In one embodiment, temperature and/or time is used to control the molecular weight of PHA between the range of about 5,000,000 and about 10,000 Daltons. In several embodiments the molecular weight of PHA ranges between about 5,000,000 and about 2,500,000 Daltons, between about 2,500,000 and about 1,000,000 Daltons, between about 1,000,000 and about 750,000 Daltons, between about 750,000 and about 500,000 Daltons, between about 500,000 and about 250,000 Daltons, between about 250,000 and about 100,000 Daltons, between about 100,000 and about 50,000 Daltons, between about 50,000 and about 10,000 Daltons, and overlapping ranges thereof. In one embodiment, a slurry comprising PHA-containing biomass and a culture media is subject to one or more water removal steps or water addition steps to increase the concentration of PHA in a PHA-containing biomass. In one embodiment, the water removal step is a dewatering step or combination of dewatering steps, such as centrifugation, filtration, spray drying, flash drying, and/or chemical dewatering (e.g., with acetone, ethanol, or methanol, or combinations thereof), wherein at least a portion of the water concentration relative to the concentration of PHA-containing biomass in the slurry is reduced. In one embodiment, a temperature and/or pressure control step is carried out under atmospheric (0 psi), sub-atmospheric (−100-0 psi), or above-atmospheric pressure (e.g., 0-30,000 psi) and at temperature conditions wherein the PHA-containing biomass, or the liquid in and/or around the PHA-containing biomass, is maintained, for at least a period of time, at a temperature ranging from −30 to 10 degrees Celsius, 10 degrees Celsius to 100 degrees Celsius, 10 degrees Celsius to 150 degrees Celsius, 20 degrees Celsius to 250 degrees Celsius, and/or 100 to 200 degrees Celsius, including overlapping ranges thereof. In one embodiment, the PHA-containing biomass is subject to a dewatering step before or after the temperature and/or pressure control step, wherein the dewatering step is centrifugation, filtration, and/or spray drying, to produce a fully or partially de-watered PHA-containing biomass or PHA-containing biomass slurry, wherein the water concentration of the dried slurry is less than 99%, 95%, 80%, 60%, 40%, 30%, 20%, 10%, 5%, 3%, 2%, or 1% water. In one embodiment, the PHA-containing biomass is subject to a temperature control step, wherein the water or liquid chemicals within and/or around the biomass is controlled and maintained at a temperature of at least −30, −10, −5, −4, −3, −2, −1, 0, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300 degrees Celsius or ranges between those temperatures. In one embodiment, the PHA-biomass is not dried prior to such temperature control step. In one embodiment, the PHA-containing biomass is dried or de-watered prior to such temperature control step. In one embodiment, the PHA-containing biomass is filtered or centrifuged following the temperature control step. In one embodiment, the PHA-containing cell slurry is not dewatered, for example, by centrifugation or other drying mechanism, prior to the temperature control step. In one embodiment, a mechanism to impart shear onto or into the PHA-containing biomass is coupled with a temperature control step; such shear may be imparted in the form of one or more shear induction mechanisms including, but not limited to e.g., a centrifugal pump, agitator, blender, high shear mixer, vortex mixer, etc. In one embodiment, the PHA-containing biomass is dewatered in one step and the treated PHA-containing biomass is further dewatered in one or more additional steps. In one embodiment, the PHA-containing biomass is dewatered, water and/or other chemicals are added and temperature and/or pressure is controlled, and the treated PHA-containing biomass is further dewatered and/or purified. In one embodiment, the water and/or chemicals within, around, and/or added to the PHA-containing biomass is temperature and/or pressure controlled, and the treated PHA-containing biomass is further purified in one or more purification steps. In one embodiment, the temperature control step process time is approximately 1 second, 5 seconds, 10 seconds, 25 seconds, 60 seconds, 2 minutes, 5 minutes, 20 minutes, 45 minutes, 1 hour, 2 hours, 5 hours, 6 hours, 7 hours, 12 hours, 15 hours, 24 hours, 36 hours, or 48 hours, or ranges between those times. In one embodiment, inorganic materials may be used to effect PHA modification, purification, or extraction, including carbon dioxide and dinitrogen. In one embodiment, the PHA-containing slurry or biomass is treated with carbon dioxide under elevated temperatures and pressures, including supercritical ranges, to induce PHA extraction or functional modification of PHA. In one embodiment, solvents, including methylene chloride, enzymes, super critical fluids, acetone, chloroform, dichloroethane, ethanol, plasticizers, acids, bases, polymers, and/or methanol are used, alone or in combination, in conjunction with any of the above steps to improve efficiency, including increasing purity, recovery, extractability, solubility, reaction speed, odor, color, recyclability, biodegradability, toxicity, endotoxin removal rate, and the like. In one embodiment, solvents or extraction materials may be used or recycled for biomass production, biogas production, and/or PHA synthesis.

In one embodiment, chemicals are added to a PHA-containing biomass to cause the crystallization of PHA. In one embodiment, methylene chloride, carbon dioxide, acetone, water, dichloroethane, or methanol may be added to a PHA-containing biomass in order to induce the crystallization of PHA in the PHA-containing biomass. In some embodiments, this step may be useful for the downstream processing of PHA, wherein crystallized PHA is less prone than amorphous PHA to degradation, including molecular weight loss, when contacted with extraction chemicals, including solvents, enzymes, acids, bases, and bleach. In one embodiment, silicon, silica, derivatives thereof, and/or chemicals containing silicon may be added to the PHA-containing biomass in order to impact the metabolic status of the culture, and thereby control the functional characteristics of the PHA produced by the culture, including one or more of the following: molecular weight, monomer composition, co-polymer structure, melt index, and polydispersity.

In one embodiment, the removal of the PHA from the culture causes the culture to be temporarily deactivated, such that the culture, or elements thereof, may be further used for the synthesis of PHA. In certain embodiments, deactivation is beneficial because it allows for the delay of PHA production, transfer of material to another production area, and the like. In some embodiments, deactivation allows a tailored PHA production time frame. In some embodiments, the reuse of cells for polymerization is beneficial because it avoids or reduces the need to produce new biomass prior to polymerization, thereby reducing the carbon, chemical, and energy requirement of PHA production.

In one embodiment, a PHA produced according to the several embodiments described herein is provided.

In several embodiments, processes for the production of PHA from a carbon-containing gas are provided. In one embodiment, the process comprises the steps of: a) providing a growth medium comprising a microorganism culture capable of utilizing the carbon within one or more carbon-containing gas and PHA-reduced biomass, b) manipulating the medium to cause the culture to produce PHA, c) removing at least a portion of the PHA within the culture to create substantially isolated PHA and substantially PHA-reduced biomass, d) purifying the isolated PHA, and e) returning the PHA-reduced biomass to the culture to cause the culture to metabolize the carbon within the PHA-reduced biomass into PHA.

In one embodiment, the carbon-containing gas is selected from the group consisting of: methane, carbon dioxide, toluene, xylene, butane, ethane, methylene chloride, acetone, ethanol, propane, methanol, vinyl chloride, volatile organic compounds, hydrocarbons, and combinations thereof. As discussed herein, in some embodiments, non-gaseous carbon-containing material can be used, at least in part, for the production of PHA.

In one embodiment, the invention comprises manipulating the concentration of elements, e.g., copper, iron, phosphorus, oxygen, methane, carbon dioxide, in the culture medium to control the concentration of sMMO and/or pMMO produced by a methanotrophic culture in order to control the relative ratio of sMMO to pMMO in the culture, including over time and over multiple growth and polymerization cycles, and thereby control one or more of the growth conditions, metabolic status, metabolic disposition, and/or specification of PHA (e.g., molecular weight, polydispersity, melt flow, monomer composition, etc.) produced by the culture, including over time. In some embodiments, sMMO is expressed in a range between about 0% and 100% of a methanotrophic culture by dry cell weight, as a percentage of microorganisms expressing sMMO, or as a percentage of total MMO expressed by one or more methanotrophic cells, including between 0% and 1%, between about 1% and about 2%, between about 2% and about 3%, between about 3% and about 5%, between about 5% and about 10%, between about 10% and about 20%, between about 20% and about 30%, between about 30% and about 50%, between about 50% and about 70%, between about 70% and about 80%, between about 80% and about 90%, between about 90% and about 95%, between about 95% and about 100%, and overlapping ranges thereof. Simultaneously, or independently, in some embodiments, pMMO is expressed in a range between about 0% and 100% of a methanotrophic culture by dry cell weight, as a percentage of microorganisms expressing pMMO, or as a percentage of total MMO expressed by one or more methanotrophic cells, including between 0% and 1%, between about 1% and about 2%, between about 2% and about 3%, between about 3% and about 5%, between about 5% and about 10%, between about 10% and about 20%, between about 20% and about 30%, between about 30% and about 50%, between about 50% and about 70%, between about 70% and about 80%, between about 80% and about 90%, between about 90% and about 95%, between about 95% and about 100%, and overlapping ranges thereof. In some embodiments, the ratio of sMMO to pMMO produced in a methanotrophic culture is controlled to control the specification of PHA produced by a culture. In some embodiments, the relative weight ratio of sMMO to pMMO in a methanotrophic culture is at least or approximately 0 to 1, approximately 0.0000001 to 1, approximately 0.0001 to 1, approximately 0.001 to 1, approximately 0.01 to 1, approximately 0.1 to 1, approximately 1 to 1, approximately 2 to 1, approximately 3 to 1, approximately 5 to 1, approximately 10 to 1, approximately 15 to 1, approximately 20 to 1, approximately 25 to 1, approximately 30 to 1, approximately 35 to 1, approximately 50 to 1, approximately 65 to 1, approximately 70 to 1, approximately 80 to 1, approximately 90 to 1, approximately 95 to 1, approximately 98 to 1, approximately 99 to 1, approximately 100 to 1, approximately 1000 to 1, approximately 10,000 to 1, approximately 100,000 to 1, or approximately 1,000,000 to 1, respectively. In some embodiments, the relative weight ratio of pMMO to sMMO in a methanotrophic culture is approximately 0 to 1, approximately 0.0000001 to 1, approximately 0.0001 to 1, approximately 0.001 to 1, approximately 0.01 to 1, approximately 0.1 to 1, approximately 1 to 1, approximately 2 to 1, approximately 3 to 1, approximately 5 to 1, approximately 10 to 1, approximately 15 to 1, approximately 20 to 1, approximately 25 to 1, approximately 30 to 1, approximately 35 to 1, approximately 50 to 1, approximately 65 to 1, approximately 70 to 1, approximately 80 to 1, approximately 90 to 1, approximately 95 to 1, approximately 98 to 1, approximately 99 to 1, approximately 100 to 1, approximately 1000 to 1, approximately 10,000 to 1, approximately 100,000 to 1, or approximately 1,000,000 to 1.

In some embodiments, by controlling the relative concentrations of sMMO and pMMO produced by a culture of methanotrophic microorganisms, it is possible to control the metabolic status of the culture and thereby control the type (and characteristics) of PHA and other cellular material produced by the culture, particularly in the presence of one or more of the following: volatile organic compounds, fatty acids, volatile fatty acids, methanol, formate, acetone, acetate, acetic acid, formic acid, dissolved carbon dioxide, dissolved methane, dissolved oxygen, carbon-containing materials, ammonia, ammonium, and other elements or compounds that impact the metabolism of a culture of methanotrophic microorganisms in a certain manner according to the relative concentration of sMMO or pMMO in such a culture. In some embodiments, sMMO and/or pMMO is expressed in a range between about 0% and 100% of a methanotrophic culture by dry cell weight, as a percentage of microorganisms expressing sMMO or pMMO, or as a percentage of total MMO expressed by one or more methanotrophic cells, including between 0% and 1%, between about 1% and about 2%, between about 2% and about 3%, between about 3% and about 5%, between about 5% and about 10%, between about 10% and about 20%, between about 20% and about 30%, between about 30% and about 50%, between about 50% and about 70%, between about 70% and about 80%, between about 80% and about 90%, between about 90% and about 95%, between about 95% and about or 100%, and overlapping ranges thereof prior to, during, throughout, or after a PHA production phase.

In one embodiment, sMMO is not expressed, or is expressed in low amounts (e.g., less than about 35%, about 25%, about 15%, about 5%, about 3% or about 1%), in a methanotrophic culture prior to, during, throughout, or after a PHA production phase. In some embodiments, the directed or controlled absence or reduction of sMMO in a methanotrophic culture producing PHA, particularly in the presence of non-methane organic compounds that can be metabolized by methanotrophic microorganisms, engenders PHA production stability, consistency, and control by selectively shielding against the metabolism of one or some or many non-methane organic compounds that might otherwise be metabolized in the presence of sMMO, which enables the metabolism of a larger group of non-methane compounds than pMMO. Similarly, in one embodiment, pMMO is not expressed, or is expressed in low amounts (e.g., less than about 35%, about 25%, about 15%, about 5%, about 3% or about 1%), in a methanotrophic culture prior to, during, throughout, or after a PHA production phase. In some embodiments, the directed or controlled absence or reduction of pMMO in a methanotrophic culture producing PHA, particularly in the presence of non-methane organic compounds that can be metabolized by methanotrophic microorganisms, engenders PHA production stability, consistency, and control by selectively inducing or promoting the metabolism of one or some or many non-methane organic compounds that might otherwise be metabolized using pMMO. Further, in some methanotrophic cultures, sMMO promotes PHA synthesis at high intracellular concentrations by reducing cellular production of non-PHA materials, particularly as compared to PHA synthesis using pMMO. By controlling the concentration of sMMO relative to pMMO in a methanotrophic microorganism culture in the presence of methane and/or non-methane organic compounds, including VOCs, volatile fatty acids, acetone, formate, ethane, propane, it is possible to control the specification or type of PHA produced by the culture, including the molecular weight, polydispersity, and other similar functional characteristics as disclosed herein. In some embodiments, it is preferable to maintain the concentration of copper in the culture media in order to promote sMMO production. In some embodiments, the production of sMMO in many, most, or substantially all of the methanotrophic cells enables the culture to produce more PHA when subject to a nutrient limiting step than would otherwise be produced if the relative ratio of pMMO in the culture was higher prior to the nutrient limiting step. In some embodiments, it is preferable to maintain the concentration of copper in the culture media in order to promote pMMO production. In some embodiments, the production of pMMO in many, most, or substantially all of the methanotrophic cells enables the culture to produce more PHA when subject to a nutrient limiting step than would otherwise be produced if the relative ratio of sMMO in the culture was higher prior to the nutrient limiting step. In one embodiment, one or more methanotrophic cells or cultures are subject to repeated growth and PHA synthesis cycles or steps, wherein the relative concentration of sMMO to pMMO in the cells or cultures is controlled or caused to remain approximately similar or substantially the same (e.g., within about 5% to about 10%, with about 10% to about 20%, within about 20% to about 30%, within about 30% to about 40%, within about 40% to about 50%, within about 50 to about 75%) or the same in each new cycle or step in order to control or keep substantially the same (e.g., within about 5% to about 10%, with about 10% to about 20%, within about 20% to about 30%, within about 30% to about 40%, within about 40% to about 50%, within about 50% to about 75% across production runs) the specification, characteristics, and/or functionality (e.g., molecular weight, monomer composition, melt flow index, polydispersity, non-PHA material concentration, and/or purity) of the PHA produced by or extractable from the culture or cultures in each new or repetitive cycle with the same or new cells.

In one embodiment, the invention comprises a PHA comprising carbon derived from PHA-reduced biomass, wherein the PHA-reduced biomass comprises carbon derived from one or more carbon-containing gasses and/or one or more additional sources of carbon (either gaseous or non-gaseous). In one embodiment, PHA is co-mingled and/or melted with PHA-reduced biomass to improve the functional characteristics of the PHA. In one embodiment, PHA is co-mixed and/or melted with PHA-removed biomass and/or microorganism biomass to improve the functional characteristics of PHA. In one embodiment, the percentage of non-PHA microorganism biomass included in a PHA, PHA compound, or PHA mixture is about 0.00001% to about 0.001%, about 0.001% to about 0.01%, about 0.01% to about 0.1%, to about 0.1% to about 0.5%, about 0.5% to about 1%, about 1%, to about 2%, about 2% to about 3%, about 3% to about 5%, about 5% to about 7%, about 7% to about 10%, about 10% to about 15%, about 15% to about 20%, about 20% to about 30%, about 30% to about 40%, about 40% to about 50%, about 50% to about 60%, about 60% to about 70%, about 70% to about 80%, about 80% to about 90%, about 90% to about 98%, about 98% to about 99.99%, and overlapping ranges thereof. In some embodiments, the inclusion of microorganism biomass to a PHA improves the functional characteristics of a PHA by acting as one or more of the following: nucleating agent, plasticizer, compatibilizer, melt flow modifier, mold release agent, filler, strength modifier, elasticity modifier, or density modifier. In some embodiments, the microscopic size of microorganism biomass, including nucleic acids and proteins, is particularly and surprisingly effective as a functionalization agent for PHA. In some embodiments, microorganism biomass acts as a surprisingly effective compatibilizer for PHA and non-PHA polymers, such as polypropylene and polyethylene. In one embodiment, the biomass is subject to a processing and/or modification step in order to make the biomass, or at least a portion of the biomass, miscible with the PHA and/or non-PHA polymer, which yields unexpected and surprising functional improvement of the biomass as a blend component. Such processing/modification step may include: heat, shear, pressure, solvent extraction, washing, filtration, centrifugation, sonication, enzymatic treatment, super critical material treatment, cellular dissolution, flocculation, acid and/or base treatment, drying, lysing, and/or chemical treatment, wherein said chemicals may include solvents, cell dissolution agents, cell metabolizing agents, polymers, plasticizers, compatibilization agents, nucleating agents, including processing or modification steps that enable PHA contained in said biomass to become miscible with said biomass and/or other materials, including a second polymer or carrier agent. In one embodiment, there is provided a method for modifying the functional characteristics of a polyhydroxyalkanoate (PHA) material, comprising the steps of: (a) providing a PHA and a biomass, (b) subjecting the PHA and/or the biomass to a processing and modification step wherein the PHA and the biomass are subject to temperatures between at least about 20 degrees Celsius and about 250 degrees Celsius and to pressures of at least between about 1 atmosphere and about 350 atmospheres, thereby causing the modified biomass to effect a functional modification of the PHA material, wherein the functional modification comprises an increase in plasticization, nucleation, compatibilization, melt flow modification, strengthening, and/or elasticization. In one embodiment, the ratio of biomass to PHA in said PHA material may be between about 1:1000 and about 1000:1, including between 1:1000 and 1:500, 1:500 and 1:100, 1:100 and 1:10, 1:10 and 1:9, 1:9 and 1:8, 1:8 and 1:5, 1:5 and 1:3, 1:3 and 1:1, 1:1 and 2:1, 2:1 and 5:1, 5:1 and 10:1, 10:1 and 100:1, 100:1 and 500:1, and 500:1 and 1000:1, or ratios overlapping with the above ranges. In one embodiment, the temperature, in degree Celsius, of the modification step may range from 20 to 40, 40 to 60, 60 to 80, 80 to 100, 100 to 120, 120 to 140, 40 to 200, 140 to 160, 160 to 180, 180 to 200, 200 to 220, 220 to 250, 250 to 300, 90 to 200, 140 to 220, and 50 to 400. In one embodiment, the pressure, pounds per square inch, of the modification step may range from −30 to 50,000, −30 to 0, 0 to 50, 0 to 3,000, 0 to 200, 0 to 10,000, 0 to 5,000, 0 to 20,000, 20,000 to 50,000, 10,000 to 40,000, 25,000 to 30,000, 0 to 500, 0 to 1000, 0 to 2,000, and 40,000 to 50,000. In one embodiment, the modification step may be used to eliminate the need for additional plasticization, nucleation, compatibilization, melt flow modification, strengthening, reduction of PHA crystallinity or rate of crystallization, increase in optical clarity, and/or elasticization. In one embodiment, microorganism biomass and/or modified biomass, as described above, is mixed with a PHA to modify one or more of the nucleation, plasticization, compatibilization, melt flow, density, strength, elongation, elasticity, mold strength, mold release, and/or bulk density characteristics of a PHA, which may be melted, extruded, film blown, die cast, pressed, injection molded, or otherwise processed. In one embodiment, PHA is partially or not removed from PHA-containing microorganism biomass prior to melt processing, e.g., extrusion, injection molding, etc. In one embodiment, non-PHA biomass parts or materials are caused to remain with PHA derived from a PHA-containing biomass in order to modify or control the functional characteristics of a PHA material. In one embodiment, PHA is present in PHA-containing biomass at a concentration ranging from 1-99.99999%, 1-99.99%, 1-99%, 5-99%, 10-99%, 20-99%, 30-99%, 50-99%, 70-99%, 80-99%, 90-99%, 95-99%, 98-99%, and overlapping ranges thereof. In one embodiment, PHA, microorganism biomass, and/or one or more non-PHA material, polymer, or thermoplastic are mixed, melted, or processed together. In one embodiment, the non-PHA polymer or material consists of one or more of the following solvents, cell dissolution agents, cell metabolizing agents, polymers, plasticizers, compatibilization agents, miscible agents, and nucleating agents: polypropylene, polyethylene, polystyrene, polycarbonate, acrylonitrile butadiene styrene, polyethylene terephthalate, polyvinyl chloride, fluoropolymers, liquid crystal polymers, acrylic, polyamide/imide, polyarylate, acetal, polyetherimide, polyetherketone, nylon, polyphenylene sulfide, polysulfone, cellulosics, polyester, polyurethane, polyphenylene oxide, polyphenylene ether, styrene acrylonitrile, styrene maleic anhydride, thermoplastic elastomer, ultra high molecular weight polyethylene, epoxy, melamine molding compound, phenolic, unsaturated polyester, polyurethane isocyanates, urea molding compound, vinyl ester, polyetheretherketone, polyoxymethylene plastic, polyphenylene sulfide, polyetherketone, polysulphone, polybutylene terephthalate, polyacrylic acid, cross-linked polyethylene, polyimide, ethylene vinyl acetate, polyvinyl chloride, polyvinyl acetate, polyvinyl acetate co-polyvinylpyrrolidone, polyvinylpyrrolidone, polyvinyl alcohol, cellulose, lignin, cellulose acetate butyrate, polypropylene, polypropylene carbonate, propylene carbonate, polyethylene, ethyl alcohol, ethylene glycol, ethylene carbonate, glycerol, polyethylene glycol, pentaerythritol, polyadipate, dioctyl adipate, triacetyl glycerol, triacetyl glycerol-co-polyadipate, tributyrin, triacetin, chitosan, polyglycidyl methacrylate, polyglycidyl methacrylate, oxypropylated glycerine, polyethylene oxide, lauric acid, trilaurin, citrate esters, triethyl citrate, tributyl citrate, acetyl tri-n-hexyl citrate, saccharin, boron nitride, thymine, melamine, ammonium chloride, talc, lanthanum oxide, terbium oxide, cyclodextrin, organophosphorus compounds, sorbitol, sorbitol acetal, sodium benzoate, clay, calcium carbonate, sodium chloride, titanium dioxide, metal phosphate, glycerol monostearate, glycerol tristearate, 1,2-hydroxystearate, cellulose acetate propionate, polyepichlorohydrin, polyvinylphenol, polymethyl methacrylate, polyvinylidene fluoride, polymethyl acrylate, polyepichlorohydrin-co-ethylene oxide, polyvinyl idene chloride-co-acrylonitrile, polycyclohexyl methacrylate, cellulose acetate butyrate, cellulose, starch, cellulose acetate butyrate-g-polyethyelene glycol, polyvinylidene chloride co-acrylonitrile, polyvinyl acetate, polyethylene glycol b-poly(e-caprolactone), R-PHB-OH, S-PHB-OH, polyphenol poly(4,4'-dihydroxydiphenyl ester, 4-tert-butylphenol, polyglutamate, acrylonitrile-butadiene-styrene, polystyrene, styrene acrylonitrile, polyethylene 2,6-napthalate, polypropylene oxide, polyethylene terephthalate, polybutylacrylate, poly-y-benzyl-1-glutamate, starch-b-PPG-urethane, ethylene propylene rubber-g-sodium acrylate EPR-g-SA, polypropylene carbonate, polypropylene carbonate-co-polyvinyl acetate, natural starch, starch adipate, starch-b-polyester-urethane, starch-b-PEG-urethane, PHBV, polycaprolactone, PLLA, polyoxymethylene, polyvinyl acetate-co-vinyl alcohol, ethylene-propylene rubber, ethylene-vinyl-acetate copolymer, synthetic poly3-hydroxybutyrate, poly-3-hydroxybutyrate-co-poly-3-hydroxyvalerate, poly-3-hydroxypropionate, polybutylene succinate-co-butylene adipate, polybutylene succinate-co-caprolactone, phenol poly(4,4'-dihydroxydiphenyl ester, styrene maleic anhydride, styrene-acrylonitrile, poly(methyl methacrylate), polytetrafluoroethylene, polybutylene. polylactic acid, polyvinylidene chloride, and/or other similar materials or combinations of these materials, including mold release agents, plasticizers, solvents, solvent-grafted polymer, salts, nucleating agents, cross-linking agents, filaments, water, antioxidants, compatibilizers, copolymers, peroxides, alcohols, ketones, polyolefins, chlorinated solvents, non-chlorinated solvents, aliphatic hydrocarbons, hydrophilic agents, hydrophobic agents, enzymes, PHA miscible agents, pigments, stabilizers, and/or rubbers. In several embodiments, the additional of one or more of such non-PHA polymer or material advantageously improves the post-production handling of PHA. In one embodiment, PHA, methanotrophic, autotrophic, and/or heterotrophic microorganism biomass, and a non-PHA polymer are mixed and melted together, including, in one embodiment, under elevated pressures ranging from about 1 to about 5000 atmospheres. In one embodiment, the concentration of non-PHA microorganism biomass in such a mixture ranges from 0.0001% to 90%, 0.1% to 30%, 0.1% to 10%, or 0.5% to 8%, and overlapping ranges thereof. In one embodiment, the concentration of methanobactin in PHA is controlled to modify the functional characteristics of the PHA, including color, odor, brittleness, flexibility, antioxidant activity, antiviral activity, and/or antibacterial activity. In one embodiment, reducing the concentration of methanobactin in the PHA reduces the brown or yellow shade of the PHA and increases the flexibility of the PHA. In another embodiment, increasing the concentration of methanobactin in the PHA increases the antimicrobial (e.g., antibacterial, antiviral) and/or antioxidant activity or potential activity or the PHA. In one embodiment, a method is provided for improving the functional characteristics of a PHA polymer through the melting and cooling of the PHA polymer in the presence of a dual-functionalizing biomass agent and a second polymer, comprising the steps of: (a) providing a first polymer, a biomass, and a second polymer, wherein the first polymer is a PHA, (b) subjecting the biomass to a processing step comprising heat, pressure, solvent washing, filtration, centrifugation, super critical solvent extraction, and/or shear, wherein the processing step renders at least a portion of the biomass miscible or more functionally compatible, including by reducing the particle size and/or molecular weight of at least a portion of the biomass, with the first polymer and the second polymer, (c) contacting the first polymer with the biomass and the second polymer to form a compound, (d) heating the compound to between 50 degrees Celsius and 250 degrees Celsius and/or adding pressure to the compound between about 1 and about 5000 atmospheres, and (d) causing the biomass to effect a functional modification of the first polymer, the second polymer, and/or the combination of the first polymer and second polymer, wherein the functional modification comprises plasticization, nucleation, compatibilization, melt flow modification, increased flexibility, reduced flexular modulus, reduced tensile modulus, increased impact strength, increased tensile modulus, increased flexular modulus, crystallinity reduction, crystallization rate reduction, increased speed of crystallization, strengthening, and/or elasticization.

In one embodiment, a PHA derived from a carbon-containing greenhouse gas, or greenhouse gas emission including methane, carbon dioxide, or combinations thereof, is provided. In some embodiments, use of such a gas is particularly advantageous, as it allows for the simultaneous production of PHA at lower energy costs and higher efficiencies, but also removes a portion of a destructive gas from the atmosphere, or prevents a destructive gas from entering the atmosphere. In some embodiments, processes and systems as disclosed herein are particularly well suited for use near sources of such gases (e.g., landfills, power production plants, anaerobic digesters, etc.) for onsite conversion of harmful gasses to a commercially valuable product.

In several embodiments, processes for the oxidation of methane are provided. In one embodiment, the process comprises: providing a culture of methanotrophic and autotrophic microorganisms, providing a growth culture medium comprising dissolved methane and carbon dioxide, and contacting the culture with light to cause the culture to convert the carbon dioxide into oxygen, whereby the culture utilizes the oxygen to oxidize the methane, thereby reducing or eliminating the need for an extraneous source of oxygen to drive methanotrophic metabolism.

In some embodiments, the light used to contact the culture is artificial light. In some embodiments, the light used to contact the culture is natural light. In other embodiments, combinations of natural and artificial light are used. In some such embodiments, wavelengths of artificial light are specifically filtered out or controlled such that the culture is exposed to a broader or more controlled overall spectrum of light (e.g., the sum of wavelengths of natural light and artificial light). In some embodiments, the source of light also functions to generate heat, which can be used to maintain optimal culture temperatures. In other embodiments, light input is regulated by time, such that specific cultures of autotrophic and/or heterotrophic microorganisms are selected for or optimized according to the duration and/or pattern of light injection (e.g., 0-12 or 12-24 hours light injection, 0-12 or 12-24 hours dark incubation, multi-second pulsation, etc.).

In one embodiment, the addition of light reduces the need for exogenous oxygen sources. While such embodiments provide an advantage in reducing costs of input materials, in some embodiments, an exogenous source of oxygen, including air, is added to the culture.

In some embodiments, the addition of autotrophic microorganisms to the culture impacts the metabolism of the culture. In such an embodiment, the timed and planned addition, activation, or metabolic enhancement of autotrophic organisms can be based on the desire for changing the rate of methane oxidation.

In some embodiments, a system is used for PHA production comprising providing i) a culture of autotrophic, methanotrophic, methanogenic, and/or heterotrophic microorganisms and ii) a first gas comprising carbon dioxide, methane, volatile organic compounds, oxygen, and/or other gas, whereby the culture of microorganisms are caused to used the first gas to generate a second gas comprising carbon dioxide, methane, oxygen, volatile organic compounds, and/or other gas, whereby the culture subsequently is caused to utilize the second gas for the generation of PHA, which can then be isolated and purified according to several embodiments disclosed herein. In some embodiments, the first gas can be methane, carbon dioxide, oxygen, or volatile organic compounds. In other embodiments, the second gas can be oxygen, methane, carbon dioxide, or other volatile organic compounds. In some embodiments, microorganisms can be used to convert carbon dioxide to biomass which can in turn be used to produce methane, which can be subsequently used to produce PHA. In other embodiments, microorganisms can be used to convert carbon dioxide to oxygen which can in turn be used to produce PHA. As disclosed herein, the products generated at each of these steps may be recycled (e.g., splitting a portion of the autotrophic culture and recycling it to generate additional biomass, generating reduced-PHA biomass and recycling it into the methanotrophic culture to generate additional biomass and additional PHA).

In several embodiments, processes for producing autotrophic microorganisms using only methane as a carbon input are provided. In one embodiment, the process comprises: adding methane, oxygen, and methane-utilizing microorganisms to a culture of autotrophic microorganisms, whereby the methane-utilizing microorganisms convert the methane into carbon dioxide, and whereby the autotrophic microorganisms utilize the carbon dioxide as a source of carbon, thereby reducing or eliminating the need for an extraneous source of carbon dioxide to drive autotrophic metabolism. In some embodiments, addition of methanotrophic and/or heterotrophic microorganisms to the culture impacts the metabolism of the autotrophic microorganisms. As discussed herein, the purposeful addition of such microorganisms at particular times allows for specific levels of control over the overall output and operation of the system.

In several embodiments, processes for oxidizing methane at low concentrations are provided. In one embodiment, the process comprises: culturing methanotrophic microorganisms in a medium comprising water, dissolved methane, dissolved oxygen, and mineral salts, adding methanol to the medium at a rate and volume sufficient to cause the microorganisms to reduce the concentration of the methane in the medium, whereby substantially all of the methane within the medium is utilized, thereby enabling methanotrophic microorganisms to metabolize methane present at low bioavailable concentrations. In some embodiments, gas containing less than 20% methane by volume is contacted with the medium. In some embodiments, gas containing less than 1% methane by volume is contacted with the medium. In some embodiments, the methanol is produced by microorganism metabolism.

In several embodiments, processes for separating water from microorganism biomass are provided. In one embodiment, the process comprises: providing biomass mixed with water in a liquid medium, mixing the medium with a liquid agent selected from the group consisting of ketones, alcohols, chlorinated solvents, derivatives thereof, or combinations thereof, and subjecting the mixture to a filtration step. In several embodiments, this enables the efficient separation of biomass from water. In some embodiments, such methods reduce or eliminate the need for centrifugation in the separation process. In some embodiments, the liquid agent is acetone, ethanol, isopropanol, and/or methanol. In other embodiments, other liquid agents that are miscible with water are used to separate the biomass from the aqueous portion of the mixture. In several embodiments separation is achieved by centrifugation (high-speed, low-speed), gravity separation, multi-stage filtration, or combinations thereof.

In several embodiments, processes for extracting a polyhydroxyalkanoate from a PHA-containing biomass are provided. In one embodiment, the process comprises the steps of: (a) providing a PHA-containing biomass comprising PHA and water, (b) mixing said biomass with a solvent at a temperature sufficient to dissolve at least a portion of said PHA into said solvent and at a pressure sufficient to enable substantially all or part of said solvent to remain in liquid phase, thereby producing a PHA-lean biomass phase and a PHA-rich solvent phase comprising water, PHA and solvent (c) separating said PHA-rich solvent phase from said PHA-lean biomass phase at a temperature and pressure sufficient to enable substantially all or part of said solvent to remain in liquid phase and prevent substantially all or part of said PHA within said PHA-rich solvent phase from precipitating into said water, (d) reducing the pressure or increasing the temperature of said PHA-rich solvent phase to cause said PHA-rich solvent to vaporize and said PHA to precipitate or otherwise become a solid PHA material while maintaining the temperature and/or pressure of the PHA-rich solvent phase to prevent all or part of the temperature-dependent precipitation of said PHA into said water, and (e) collecting said solid PHA material, including optionally separating said solid PHA material from said solvent and/or said water.

In some embodiments, solvents include acetone, ethanol, methanol, dichloroethane, and/or methylene chloride. Depending on the solvent selected, in some embodiments, separating the solid PHA material from solvent and/or water is achieved by increasing the temperature of the mixture. In other embodiments, separation is achieved through reducing the pressure of the solvent, PHA, and/or water. In some embodiments, combinations of temperature changes and pressure changes are used to optimally separate solid PHA material from solvent and/or water. In some embodiments, evaporation of solvent and/or water occurs in a rapid fashion, thereby reducing the need for temperature or pressure changes. Advantageously, certain embodiments of the processes disclosed herein may optionally be carried out in a batch, semi-continuous, or continuous manner. Thus, the process can be tailored to the needs of the producer at any given time.

In several embodiments, processes for modifying the functional characteristics of a PHA are provided. In one embodiment, the process comprises providing a first PHA and a second PHA, wherein the molecular weight of said second PHA is greater than the molecular weight of said first PHA, and combining said first PHA with said second PHA to modify the functional characteristics of both said first PHA and second PHA. In some embodiments, both the first PHA and the second PHA are PHB, and in some embodiments, one or more of the first and second PHA comprises PHBV. In one embodiment the first PHA and the second PHA is PHB or PHBV.

In some embodiments, the molecular weight of the first PHA is greater than about 500,000 Daltons and the molecular weight of the second PHA is less than about 500,000 Daltons. However, in some embodiments, the molecular weight can be adjusted. For example, in some embodiments, a first PHA is subjected to a temperature sufficient to reduce the molecular weight of the first PHA. Thereafter, it can be combined with the second PHA. In several embodiments, the second PHA could also optionally be exposed to temperature in order to adjust its molecular weight. In some embodiments, the molecular weight of the second PHA is greater than about 800,000 Daltons. In certain embodiments, the molecular weight of said second PHA is greater than about 1,000,000 Daltons. In some embodiments, the molecular weights of the first and second PHA are specifically tailored relative to one another, (e.g., a ratio of 1:2, 1:4, 1:6, 1:8, 1:10, etc.) in order to maximize the alterations in functional characteristics.

In several embodiments, processes for increasing the penetration depth of light in a liquid are provided. In one embodiment, the process comprises the steps of (a) directing light into a liquid medium in the form of a light path and (b) reducing the density of liquid in the light path.

In several embodiments, the density of the liquid in the light path is reduced by adding gas to said liquid in the light path. In some embodiments, the gas is air, oxygen, methane, carbon dioxide, nitrogen, and/or a combination thereof. In some embodiments, the gas is simultaneously added along with the light. In certain embodiments, the gas and the light are emitted or injected into the liquid through a common material, such as a permeable or semi-permeable membrane through which light and/or gas traverse. In other embodiments, the light and the gas are added separately. In such embodiments, customization of the addition is possible. For example, gas can be added in pulses (e.g., on/off sequences), continuously, or in bracketed time frames around the addition of light. In some embodiments, the addition of light and gas are coordinated to maximize the penetration of the light. For example a burst of gas followed by a burst of light (or overlapping to some degree) may advantageously increase the penetration of the light.

In several embodiments, processes for modifying the pH in a microorganism culture medium are provided. In one embodiment, the process comprises the steps of: (a) providing a culture medium comprising water and microorganisms, (b) adding a first source of nitrogen to the medium to cause the microorganisms to metabolize the nitrogen and thereby increase the concentration of either hydroxyl ions or protons, respectively, in the medium, and/or (c) adding a second source of nitrogen to the medium to cause the microorganisms to metabolize the nitrogen and thereby increase the concentration of either protons or hydroxyl ions, respectively, in the medium. In other embodiments, a source of nitrogen is added to the culture that increases the pH of the medium, wherein the metabolism of the nitrogen source causes the pH of the medium to decrease, thereby reducing or eliminating the need for an additional pH adjustment step. In one embodiment, nitrogen fixation is used to add hydroxyl ions to the culture medium, which may or may not be counterbalanced by the addition of protons from either biological or chemical sources. In one embodiment, nitrate fixation is used to add hydroxyl ions to the culture medium, which may or may not be counterbalanced by the addition of protons from either biological or chemical sources. In one embodiment, ammonia or ammonium fixation is used to add protons to the culture medium, which may or may not be counterbalanced by the addition of hydroxyl ions from either biological or chemical sources.

In several embodiments, low shear processes for adding gas to a microorganism culture medium are provided. In one embodiment, the process comprises the steps of: (a) providing a liquid medium and a gas, (b) contacting the medium with the gas in a first container to cause at least a portion of the gas to dissolve in the medium, (c) providing a second container, and (d) transferring at least a portion of the liquid comprising the gas within the first container to the second container. In some embodiments, a mixer is also provided, in order to dissolve a portion of the gas in the medium. In some embodiments, the mixer is a pump or agitator or high shear mixer. In some embodiments, the mixer comprises a centrifugal pump. In still other embodiments, the gas itself provides a mixing function. For example, the injection of gas (via previously existing gas injection methods, including gas injection methods which do not require the use of a gas compressor, such as a vacuum induction system) into a medium will result in gas bubbles, which, if released at the bottom of a container comprising medium, will not only promote the dissolution of gas into the medium, but mix the medium as the bubbles rise.

In several embodiments, processes for injecting gas into a pressurized microorganism culture vessel are provided. In one embodiment, the process comprises the steps of: providing a vessel comprising a medium comprising microorganisms, adding a gas into the vessel that can be metabolized by the microorganisms, and adjusting the flow rate of the gas into the vessel according to the rate of change of pressure within the vessel. In some embodiments, the gas is oxygen, methane, carbon dioxide, or combinations thereof. Choice of the gas depends on the vessel used and the culture within the vessel. In some embodiments, backpressure monitoring allows for optimal gas injection for a given culture (e.g., if certain cultures react more quickly to administration of a gas and rapidly increase pressure, flow can be coordinately reduced).

In one embodiment, a process for producing light in a liquid medium is provided. In one embodiment, the process comprises the steps of: a) providing a liquid, b) providing a light-emitting unit or material comprising two conductive leads and a light-emitting conjuncture between the conductive leads, or a material that will emit light when contacted with electrons and c) inducing a voltage in the liquid, thereby inducing the movement of electrons in the conductive leads of the light-emitting unit or inducing electrons to contact the material, thereby causing the light-emitting unit or material to emit light. In some embodiments, the material is a phosphor, phosphoric, and/or luminescent material, including an electroluminescent phosphor.

In one embodiment, AC voltage is induced in a liquid by inserting the two leads of a 115V AC power source into a liquid. Without being bound by theory, it is believed that a liquid carrying an AC voltage is capable of inducing the movement of electrons into and through a light-emitting device suspended in the liquid and not contacting the two 115V AC power source leads due to the oscillating nature of electrons in an AC circuit, such that AC voltage in a liquid causes electrons to fill conductive paths connected to the liquid, in spite of the resistance of the conductive paths relative to the liquid, and will oscillate as an AC current in those conductive paths, thereby performing work, e.g., generating light in a light emitting diode. As a non-limiting example, light is produced in a liquid medium by a) placing a light-emitting diode in a liquid comprising water and electrolytic ions, and b) inducing an AC voltage in the liquid, wherein c) the induction of AC voltage in the electrolytic liquid causes the light-emitting diode to generate light.

Through experimentation, Applicant unexpectedly discovered that one or multiple light emitting units will emit light in a liquid when AC voltage is applied to the liquid and when the light-emitting units are rated for voltages and amp draws commensurate with available electrical energy. The production of autotrophic microorganisms is fundamentally constrained by the ability of light to penetrate through a liquid and thereby enable photosynthesis. Prior to Applicant's invention as disclosed herein, no methods were believed to be known to produce light in a liquid through the utilization of light-emitting devices physically unconnected to an electrical voltage source vis-à-vis solid conductive material. In one embodiment, the utilization of one or more, and preferably many, free-floating light-emitting units in an electrically charged liquid comprising autotrophic microorganisms enables a very high light transmission efficiency, wherein previous light penetration constraints are largely overcome and high autotrophic microorganism densities are fully enabled.

In several embodiments, a method for producing a polyhydroxyalkanoate (PHA) in a microorganism culture is provided. In some embodiments, the method comprises the steps of: a) subjecting said culture to a growth period comprising exposing said culture to growth conditions to cause said culture to reproduce, (b) subjecting said culture to a polymerization period comprising exposing said culture to polymerization conditions to cause said culture to produce intracellular PHA, and (c) repeating step (a) and then second step (b) two or more times.

In some embodiments the growth period comprises a period in which the culture reproduces or otherwise produces biomass and/or reproduces. In some embodiments, the polymerization period comprises a period in which the culture synthesizes PHA. In some embodiments, the growth period and the polymerization period are induced by the culture media (e.g., the extracellular media around the culture). In some embodiments, alterations in the media conditions induce a transition (partial or complete) between growth and polymerization periods. In some embodiments, a culture is cycled between growth and polymerization periods two, three, four, or more times, in order to produce PHA and then reproduce biomass, which is subsequently used to generate additional PHA.

In some embodiments, the culture is exposed to non-sterile conditions. In certain such embodiments, input carbon is non-sterile. However, in some embodiments, sterile conditions exist. In some embodiments, the culture is dynamic over time in that it may be exposed to extraneous microorganisms. In certain embodiments, this is due to a non-sterile culture environment. In some embodiments, extraneous microorganisms potentiate the production of PHA.

In several embodiments, a process for the reduction of pigmentation in a microorganism culture is provided. In one embodiment, the process comprises the steps of: providing a medium comprising a microorganism culture comprising dissolved oxygen, and increasing the concentration of dissolved oxygen over successive periods to select for light-colored or low-level pigmentation microorganisms.

PHA, while able to be treated post-production to reduce pigmentation, is less expensive to produce when lower levels of pigmentation exist. Some microorganisms are more pigmented than others, and therefore in several embodiments, selection against the more pigmented microorganisms results in a less pigmented PHA, which reduces production costs. In some embodiments, the microorganisms cultured and selected for are methanotrophic microorganisms. By manipulating the culture conditions, which benefit certain varieties of microorganisms, a less pigmented culture (and hence a less pigmented PHA) result. In some embodiments, increases in concentration of dissolved oxygen over periods ranging from 1-3 hours, 3-5 hours, 5-7 hours, 7-10 hours, 10-15 hours, or 15-24 hours are used to select for less pigmented microorganisms. As discussed herein, in several embodiments, various compounding agents are optionally added to the produced PHA (either during the production phase or after production phase). Many such compounding agents, however, adversely affect the quality and/or performance (or other characteristic) of the final PHA product. In several embodiments, certain compounding agents, or combinations thereof, are added in order to improve one or more characteristics of the final PHA product. In some embodiments, such agents aid in the reduction of pigmentation of the PHA. In some embodiments, compounding agents reduce the degree of filtration, centrifugation, settling (or other techniques disclosed herein to separate solids from liquid phases). Advantageously and unexpectedly, the addition of certain compounding agents, viewed in the art as harmful to the quality or to a certain characteristic of the PHA, the result achieve with the methods disclosed herein is a higher quality PHA that is not adversely affected by the compounding agents, but rather is enhanced by the addition of such compounds. In several embodiments, a process for the conversion of a gas into a polyhydroxyalkanoate (PHA) is provided, wherein the process comprises the steps of: a) providing i) a first gas and ii) a culture of microorganisms, b) contacting the first gas with the culture to cause the culture to convert the first gas into a second gas c) contacting the second gas with the culture, and d) causing the culture to use the second gas to produce PHA.

In some embodiments, the microorganisms are autotrophic, methanogenic, heterotrophic, or combinations thereof.

In one embodiment the first gas is carbon dioxide. In one embodiment the first gas is oxygen. In one embodiment the first gas is methane. In one embodiment the first gas is a volatile organic compound.

In one embodiment the second gas is carbon dioxide. In one embodiment the second gas is oxygen. In one embodiment the second gas is methane. In one embodiment the second gas is a volatile organic compound.

In one embodiment, the selection of the first and the second gas is based on the type of microorganism or microorganisms being cultured.

BRIEF DESCRIPTION OF THE DRAWING

FIG. 1 is a block flow diagram comprising the steps of: microorganism fermentation and PHA synthesis, PHA-containing biomass removal, PHA-reduced biomass and isolated PHA production, PHA-reduced biomass recycling and fermentation, and isolated PHA purification.

DETAILED DESCRIPTION

While PHAs have significant environmental advantages compared to fossil fuel-based plastics, the cost of PHA production is generally viewed as a significant limitation to the industrial production and commercial adoption of PHAs. Generally, the overall cost of PHA production is determined by three major inputs: 1) carbon, 2) chemicals, and 3) energy. Accordingly, efforts to reduce the cost of PHA production must address one or more of these areas, specifically by: i) reducing carbon input costs, ii) increasing carbon-to-PHA yields, iii) reducing the volume of chemicals required for PHA production, and/or iv) increasing energy-to-PHA yields.

As discussed above, food crop derived sugars in genetically engineered microorganism-based aqueous fermentation systems are widely regarded as the most carbon, chemical, energy, and, thus, cost efficient PHA production method. Despite these efficiencies, sugar-based PHA production remains many times more expensive than fossil fuel-based plastics production. Attempts to reduce the carbon input cost of the PHA production process, by utilizing carbon-containing industrial off-gases, such as carbon dioxide and methane, have been previously limited by technical challenges and stoichiometric limitations that render the gas-to-PHA production process significantly more energy and chemical intensive, and thus more costly, than the food crop-based PHA production process.

Specifically, these technical challenges and stoichiometric limitations include: low mass transfer rates, low microorganism growth rates, extended polymerization times, low cell densities, high oxygen demand (relative to solid substrates), and low PHA cellular inclusion concentrations. Whereas sugar-based fermentation systems have the ability to generate high cellular densities and PHA inclusion concentrations, carbon-containing gas-based fermentation processes typically cannot, based on fundamental cell morphology and mass transfer constraints, generate cellular and PHA densities exceeding 10-30% of densities possible in sugar-based processes. As a result, the ratio of energy-to-PHA required to carry out upstream carbon injection, oxygen injection, system cooling, and culture mixing, as well as downstream PHA purification, significantly exceeds the energy-to-PHA ratio required for sugar-based PHA production methods, thereby rendering the emissions-based process uncompetitive when compared to both petroleum-based plastics and sugar-based PHAs.

Several embodiments of the present invention therefore relate to a novel method for the production of PHA using carbon-containing gases as a source of carbon (alone or in combination with a non-gaseous source of carbon), wherein the energy input-to-PHA production ratio, carbon input-to-PHA production ratio, and cost efficiency of the process is significantly improved over previous gas-based PHA production processes.

In several embodiments, this process may be accomplished by a) culturing a first microorganism culture capable of metabolizing the carbon within both a carbon-containing gas and biomass, or a derivative thereof, b) manipulating the conditions of the culture to cause the culture to produce PHA-containing biomass, c) removing a portion of the PHA-containing biomass; d) extracting at least a portion of the PHA within the removed PHA-containing biomass to create substantially isolated PHA and substantially PHA-reduced biomass, e) purifying the isolated PHA, and f) returning the PHA-reduced biomass to the microorganism culture to cause the microorganism culture to metabolize the carbon within the PHA-reduced biomass into PHA.

According to some embodiments, the steps of this process are as follows: (a) providing a microorganism culture comprising biomass and PHA; (b) removing a portion of the PHA-containing biomass from the culture, and extracting PHA from the removed PHA-containing biomass to produce isolated PHA and PHA-reduced biomass; (c) purifying the isolated PHA, and (d) returning the PHA-reduced biomass to be mixed with the culture to cause the culture to convert the carbon within the PHA-reduced biomass into PHA. Each of the above recited steps in the process are discussed in more detail below.

Providing a Microorganism Culture Comprising Biomass and PHA

The terms "microorganism", "microorganisms", "culture", "cultures", and "microorganism cultures", as used herein, shall be given their ordinary meanings and shall include, but not be limited to, a single strain of microorganism and/or consortium of microorganisms, including, among others, genetically-engineered bacteria, fungi, algae, and/or yeast. In some embodiments, microorganisms are naturally occurring and in some embodiments microorganisms are genetically-engineered. In some embodiments, both naturally occurring and genetically-engineered microorganisms are used. In some embodiments, a mixed culture of microorganisms may be used. In some embodiments, microorganisms or cultures shall include a microorganism metabolism system, including the interactions and/or multiple functions of multiple cultures in one or more conditions.

The terms "biomass" and "biomass material" shall be given their ordinary meaning and shall include, but not be limited to, microorganism-derived material, including intracellular, cellular, and/or extracellular material, such materials including, but not limited to, a polymer or polymers, amino acids, nucleic acids, carbohydrates, lipids, sugars, PHA, volatile fatty acids, chemicals, gases, such as carbon dioxide, methane, volatile organic acids, and oxygen, and/or metabolic derivatives, intermediaries, and/or end-products. In several embodiments, biomass is dried or substantially dried.

In some embodiments, the biomass contains less than about 99% water. In other embodiments, the biomass contains between about 99% to about 75% water, including about 95%, 90%, 85%, and 80%. In some embodiments, the biomass contains between about 75% and about 25% water, including 75%-65%, 65%-55%, 55%-45%, 45%-35%, 35%-25%, and overlapping ranges thereof. In additional embodiments, the biomass contains from about 25% water to less than about 0.1% water, including 25%-20%, 20%-15%, 15%-10%, 10%-5%, 5%-1%, 1%-0.1%, and overlapping ranges thereof. In still other embodiments, the biomass contains no detectable amount of water. Depending on the embodiment, water is removed from the biomass by one or more of freeze drying, spray drying, fluid bed drying, ribbon drying, flocculation, pressing, filtration, and/or centrifugation. In some embodiments, the biomass may be mixed with one or more chemicals (including, but not limited to solvents), such as methylene chloride, acetone, methanol, and/or ethanol, at various concentrations. In other embodiments, the biomass may be processed through homogenization, heat treatment, pH treatment, enzyme treatment, solvent treatment, spray drying, freeze drying, sonication, or microwave treatment. As used herein, the term "PHA-reduced biomass" shall be given its ordinary meaning and shall mean any biomass wherein at least a portion of PHA has been removed from the biomass through a PHA extraction process. As used herein, the term "PHA-containing biomass" shall be given its ordinary meaning and shall mean any biomass wherein at least a portion of the biomass is PHA.

Microorganism cultures useful for the invention described herein include a single strain, and/or a consortium of strains, which are individually and/or collectively capable of using carbon containing gases and biomass, including PHA-reduced biomass, as a source of carbon for the production of biomass and PHA. In some embodiments, a microorganism culture according to several embodiments, comprises a microorganism culture that utilizes PHA-reduced biomass, or any derivative thereof, including methanotrophic microorganisms, anaerobic digestion cultures, and other heterotrophic microorganisms, as a source of carbon for the production of biomass, or metabolic derivatives including, and in particular, the production of PHA, protein, methane, and/or carbon dioxide (herein, "biomass-utilizing microorganisms"). As used herein, the terms "microorganism", "culture", "microorganism culture" "microorganism system", "microorganism consortium", "microorganism conglomerate" and "consortium of microorganisms" are used interchangeably. Additionally, any of these terms may refer to one, two, three, or more microorganism cultures and/or strains, including a microorganism system that is collectively capable of carrying out a complex metabolic function (e.g., conversion of PHA-reduced biomass to methane, carbon dioxide, protein, and/or PHA). In several embodiments, the microorganism culture comprises of a consortium of carbon-containing gas-utilizing microorganisms and a consortium of biomass-utilizing microorganisms. In some embodiments, the gases metabolized by such cultures comprise methane, carbon dioxide, and/or a combination thereof.

In some embodiments, the microorganism culture comprises a consortium of acidogenic, acetogenic, methanogenic, methanotrophic, and/or autotrophic microorganisms in one or more individual bioreactors. As such, in some embodiments, the cultures are grown in one or more distinct culture conditions. In some embodiments, the conditions are either aerobic or anaerobic conditions. In some embodiments, culture conditions are varied over time (e.g. initially aerobic with a transition to anaerobic, or vice versa). As used herein, the term "bioreactor" shall be given its ordinary meaning and shall also refer to a tank, vessel, group of vessels, tank of vessels, or any device or system suitable for growth and culturing of microorganisms. In one embodiment, a device is provided that is capable of carrying out gas-based fermentation, methanotrophic metabolism, bioreaction, autotrophic metabolism, heterotrophic metabolism, and/or biocatalyst-based metabolism at high efficiency, particularly using one or more, and particularly at least two gases as nutrient (e.g., carbon and oxygen) input sources, measured in the following terms: 1) gas capture efficiency, 2) mass transfer efficiency (including in terms of the power required to transfer gas into aqueous/dissolved form), and 3) material synthesis (in terms of grams per liter per hour). In one embodiment, a system is provided for gas input reactions (e.g., methane and oxygen; oxygen and carbon dioxide; carbon dioxide and methane; methane, ammonia, and oxygen; methane, ammonia, oxygen, and dinitrogen; methane, carbon dioxide, and oxygen; or various combinations of such input gasses) that utilizes a system comprising multiple reaction vessels. In one embodiment, one or more vessel may be equipped with a rotating mixer. In one embodiment, the rotating mixer may induce cavitation in the liquid medium. In one embodiment, such cavitation may cause acute induction of gas entrainment into the liquid medium, significantly increasing mass transfer induction. In one embodiment, gas may be injected into one or more of the vessels behind the leading edge of a moving material in liquid medium, in order to reduce and then increase the driving pressure of the gas injection. In one embodiment, the pressure of the liquid medium may be pulsed through periods of high pressure and low pressure to increase the mass transfer of gas into liquid medium. In one embodiment, the pulsation of pressure in a liquid medium may be employed, wherein the high pressure (e.g., up to 100 psi) period may have a duration from 0.001 seconds to 25 minutes, and wherein the low pressure period (e.g., from −25 inches vacuum to 5 psi) may have a duration from 0.001 seconds to 25 minutes. In one embodiment, the rapid induction of pressure pulsation may be effected by fitting a vessel with a means of transferring acoustic energy into the vessel medium. In one embodiment, the rapid induction of pressure pulsation may be effected by fitting a vessel with a transducer. In one embodiment, the rapid induction of pressure pulsation may be effected by fitting a vessel with one or more sonication means, wherein the liquid medium is sonicated, wherein such sonication is diffused throughout a volume sufficient to avoid damage to microorganisms or enzymes in the liquid medium. In one embodiment, silica gel or silica-based liquid is added to the liquid medium to increase the solubility of methane and oxygen in the liquid medium. In one embodiment, the reaction vessels comprise fully or partially enclosed vessels. In one embodiment, the reaction vessels comprise fully or partially-enclosed medium-containing volumes or medium-containing compartments, within or in addition to one or more tanks, compartments, vessels, or other volumes. In one embodiment, the vessels may be plastic or stainless steel enclosed vessels or medium-containing volumes. In one embodiment, the vessels may not be physically connected. In one embodiment, the vessels may be physically connected. In one embodiment, gas may be directed into one or more of the vessels simultaneously. In one embodiment, a reactor, reactor system, or system may comprise multiple vessels combined. In one embodiment, gas may be directed equally into each of vessels. In one embodiment, gas may be directed more into one vessel and less into another vessel. In one embodiment, gas may be directed first into one vessel, and then into another vessel. In one embodiment, gas may be exhausted from all vessels equally. In one embodiment, gas may be exhausted from all vessels individually, or more from one vessel and less from another vessel. In one embodiment, exhaust gas may be directed from one vessel into another vessel. In one embodiment, the liquid medium of the vessels is discrete and not mixed between the vessels. In one embodiment, the liquid medium of the vessels is not discrete and is mixed between the vessels. In one embodiment, gas is directed equally into all vessels, and liquid medium is mixed between the vessels. In one embodiment, gas is directed equally into all vessels, and liquid medium is at least partially mixed between the vessels. In one embodiment, gas is directed equally into all vessels, and liquid medium is at least partially mixed between the vessels. In one embodiment, gas is directed equally into all vessels, and liquid medium is not mixed between the vessels. In one embodiment, gas is directed first into one vessel and then into another vessel, and liquid medium is mixed between the vessels. In one embodiment, gas is directed first into one vessel and then into another vessel, and liquid medium is not mixed between the vessels. In one embodiment, exhaust gas from a first vessel is directed into a second vessel, and liquid medium is mixed between the vessels. In one embodiment, gas is directed individually and discretely into each vessel, and liquid medium is mixed between the vessels. In one embodiment, exhaust gas is directed individually and discretely into each vessel, and liquid medium is not mixed between the vessels. In one embodiment, the concentration of dissolved gas is caused to remain relatively elevated in one vessel and relatively depressed in another vessel. In one embodiment, the concentration of dissolved gas is caused to remain substantially equal in multiple vessels. In one embodiment, the gases are caused to be mixed equally throughout the vessels. In one embodiment, the gases are caused to move sequentially through the vessels. In one embodiment, the gases are caused to be injected individually into through the vessels. In one embodiment, the gases are caused to be injected individually and simultaneously into the vessels. In one embodiment, the gases are caused to move simultaneously through the vessels on an individual basis and medium is caused to not be fully mixed between the vessels, such that the medium remains substantially isolated. In one embodiment, the gases are caused to move sequentially through the vessels and medium is caused to not be fully mixed between the vessels. In one embodiment, the gases are caused to be injected individually and simultaneously into the vessels and medium is caused to be mixed between the vessels, such that the medium remains substantially non-isolated. In one embodiment, the gases are caused to move sequentially through the vessels to cause the medium in the vessels to be substantially non-isolated and gas is caused to move in multiple directions in each vessel. In one embodiment, the gases are caused to be injected simultaneously into the vessels, such that the gases are caused to move the medium in the vessels to be substantially non-isolated. In one embodiment, the gases are caused to be injected simultaneously into the vessels in such a manner that the gases are not caused to move the medium between the vessels. In one embodiment, gas may be moved between vessels by mechanical means, such as a pump. In one embodiment, liquid medium may be moved between vessels by mechanical means, such as a pump. In one embodiment, gas may be injected into a vessel by mechanical means. In one embodiment, liquid medium may be injected into a vessels by mechanical means, such as a pump. In one embodiment, gas and liquid medium may be injected simultaneously into a vessel by mechanical means, such as a pump, nozzle, venturi, compressor, diffusor, vacuum. In one embodiment, the vessels may be equipped with one or more internal cavitation mechanisms. In one embodiment, the vessels may be operated under recurring periods or patterns of pressure and vacuum to induce optimal mass transfer efficiency. In one embodiment, the vessels may be filled with one or more materials, that are more or less dense than liquid medium, that are able to dissolve or absorb high concentrations or amounts of gases, such as methane, oxygen, or carbon dioxide, wherein such materials may be silica-based gels or beads, activated carbon, nickel-plated spheres, polypropylene beads, PES beads, PTFE beads, or ultra high molecular weight polyethylene pellets. In one embodiment, the rapid pulsation of pressure in the vessels causes the absorbent materials to absorb gases at high concentration, and then release at least some of the gases into the medium, causing an increase in mass transfer into the liquid medium. In one embodiment, a vessel is filled with liquid medium containing gas-absorbent material, such as plastic beads, and the vessel is subject to recurring periods of pressurization, such that the vessel acts similar to an oxygen concentration system or other pressure swing absorption system, thereby increasing the solubility, mass transfer, and/or uptake of gases in the vessel by the microorganisms and liquid medium. In one embodiment, such pressure or depressurization cycle may comprise 1-100 minutes per cycle or stage, or 1-300 minutes per complete pressure-depressurization cycle. In one embodiment, the liquid medium and/or concentration of dissolved gases in the reactor is caused to remain relatively constant or homogenous with mixing induced by the action of the cavitation (e.g., cavitation induced by a moving blade or liquid moving over a surface), sonication (e.g., ultrasonication), sonic induction, gases (e.g., gas displacement), liquid displacement, mechanical pumping (e.g., rotary pump), the movement of entrained materials (e.g., the movement of liquid-entrained plastic balls), or other means while the concentration of gases is caused to be reduced on a proximal basis according to the cycle of pressure in the system (e.g., from vacuum pressure to superatmospheric pressure), proximity to an absorbent material (including the associated pressure cycle), sequential location of gas relative to gas flow path (e.g., location in gas vessels), and location or proximity to injection port relative to exhaust port (e.g., retention time of gas). In one embodiment, a reactor may be vertically configured, such that the height of the vessel exceeds the width of the vessel. In one embodiment, a reactor may be horizontally configured, such that the width of the vessel exceeds the height of the vessel.

In some embodiments, the microorganism culture is contained within a single vessel, wherein the steps of converting PHA-reduced biomass to biomass, converting biomass to PHA, and converting carbon-containing gases to biomass and/or PHA occur simultaneously or sequentially.

In other embodiments, the microorganism culture is contained within multiple vessels, which are designed to carry out specific and unique functions. For example, one embodiment includes the steps of (a) converting PHA-reduced biomass to PHA-reduced biomass-derived materials such volatile organic acids, methane, and/or carbon dioxide, which is carried out in a first vessel and (b) synthesizing PHA from PHA-reduced biomass-derived materials which is carried out in a second, separate tank under independent conditions. In some embodiments, one or more of the tanks is an anaerobic digestion tank and one or more other tank is an aerobic fermentation tank.

As used herein, the term "gas-utilizing microorganisms" shall be given its ordinary meaning and shall refer to microorganisms capable of utilizing gases containing carbon for the production of biomass, including the production of PHA. Similarly, the terms "methanotrophic microorganisms" and "methane-utilizing microorganisms" shall be given their ordinary meanings and shall refer to microorganisms capable of utilizing methane as a source of carbon for the production of biomass. Further, the terms "autotrophic microorganisms" and "carbon dioxide-utilizing microorganisms" shall be given their ordinary meaning and shall refer to microorganisms capable of utilizing carbon dioxide as a source of carbon for the production of biomass, including microorganisms that utilize natural and/or synthetic sources of light to carry out the metabolism of carbon dioxide into biomass. The term "heterotrophic microorganisms", as used herein, shall be given its ordinary meaning and shall include methanotrophic, methanogenic, acidogenic, acetogenic and biomass-utilizing microorganisms, including microorganisms that convert sugar, volatile fatty acids, or other carbon substrates to biomass. The term "methanogenic microorganisms" shall be given its ordinary meaning and shall refer to microorganisms that convert biomass to methane, including the consortium of microorganisms required to carry out such a process, including, but not limited to, acidogenic and acetogenic microorganisms.

As discussed herein, in several embodiments, carbon-containing gases are used as a source of carbon by microorganism cultures. In some embodiments, other sources of carbon are used (e.g., PHA-reduced biomass), either alone or in combination with carbon-containing gases. In some embodiments, the carbon-containing gases used include, but are not limited to, carbon dioxide, methane, ethane, butane, propane, benzene, xylene, acetone, methylene chloride, chloroform, volatile organic compounds, hydrocarbons, and/or combinations thereof. The source of the carbon-containing gases depends on the embodiment. For example, carbon-containing gas sources used in some embodiments include landfills, wastewater treatment plants, anaerobic metabolism, power production facilities or equipment, agricultural digesters, oil refineries, natural gas refineries, cement production facilities, and/or anaerobic organic material digesters, including both solid and liquid material digesters.

In several embodiments described herein, microorganisms may include, but are not limited to, yeast, fungi, algae, and bacteria (including combinations thereof). Suitable yeasts include, but are not limited to, species from the genera *Candida, Hansenula, Torulopsis, Saccharomyces, Pichia, 1-Debaryomyces, Lipomyces, Cryptococcus, Nematospora,* and *Brettanomyces*. Suitable genera include *Candida, Hansenula, Torulopsis, Pichia,* and *Saccharomyces*. Non-limiting examples of suitable species include, but are not limited to: *Candida boidinii, Candida mycoderma, Candida utilis, Candida stellatoidea, Candida robusta, Candida claussenii, Candida rugosa, Brettanomyces petrophilium, Hansenula minuta, Hansenula satumus, Hansenula californica, Hansenula mrakii, Hansenula silvicola, Hansenula polymorpha, Hansenula wickerhamii, Hansenula capsulata, Hansenula glucozyma, Hansenula henricii, Hansenula nonfermentans, Hansenula philodendra, Torulopsis candida, Torulopsis bolmii, Torulopsis versatilis, Torulopsis glabrata, Torulopsis molishiana, Torulopsis nemodendra, Torulopsis nitrato-phila, Torulopsis pinus, Pichia farinosa, Pichia polymorpha, Pichia membranaefaciens, Pichia pinus, Pichia pastoris, Pichia trehalophila, Saccharomyces cerevisiae, Saccharomyces fragilis, Saccharomyces rosei, Saccharomyces acidifaciens, Saccharomyces elegans, Saccharomyces rouxii, Saccharomyces lactis,* and/or *Saccharomyces fractum.*

In several embodiments, mutants (including genetically-engineered or naturally occurring) of the above-referenced yeasts are used. For example, in several embodiments, mutants having about 99.9%, about 99%, about 98%, about 97%, about 96%, about 95%, about 94%, about 93%, about 92%, about 91%, about 90%, about 85%, about 80%, about 70%, about 60%, about 50%, about 25%, or about 10% genetic homology (e.g., in comparing genome to genome) to the above-referenced yeasts are used. In some embodiments, microorganisms are used in which particular genes (including groups of genes or families of genes) are mutated such that one or more of the genes exhibit less than 100% sequence similarity (e.g., about 99.9%, about 99%, about 98%, about 97%, about 96%, about 95%, about 94%, about 93%, about 92%, about 91%, about 90%, about 85%, about 80%, about 70%, about 60%, about 50%, about 25%, or about 10% sequence homology) to a corresponding gene (or genes) in the microorganisms disclosed herein. In some embodiments, one or more point mutations in the DNA of the microorganism account for the mutant status. In some embodiments, the point mutation(s) are transitions, in some embodiments they are transversions, and in some embodiments wherein more than one point mutation is present, combinations of transitions and transversions exist. In some embodiments, the mutations are nonsense mutations, missense mutations, silent mutations, or combinations thereof. In some embodiments, the mutations are deletions, insertions or combinations thereof. In some embodiments, such mutations lead to frameshifts in the genetic code, which may lead to alterations in the resultant protein. In some embodiments, the genetic discrepancies result in altered protein (e.g., non-functional, reduced function, truncated, non-expressed) as compared to a non-mutant bacteria. In some embodiments, non-functional or reduced function proteins exhibit less than about 99%, about 95%, about 90%, about 85%, about 80%, about 70%, about 60%, about 50%, about 25%, or about 10% of the activity of a normal protein. In some embodiments, truncated proteins are partially functional, while in some embodiments, they are non-functional. In some embodiments, the proteins are not expressed. In some embodiments, post-translational modification of proteins results in altered expression or function of one or more proteins of the microorganism (e.g., an enzyme in a metabolic pathway). Such modifications include, but are not limited to, myristoylation, palmitoylation, isoprenylation or prenylation, farnesylation, geranylgeranylation, glypiation, glycosylphosphatidylinositol anchor formation, lipoylation, flavination, heme C attachment, phosphopanteteheinylation, retinylidene Schiff base formation, diphthamide formation, ethanolamine phosphoglycerol attachment, hypusine formation, acylation, N-acylation (amides), S-acylation (thioesters), acetylation, deacetylation, formylation, alkylation, methylation, demethylation, amide bond formation, amidation at C-terminus, amino acid addition (e.g., arginylation, polyglutamylation, polyglycylation), butyrylation, gamma-carboxylation, glycosylation, glycation, polysialylation, malonylation, hydroxylation, iodination, nucleotide addition such as ADP-ribosylation, oxidation, phosphate ester (O-linked) or phosphoramidate (N-linked) formation, phosphorylation, adenylylation, propionylation, pyroglutamate formation, S-glutathionylation, S-nitrosylation, succinylation, sulfation, selenoylation, glycation, biotinylation, pegylation, ISGylation, SUMOylation, ubiquitination, Neddylation, Pupylation, citrullination, deimination, deamidation, eliminylation, carbamylation, formation of disulfide bridges, proteolytic cleavage, and racemization.

Suitable bacteria include, but are not limited to, species from the genera *Bacillus, Mycobacterium, Actinomyces, Nocardia, Pseudomonas, Methanomonas, Protaminobacter, Methylococcus, Arthrobacter, Methylomonas, Brevibacterium, Acetobacter, Methylomonas, Brevibacterium, Acetobacter, Micrococcus, Rhodopseudomonas, Corynebacterium, Rhodopseudomonas, Microbacterium, Achromobacter, Methylobacter, Methylosinus*, and *Methylocystis*. Preferred genera include *Bacillus, Pseudomonas, Protaminobacter, Micrococcus, Arthrobacter* and/or *Corynebacterium*. Non-limiting examples of suitable species include, but are not limited to: *Bacillus subtilis, Bacillus cereus, Bacillus aureus, Bacillus acidi, Bacillus urici, Bacillus coagulans, Bacillus mycoides, Bacillus circulans, Bacillus megaterium, Bacillus licheniformis, Pseudomonas ligustri, Pseudomonas orvilla, Pseudomonas methanica, Pseudomonas fluorescens, Pseudomonas aeruginosa, Pseudomonas oleovorans, Pseudomonas putida, Pseudomonas boreopolis, Pseudomonas pyocyanea, Pseudomonas methylphilus, Pseudomonas brevis, Pseudomonas acidovorans, Pseudomonas methanoloxidans, Pseudomonas aerogenes, Protaminobacter ruber, Corynebacterium simplex, Corynebacterium hydrocarbooxydans, Corynebacterium alkanum, Corynebacterium oleophilus, Corynebacterium hydrocarboclastus, Corynebacterium glutamicum, Corynebacterium viscosus, Corynebacterium dioxydans, Corynebacterium alkanum, Micrococcus cerificans, Micrococcus rhodius, Arthrobacter rufescens, Arthrobacter paraafficum, Arthrobacter citreus, Methanomonas methanica, Methanomonas methanooxidans, Methylomonas agile, Methylomonas albus, Methylomonas rubrum, Methylomonas methanolica, Mycobacterium rhodochrous, Mycobacterium phlei, Mycobacterium brevicale, Nocardia salmonicolor, Nocardia minimus, Nocardia corallina, Nocardia butanica, Rhodopseudomonas capsulatus, Microbacterium ammoniaphilum, Archromobacter coagulans, Brevibacterium butanicum, Brevibacterium roseum, Brevibacterium flavum, Brevibacterium lactofermentum, Brevibacterium paraffinolyticum, Brevibacterium ketoglutamicum*, and/or *Brevibacterium insectiphilium*.

In several embodiments, mutants (including genetically-engineered or naturally occurring) of the above-referenced bacteria are used. For example, in several embodiments, mutants having about 99.9%, about 99%, about 98%, about 97%, about 96%, about 95%, about 94%, about 93%, about 92%, about 91%, about 90%, about 85%, about 80%, about 70%, about 60%, about 50%, about 25%, or about 10% genetic homology (e.g., in comparing genome to genome) to the above-referenced bacteria are used. In some embodiments, microorganisms are used in which particular genes (including groups of genes or families of genes) are mutated such that one or more of the genes exhibit less than 100% sequence similarity (e.g., about 99.9%, about 99%, about 98%, about 97%, about 96%, about 95%, about 94%, about 93%, about 92%, about 91%, about 90%, about 85%, about 80%, about 70%, about 60%, about 50%, about 25%, or about 10% sequence homology) to a corresponding gene (or genes) in the bacteria disclosed herein. In some embodiments, one or more point mutations in the DNA of the microorganism account for the mutant status. In some embodiments, the point mutation(s) are transitions, in some embodiments they are transversions, and in some embodiments wherein more than one point mutation is present, combinations of transitions and transversions exist. In some embodiments, the mutations are nonsense mutations, missense mutations, silent mutations, or combinations thereof. In some embodiments, the mutations are deletions, insertions or combinations thereof. In some embodiments, such mutations lead to frameshifts in the genetic code, which may lead to alterations in the resultant protein. In some embodiments, the genetic discrepancies result in altered protein (e.g., non-functional, reduced function, truncated, non-expressed) as compared to a non-mutant bacteria. In some embodiments, non-functional or reduced function proteins exhibit less than about 99%, about 95%, about 90%, about 85%, about 80%, about 70%, about 60%, about 50%, about 25%, or about 10% of the activity of a normal protein. In some embodiments, truncated proteins are partially functional, while in some embodiments, they are non-functional. In some embodiments, the proteins are not expressed. In some embodiments, post-translational modification of proteins results in altered expression or function of one or more proteins of the microorganism (e.g., an enzyme in a metabolic pathway). Such modifications include, but are not limited to, myristoylation, palmitoylation, isoprenylation or prenylation, farnesylation, geranylgeranylation, glypiation, glycosylphosphatidylinositol anchor formation, lipoylation, flavination, heme C attachment, phosphopanthetheinylation, retinylidene Schiff base formation, diphthamide formation, ethanolamine phosphoglycerol attachment, hypusine formation, acylation, N-acylation (amides), S-acylation (thioesters), acetylation, deacetylation, formylation, alkylation, methylation, demethylation, amide bond formation, amidation at C-terminus, amino acid addition (e.g., arginylation, polyglutamylation, polyglycylation), butyrylation, gamma-carboxylation, glycosylation, glycation, polysialylation, malonylation, hydroxylation, iodination, nucleotide addition such as ADP-ribosylation, oxidation, phosphate ester (O-linked) or phosphoramidate (N-linked) formation, phosphorylation, adenylylation, propionylation, pyroglutamate formation, S-glutathionylation, S-nitrosylation, succinylation, sulfation, selenoylation, glycation, biotinylation, pegylation, ISGylation, SUMOylation, ubiquitination, Neddylation, Pupylation, citrullination, deimination, deamidation, eliminylation, carbamylation, formation of disulfide bridges, proteolytic cleavage, and racemization.

In several embodiments, more than one type or species of microorganism is used. For example, in some embodiments, both algae and bacteria are used. In some embodiments, several species of yeast, algae, fungi, and/or bacteria are used. In some embodiments, a single yeast, algae, fungi, and/or bacteria species is used. In some embodiments, a consortium of cyanobacteria is used. In some embodiments, a consortium of methanotrophic microorganisms is used. In still additional embodiments, a consortium of both methanotrophic bacteria and cyanobacteria are used. In several embodiments, methanotrophic, heterotrophic, methanogenic, and/or autotrophic microorganisms are used.

In several embodiments of the invention, the microorganism culture comprises a consortium of methanotrophic, autotrophic, and/or heterotrophic microorganisms, wherein methane and/or carbon dioxide is individually, interchangeably, or simultaneously utilized for the production of biomass. In some embodiments, PHA-reduced biomass is used as a source of carbon by heterotrophic, autotrophic, and/or methanotrophic microorganisms. In several embodiments of the invention, the microorganism culture comprises methanotrophic microorganisms, cyanobacteria, and non-methanotrophic heterotrophic microorganisms, wherein methane and carbon dioxide are continuously utilized as sources of carbon for the production of biomass and PHA.

In some embodiments, microorganisms are employed in a non-sterile, open, and/or mixed environment. In other embodiments, microorganisms are employed in a sterile and/or controlled environment.

The terms "PHA", "PHAs", and "polyhydroxyalkanoate", as used herein, shall be given their ordinary meaning and shall include, but not be limited to, polymers generated by microorganisms as energy and/or carbon storage vehicles; biodegradable and biocompatible polymers that can be used as alternatives to petrochemical-based plastics such as polypropylene, polyethylene, and polystyrene; polymers produced by bacterial fermentation of sugars, lipids, or gases; and/or thermoplastic or elastomeric materials derived from microorganisms. PHAs include, but are not limited to, polyhydroxybutyrate (PHB), polyhydroxyvalerate (PHV), polyhydroxybutyrate-covalerate (PHBV), and polyhydroxyhexanoate (PHHx), as well as both short chain length (SCL), medium chain length (MCL), and long chain length (LCL) PHAs.

The terms "growth-culture medium", "growth medium", "growth-culture media", "medium", and "media", as used herein shall be given their ordinary meaning and shall also refer to materials affecting the growth, metabolism, PHA synthesis, and/or reproductive activities of microorganisms. Non-limiting examples of growth-culture media used in several embodiments include a mineral salts medium, which may comprise water, nitrogen, vitamins, iron, phosphorus, magnesium, and various other nutrients suitable to effect, support, alter, modify, control, constrain, and/or otherwise influence the metabolism and metabolic orientation of microorganisms. A growth-culture medium may comprise water filled with a range of mineral salts. For example, each liter of a liquid growth-culture medium may be comprised of about 0.7-1.5 g $KH_2PO_4$, 0.7-1.5 g $K_2HPO_4$, 0.7-1.5 g $KNO_3$, 0.7-1.5 g NaCl, 0.1-0.3 g $MgSO_4$, 24-28 mg $CaCl_2$) *$2H_2O$, 5.0-5.4 mg EDTA $Na_4(H_2O)_2$, 1.3-1.7 mg $FeCl_2$*$4H_2$a, 0.10-0.14 mg $CoCl_2$*$6H_2O$, 0.08-1.12 mg $MnCl_2$*$2H_2O$, 0.06-0.08 mg $ZnCl_2$, 0.05-0.07 mg $H_3BO_3$, 0.023-0.027 mg $NiCl_2$*$6H_2O$, 0.023-0.027 mg $NaMoO_4$*$2H_2O$, and 0.011-0.019 mg $CuCl_2$*$2H_2O$. A growth-culture medium can be of any form, including a liquid, semi-liquid, gelatinous, gaseous, foam, or solid substrate.

In several embodiments of the invention, a microorganism culture is produced in a liquid growth medium, wherein carbon dioxide and methane are utilized as a gaseous source of carbon for the production of methanotrophic and/or autotrophic biomass. In some embodiments, PHA-reduced methanotrophic and/or PHA-reduced autotrophic biomass is utilized as a source of carbon for the production of heterotrophic biomass and heterotrophically-produced PHA. In some embodiments, the growth medium is manipulated to effect the growth, reproduction, and PHA synthesis of the microorganism culture. Methods for the production of methanotrophic microorganisms are disclosed in the art, and are described by Herrema, et al., in U.S. Pat. No. 7,579,176, which is hereby incorporated by reference in its entirety. Methods for the production of cyanobacteria are described by Lee, et al. ("High-density algal photobioreactors using light-emitting diodes," Biotechnology and Bioengineering, Vol. 44, Issue 10, pp. 1161-1167), which is hereby incorporated by reference in its entirety. Methods for the production of methane from biomass are described by Deublein, et al. ("Biogas from Waste and Renewable Resources, WILEY-VCH Verlag GmbH & Co. KgaA, 2008), which is hereby incorporated by reference in its entirety. In some embodiments, PHA synthesis may be effected through the manipulation of one of more elements of the culture medium, including through the reduction, increase, or relative change in either the total or bioavailable concentration of one or more of the following elements (also referred to as essential nutrients): carbon, oxygen, magnesium, phosphorus, phosphate, potassium, sulfate, sulfur, calcium, boron, aluminum, chromium, cobalt, iron, copper, nickel, manganese, molybdenum, sodium, nitrogen, nitrate, ammonia, ammonium, urea, amino acids, methane, carbon dioxide, and/or hydrogen. Methods for the production of PHA are described by Herrema, et al., in U.S. Pat. No. 7,579,176. Depending on the embodiment, all of the various components (including elements, compounds, liquids, gases, solids, and other compositions) of a culture medium can be considered essential nutrients, given that they support the growth of the microorganisms.

In one embodiment, the conversion of the PHA-reduced biomass into the PHA is effected by manipulating the concentration one or more elements within a growth medium selected from the group consisting of: nitrogen, methane, carbon dioxide, phosphorus, oxygen, magnesium, potassium, iron, copper, sulfate, manganese, calcium, chlorine, boron, zinc, aluminum, nickel, and/or sodium, and combinations thereof. Methods to control the concentration of elements within the medium include, but are not limited to, automatic, continuous, batch, semi-batch, manual, injection, solid feed, liquid, or other methods of inputting one or more chemical into the medium, wherein the total and/or bioavailable concentration of elements is increased, decreased, maintained, adjusted, or otherwise controlled at one or more time and/or physical chemical adjustment points. Additional methods to adjust the total or bioavailable concentration of one or more elements within a mineral media include, but are not limited to, the directed precipitation, chelation, de-chelation, and de-precipitation of elements. In one embodiment, the directed precipitation or chelation of one or more element is utilized to reduce the total or bioavailable concentration of one or more element within a medium and thereby induce or increase PHA production in a biomass. In one embodiment, an ion exchange system, including one or more reversible ion exchange resins, is used to control the concentration of ions with the medium and/or control the precipitation or solubilization of elements within the medium. In one embodiment, the medium is passed through an ion exchange resin in order to induce the reduction or increase of a specific ion in the medium in order to induce or preclude PHA production in a biomass.

In one embodiment, the concentration of one or more elements within a growth culture medium is increased, controlled, manipulated, or managed to induce or increase the rate of PHA production in biomass, including a microorganism culture. As used herein, the terms "control", "manipulate", "adjust", "maintain", "manage" and the like shall be given their ordinary meaning and shall also refer to steps which are taken to keep or achieve concentrations of certain nutrients, compounds or elements of a culture within a desired range. For example, in one context controlling the concentration of an element may result in the maintenance of the concentration of that element within a certain range, that concentration being achieved by the addition of that element and/or dilution of the culture to reduce the concentration of that element. In one embodiment, the concentration of phosphorus within the medium is increased to induce or increase the rate of PHA production in a microorganism culture. In another embodiment, the concentration of an element, e.g., phosphorus, carbon dioxide, iron, copper, oxygen, methane, and/or magnesium, within the medium is manipulated or increased to cause a metabolic shift in the microorganism culture, such that the production of non-PHA materials by the culture using nitrogen sources (e.g., nitrate, ammonia, ammonium, dinitrogen, urea, or amino acids) is reduced, inhibited, or otherwise impacted to enhance PHA production. In one embodiment, the concentration of phosphorus within the medium is manipulated or increased to reduce the utilization of nutrients, including nitrogen, oxygen, and/or carbon, for the production of non-PHA materials by the culture. In another embodiment, the concentration of phosphorus within the medium is manipulated or increased to reduce the utilization of nutrients for the production of non-PHA materials by the culture and induce or increase the rate of PHA production in the culture. In some embodiments, an increase in the concentration of phosphorus causes a metabolic shift that favors the production of PHA at the expense of other non-PHA materials, including a reduction in the production of protein, nucleic acids, polysaccharides, sugars, lipids, particularly but not necessarily under growth-limiting conditions, including nitrogen (e.g., nitrate, ammonia, ammonium, dinitrogen, urea, or amino acids), oxygen, magnesium, potassium, iron, copper, or other nutrient-limiting conditions. In some embodiments, an increase in the concentration of phosphorus above 0.00 ppm, 0.01 ppm, 0.02 ppm, 0.05 ppm, 0.10 ppm, 0.20 ppm, 0.50 ppm, 1.00 ppm, 1.25 ppm, 1.50 ppm, 1.75 ppm, 2.00 ppm, 2.20 ppm, 2.40 ppm, 3 ppm, 4 ppm 5 ppm, 6 ppm, 8 ppm, 20 mM, 30 mM, 40 mM, 50 mM, 60 mM, 70 mM, 80 mM, 90 mM, 100 mM, 110 mM, or 120 mM, and particularly above 40 mM or 80 mM, causes a reduction in the utilization of carbon and nitrogen sources for the production of non-PHA material, including proteins, non-PHA polymers, nucleic acids, lipids, pigments, polysaccharides, methanobactin, and/or carbon dioxide, and, under growth-limiting conditions, an increase in the utilization of carbon sources for the production of PHA material, as a result of metabolic changes in the culture and/or chemical interactions between chemicals within the media and/or culture induced by augmented concentrations of phosphorus. The elevation of phosphorus concentrations as a method to induce or increase the rate of PHA production in a biomass culture is contrary to the teachings of the prior art, which teaches that PHA production is induced or enhanced by reducing or eliminating the concentration of elements, such as, e.g., phosphorus in the mineral medium. The addition or controlled elevation of an element, such as, e.g., phosphorus to a biomass system to induce or increase PHA production produces an unexpected and surprising increase in PHA production in a biomass system. An element such as, e.g., phosphorus may be added to the mineral media using a variety of phosphorus sources, including phosphorus, phosphate, phosphoric acid, sodium phosphate, disodium phosphate, monosodium phosphate, and/or potassium phosphate; other elements, such as dissolved carbon dioxide, Fe(II) iron, Fe(III) iron, copper sulfate, Fe-EDTA, dissolved oxygen, dissolved methane, and/or magnesium sulfate, hydrogen sulfide, and sodium hydroxide are among other potential sources of elements that may be added to the mineral media.

In one embodiment of the invention, the concentrations of dissolved gases, such as methane, oxygen, carbon dioxide, and/or nitrogen, are manipulated to increase the rate of PHA production relative to the rate of cellular production of non-PHA materials and, specifically, to cause a reduction in the utilization of carbon or nitrogen sources for the production of non-PHA material, including proteins, non-PHA polymers, enzymes, nucleic acids, lipids, pigments, polysaccharides, and/or carbon dioxide, and, under some conditions, including growth-limiting conditions, further cause an increase in the utilization of carbon sources for the production of PHA material, as a result of metabolic changes in the culture and/or chemical interactions between chemicals within the media and/or culture induced by augmented concentrations of one or more of such dissolved gases. In one embodiment, the concentration of methane or dissolved methane is manipulated to between about 0.01 ppm and about 0.05 ppm, between about 0.05 ppm and about 0.1 ppm, between about 0.1 ppm and about 0.5 ppm, between about 0.5 ppm and about 1.0 ppm, between about 1.0 ppm and about 1.5 ppm, between about 1.5 ppm and about 1.75 ppm, between about 1.75 ppm and about 2.0 ppm, between about 2.0 ppm and about 2.5 ppm, between about 2.5 ppm and about 3.0 ppm, between about 3.0 ppm and about 3.5 ppm, between about 3.5 ppm and about 4.0 ppm, between about 4.0 ppm and about 4.5 ppm, between about 4.5 ppm and about 5.0 ppm, between about 5.0 ppm and about 6.0 ppm, between about 6.0 ppm and about 7.0 ppm, between about 7.0 ppm and about 8.0 ppm, between about 8.0 ppm and about 10 ppm, between about 10 ppm and about 15 ppm, between about 15 ppm and about 20 ppm, between about 20 ppm and about 30 ppm, or between about 30 ppm and about 50 ppm (and overlapping ranges thereof) to reduce the production of non-PHA materials relative to the production of PHA materials in a culture. In one embodiment, the concentration of oxygen or dissolved oxygen is manipulated to between about 0.01 ppm and about 0.05 ppm, between about 0.05 ppm and about 0.1 ppm, between about 0.1 ppm and about 0.5 ppm, between about 0.5 ppm and about 1.0 ppm, between about 1.0 ppm and about 1.5 ppm, between about 1.5 ppm and about 1.75 ppm, between about 1.75 ppm and about 2.0 ppm, between about 2.0 ppm and about 2.5 ppm, between about 2.5 ppm and about 3.0 ppm, between about 3.0 ppm and about 3.5 ppm, between about 3.5 ppm and about 4.0 ppm, between about 4.0 ppm and about 4.5 ppm, between about 4.5 ppm and about 5.0 ppm, between about 5.0 ppm and about 6.0 ppm, between about 6.0 ppm and about 7.0 ppm, between about 7.0 ppm and about 8.0 ppm, between about 8.0 ppm and about 10 ppm, between about 10 ppm and about 15 ppm, between about 15 ppm and about 20 ppm, between about 20 ppm and about 30 ppm, or between about 30 ppm and about 50 ppm (and overlapping ranges thereof) to reduce the production of non-PHA materials relative to the production of PHA materials in a culture. In another embodiment, the concentration of carbon dioxide or dissolved carbon dioxide is manipulated to between about 0.01 ppm and about 0.05 ppm, between about 0.05 ppm and about 0.1 ppm, between about 0.1 ppm and about 0.5 ppm, between about 0.5 ppm and about 1.0 ppm, between about 1.0 ppm and about 1.5 ppm, between about 1.5 ppm and about 1.75 ppm, between about 1.75 ppm and about 2.0 ppm, between about 2.0 ppm and about 2.5 ppm, between about 2.5 ppm and about 3.0 ppm, between about 3.0 ppm and about 3.5 ppm, between about 3.5 ppm and about 4.0 ppm, between about 4.0 ppm and about 4.5 ppm, between about 4.5 ppm and about 5.0 ppm, between about 5.0 ppm and about 6.0 ppm, between about 6.0 ppm and about 7.0 ppm, between about 7.0 ppm and about 8.0 ppm, between about 8.0 ppm and about 10 ppm, between about 10 ppm and about 15 ppm, between about 15 ppm and about 20 ppm, between about 20 ppm and about 30 ppm, or between about 30 ppm and about 50 ppm between about 50 ppm and about 100 ppm, between about 100 ppm and about 200 ppm, between about 200 ppm and about 500 ppm, between about 500 ppm and about 1000 ppm, between about 100 ppm and about 1500 ppm, between about 1500 ppm and about 2000 ppm, between about 2000 ppm and about 3000 ppm, between about 3000 ppm and about 5000 ppm, between about 5000 ppm and about 10,000 ppm, between about 10,000 ppm and about 20,000 ppm (and overlapping ranges thereof) to reduce the production of non-PHA materials relative to the production of PHA materials in a culture. In another embodiment, the concentration of nitrogen or dissolved nitrogen is manipulated to above at least between about 0.01 ppm and about 0.05 ppm, between about 0.05 ppm and about 0.1 ppm, between about 0.1 ppm and about 0.5 ppm, between about 0.5 ppm and about 1.0 ppm, between about 1.0 ppm and about 1.5 ppm, between about 1.5 ppm and about 1.75 ppm, between about 1.75 ppm and about 2.0 ppm, between about 2.0 ppm and about 2.5 ppm, between about 2.5 ppm and about 3.0 ppm, between about 3.0 ppm and about 3.5 ppm, between about 3.5 ppm and about 4.0 ppm, between about 4.0 ppm and about 4.5 ppm, between about 4.5 ppm and about 5.0 ppm, between about 5.0 ppm and about 6.0 ppm, between about 6.0 ppm and about 7.0 ppm, between about 7.0 ppm and about 8.0 ppm, between about 8.0 ppm and about 10 ppm, between about 10 ppm and about 15 ppm, between about 15 ppm and about 20 ppm, between about 20 ppm and about 30 ppm, or between about 30 ppm and about 50 ppm, and overlapping ranges thereof, to reduce the production of non-PHA materials relative to the production of PHA materials in a culture. Without being limited by theory, it is believed that, in some metabolic pathways, an increase in the concentration of methane, oxygen, carbon dioxide, and/or nitrogen causes a metabolic shift that favors the production of PHA at the expense of other non-PHA materials, including a reduction in the production of protein, nucleic acids, polysaccharides, sugars, and/or lipids, particularly, but not necessarily, under growth-limiting, that is, PHA synthesis, conditions. In one embodiment, the synthesis of polyhydroxyalkanoate (PHA) in a biomass material is effected, comprising the steps of: (a) providing a medium comprising a biomass metabolizing a source of carbon, and (b) increasing or maintaining above a minimum the concentration of an element in the medium to cause the biomass to synthesize PHA or increase the synthesis rate of PHA relative to the synthesis rate of non-PHA material. In one embodiment, the PHA is polyhydroxybutyrate (PHB). In one embodiment, the biomass is one or more microorganisms. In one embodiment, the step of increasing the concentration of the element in the medium causes a reduction in the concentration of sugar, lipids, nucleic acids, saccharides, polysaccharides, and/or pigments in the biomass relative to the concentration of PHA in the biomass. In one embodiment, the element is one or more of the following: phosphorus, phosphate, phosphoric acid, sodium phosphate, disodium phosphate, monosodium phosphate, or potassium phosphate, methane, oxygen, carbon dioxide, hydroxyl ions, hydrogen ion, nitrogen. In one embodiment, the element is one or more of the following: EDTA, citric acid, iron, copper, magnesium, manganese, zinc, calcium, potassium, boron. In one embodiment, the PHA synthesis rate is increased relative to the synthesis rate of PHA in said biomass in the absence of said. In one embodiment, the synthesis of polyhydroxyalkanoate (PHA) in a biomass material is effected, comprising the steps of: (a) providing a medium comprising a biomass and an element, and (b) maintaining above a minimum concentration or increasing the concentration of the element in the medium to cause the biomass material to metabolically synthesize PHA at the expense of alternative biomass energy and/or carbon storage materials. In one embodiment, the element is phosphorus, oxygen, magnesium, calcium, copper, iron, methane, carbon dioxide, or nitrogen. In one embodiment, the element is phosphorus. In one embodiment, the element is oxygen. In one embodiment, the element is magnesium. In one embodiment, the element is calcium. In one embodiment, the element is copper. In one embodiment, the element is iron. In one embodiment, the biomass comprises one or more microorganisms. In one embodiment, one or more microorganisms comprise methanotrophic microorganisms. In one embodiment, one or more microorganisms comprise heterotrophic microorganisms. In one embodiment, one or more microorganisms comprise autotrophic microorganisms. In one embodiment, one or more microorganisms comprise methanogenic microorganisms.

In one embodiment, the invention comprises manipulating the concentration of elements, e.g., copper, iron, phosphorus, oxygen, methane, carbon dioxide, in the culture medium to control the concentration of sMMO and/or pMMO produced by a methanotrophic culture in order to control the relative ratio of sMMO to pMMO in the culture and thereby control the growth conditions, metabolic status, metabolic disposition, and/or specification of PHA produced by the culture. In some embodiments, sMMO is expressed in a range between about 0% and 100% of a methanotrophic culture by dry cell weight, as a percentage of microorganisms expressing sMMO, or as a percentage of total MMO expressed by one or more methanotrophic cells, including between 0% and 1%, between about 1% and about 2%, between about 2% and about 3%, between about 3% and about 5%, between about 5% and about 10%, between about 10% and about 20%, between about 20% and about 30%, between about 30% and about 50%, between about 50% and about 70%, between about 70% and about 80%, between about 80% and about 90%, between about 90% and about 95%, between about 95% and about or 100%, and overlapping ranges thereof. Simultaneously, or independently, in some embodiments, pMMO is expressed in a range between about 0% and 100% of a methanotrophic culture by dry cell weight, as a percentage of microorganisms expressing pMMO, or as a percentage of total MMO expressed by one or more methanotrophic cells, including between 0% and 1%, between about 1% and about 2%, between about 2% and about 3%, between about 3% and about 5%, between about 5% and about 10%, between about 10% and about 20%, between about 20% and about 30%, between about 30% and about 50%, between about 50% and about 70%, between about 70% and about 80%, between about 80% and about 90%, between about 90% and about 95%, between about 95% and about or 100%, and overlapping ranges thereof. In some embodiments, the ratio of sMMO to pMMO produced in a methanotrophic culture is controlled to control the specification of PHA produced by a culture In some embodiments, the relative weight ratio of sMMO to pMMO in a methanotrophic culture is at least or approximately 0 to 1, approximately 0.0000001 to 1, approximately 0.0001 to 1, approximately 0.001 to 1, approximately 0.01 to 1, approximately 0.1 to 1, approximately 1 to 1, approximately 2 to 1, approximately 3 to 1, approximately 5 to 1, approximately 10 to 1, approximately 15 to 1, approximately 20 to 1, approximately 25 to 1, approximately 30 to 1, approximately 35 to 1, approximately 50 to 1, approximately 65 to 1, approximately 70 to 1, approximately 80 to 1, approximately 90 to 1, approximately 95 to 1, approximately 98 to 1, approximately 99 to 1, approximately 100 to 1, approximately 1000 to 1, approximately 10,000 to 1, approximately 100,000 to 1, or approximately 1,000,000 to 1, respectively. In some embodiments, the relative weight ratio of pMMO to sMMO in a methanotrophic culture is approximately 0 to 1, approximately 0.0000001 to 1, approximately 0.0001 to 1, approximately 0.001 to 1, approximately 0.01 to 1, approximately 0.1 to 1, approximately 1 to 1, approximately 2 to 1, approximately 3 to 1, approximately 5 to 1, approximately 10 to 1, approximately 15 to 1, approximately 20 to 1, approximately 25 to 1, approximately 30 to 1, approximately 35 to 1, approximately 50 to 1, approximately 65 to 1, approximately 70 to 1, approximately 80 to 1, approximately 90 to 1, approximately 95 to 1, approximately 98 to 1, approximately 99 to 1, approximately 100 to 1, approximately 1000 to 1, approximately 10,000 to 1, approximately 100,000 to 1, or approximately 1,000,000 to 1. In some embodiments, controlling the relative concentrations of sMMO and pMMO produced by a culture of methanotrophic microorganisms, it is possible to control the metabolic status of the culture and thereby control the type of PHA and other cellular material produced by the culture, particularly in the presence of volatile organic compounds, fatty acids, volatile fatty acids, methanol, formate, acetate, dissolved carbon dioxide, dissolved methane, dissolved oxygen, and other elements or compounds that impact the metabolism of a culture of methanotrophic microorganisms in a certain manner according to the relative concentration of sMMO or pMMO in such a culture. In some embodiments, sMMO and/or pMMO is expressed in a range between about 0% and 100% of a methanotrophic culture by dry cell weight, as a percentage of microorganisms expressing sMMO or pMMO, or as a percentage of total MMO expressed by one or more methanotrophic cells, including between 0% and 1%, between about 1% and about 2%, between about 2% and about 3%, between about 3% and about 5%, between about 5% and about 10%, between about 10% and about 20%, between about 20% and about 30%, between about 30% and about 50%, between about 50% and about 70%, between about 70% and about 80%, between about 80% and about 90%, between about 90% and about 95%, between about 95% and about or 100%, and overlapping ranges thereof prior to, during, throughout, or after a PHA production phase. In one embodiment, sMMO is not expressed, or is expressed in low concentrations, in a methanotrophic culture prior to, during, throughout, or after a PHA production phase. Without being limited by theory, it is believed that the directed or controlled absence or reduction of sMMO in a methanotrophic culture producing PHA, particularly in the presence of non-methane organic compounds that can be metabolized by methanotrophic microorganisms, engenders PHA production stability, consistency, and control by selectively shielding against the metabolism of one or some or many non-methane compounds that might otherwise be metabolized in the presence of sMMO, which enables the metabolism of a larger group of non-methane compounds than pMMO. Similarly, in one embodiment, pMMO is not expressed, or is expressed in low concentrations, in a methanotrophic culture prior to, during, throughout, or after a PHA production phase. In some embodiments, the directed or controlled absence or reduction of pMMO in a methanotrophic culture producing PHA, particularly in the presence of non-methane organic compounds that can be metabolized by methanotrophic microorganisms, engenders PHA production stability, consistency, and control by selectively inducing or promoting the metabolism of one or some or many non-methane compounds that might otherwise be not be metabolized using pMMO. In some embodiments, in some methanotrophic cultures, sMMO promotes PHA synthesis at high intracellular concentrations by reducing cellular production of non-PHA materials, particularly as compared to PHA synthesis using pMMO. By controlling the concentration of sMMO relative to pMMO in a methanotrophic microorganism culture in the presence of methane and/or non-methane organic compounds, including VOCs and other carbon-containing materials, such as volatile fatty acids, acetone, acetic acid, acetate, formate, formic acid, chloroform, methylene chloride, carbon dioxide, ethane, and/or propane, it is possible to control the specification or type of PHA produced by the culture, including the molecular weight, polydispersity, melt flow, impact strength, and other similar functional characteristics. In some embodiments, it is preferable to maintain the concentration of copper in the culture media in order to promote sMMO production. In some embodiments, in some methanotrophic cultures, the production of sMMO in many, most, or substantially all of the methanotrophic cells enables the culture to produce more PHA when subject to a nutrient limiting step than would otherwise be produced if the relative ratio of pMMO in the culture was higher prior to the nutrient limiting step. Conversely, in some embodiments, it is preferable to maintain the concentration of copper in the culture media in order to promote pMMO production. In some embodiments, in some methanotrophic cultures, the production of pMMO in many, most, or substantially (e.g., more than 50%, more than 60%, more than 70%, more than 80%, more than 90%, or more) all of the methanotrophic cells enables the culture to produce more PHA when subject to a nutrient limiting step than would otherwise be produced if the relative ratio of sMMO in the culture was higher prior to the nutrient limiting step. In one embodiment, one or more methanotrophic cells or cultures are subject to repeated growth and PHA synthesis cycles or steps, wherein the relative concentration of sMMO to pMMO in the cells or cultures are caused to remain approximately similar or the same in each new cycle or step in order to control the specification and/or functionality of the PHA produced by the culture. In several embodiments, the relative concentration of sMMO to pMMO is variable across the repetitions. In some embodiments, the ratio of relative concentrations decreases (e.g., there is progressively less sMMO and progressively more pMMO with each repetition). In one embodiment, the functional characteristics of PHA produced by a methanotrophic culture exposed to methane emissions comprising methane, carbon dioxide, and one or more volatile organic compounds are controlled and optimized, wherein the method comprises: (a) providing a methanotrophic culture in a mineral medium comprising nutrients, (b) controlling the concentration of one or more of nutrients in the medium to cause the culture to produce a defined relative ratio of sMMO to pMMO, (c) and controlling the concentration of the nutrients in the medium to cause the culture to produce PHA. In one embodiment, the culture produces essentially only pMMO. As used herein, the term "essentially only" shall be given its ordinary meaning and shall also refer to production of pMMO or sMMO in an amount greater than about 50%, greater than about 55%, greater than about 60%, greater than about 65%, greater than about 70%, greater than about 75%, greater than about 80%, greater than about 85%, greater than about 90%, greater than about 95%, greater than about 97%, or greater than about 99% of the monooxygenase produced by a culture. In other embodiments, essentially only shall refer to the ratio of production of pMMO to sMMO. In some embodiments wherein a culture is producing essentially only pMMO, the ration of pMMO to sMMO is about 2:1, about 5:1, about 10:1 about 50:1, about 100:1, about 250:1, about 500:1, about 1000:1, about 2500:1, about 5000:1, about 10,000:1, or greater. In still additional embodiments, the culture may produce both sMMO and pMMO, but with respect to the activity of the enzymes, the culture produces PHA essentially only through the pMMO-mediated pathway. In one embodiment, therefore, even if the culture comprises an equal concentration of sMMO and pMMO, PHA may be preferentially produced via pMMO. In other embodiments, depending on the culture conditions and/or the microorganism strain, the inverse can occur (e.g., the culture produces essentially only sMMO). In one embodiment, the concentration of sMMO in the culture is more than 2 times greater than the concentration of pMMO in the culture. In one embodiment, the concentration of sMMO is more than 5 times greater than the concentration of pMMO in the culture. In one embodiment, the concentration of sMMO is more than 10 times greater than the concentration of pMMO in culture. In one embodiment, the concentration of pMMO is more than 2 times greater than the concentration of sMMO in said culture. In one embodiment, the concentration of pMMO is more than 5 times greater than the concentration of sMMO in said culture. In one embodiment, steps (a) through (c) are repeated, wherein the concentration of sMMO relative to pMMO in the culture is substantially the same (e.g., within 5%, 10%, 25%, 50% or 75% relative proportion by weight) in step (c) in at least two repetitions.

In one embodiment, a method is provided for converting a carbon-containing gas or material into a polyhydroxyalkanoate (PHA) at high efficiency, comprising: (a) providing a methanotrophic culture, (b) providing a medium comprising one or more nutrient comprising a carbon-containing material that can be metabolized by the culture, (c) controlling the concentration of the one or more nutrient in the medium to cause the cellular replication of one or more microorganisms in the culture wherein the gene encoding the soluble methane monooxygenase enzyme is absent in the one or more microorganisms, (d) controlling the concentration of the one or more nutrients in the medium to cause the culture to produce PHA, and (e) repeating steps (a) through (d). Copper is a critical component of many methanotrophic systems, including both sMMO and pMMO, and copper typically controls the switch between sMMO and pMMO production. Reducing copper concentration (below 0.1, 1, 2, 4, 10, 20, 40, 100 micromolar, below 0.001, 0.01, 0.1, 1, 2, 4, 8, 10, 15, 20, 40, 100, 200 mg/L, or below 0.001, 0.01, 0.1, 1, 2, 4, 10, 100 mg/g dry weight of microorganism biomass) typically increases sMMO production, while increasing copper concentration (above 0.1, 1, 2, 4, 10, 20, 40, 100 micromolar, above 0.001, 0.01, 0.1, 1, 2, 4, 8, 10, 15, 20, 40, 100, 200 mg/L, or, or above 0.001, 0.01, 0.1, 1, 2, 4, 10, 100 mg/g dry weight of microorganism biomass) typically increases pMMO production. Copper is generally added to a culture each time water or mineral media is added to a culture, since trace copper is difficult to remove from even purified water, and copper is needed for methanotrophic cellular replication/growth, since MMO generally drives the oxidation of methane to biomass, and MMO is a copper-containing enzyme. Applicant has surprisingly discovered that microorganisms that do not possess or express the gene for sMMO unexpectedly produce PHA at high efficiency, and can be selectively cultured, using culture selection pressures, to out-compete microorganisms that do possess or express the gene for sMMO (particularly in non-sterile systems, wherein new microorganisms are periodically introduced to the culture) by limiting, controlling, or reducing copper concentrations and simultaneously subjecting the culture to growth-polymerization-growth repetitions, as described herein. In one embodiment, microorganisms that possess higher concentrations of PHA switch from polymerization to growth mode (wherein the microorganisms produce soluble and/or particulate methane monooxygenase) more quickly and efficiently than microorganisms that possess lower concentrations of PHA, and/or carry out cellular replication more efficiently in general; by reducing copper concentrations to levels that would traditionally cause the culture to express sMMO (e.g., less than 0.001, 0.01, 0.1, 1, 10, or 100 mg/L, or less than 0.01, 0.1, 1, 10, or 100 micromolar, or less than 0.001, 0.01, 0.1, 1, 10, or 100 mg per gram microorganism dry weight) while also cycling between growth and polymerization cycles, microorganisms that produce high concentrations of PHA and also grow quickly in low copper concentrations out-compete microorganisms that produce less PHA and grow slower in low copper concentrations. Since pMMO renders a faster metabolism than sMMO, by reducing the copper concentration in the medium (permanently or temporarily) to traditionally sMMO-generating concentrations, and concurrently subjecting a culture to growth-polymerization-growth repetitions which select for microorganisms that generate high PHA concentrations and metabolize efficiently in transitioning from polymerization mode to growth mode, Applicant has discovered that a high-efficiency microorganism can be selectively produced and maintained, including in non-sterile conditions, that does not contain or express the genetic coding for sMMO, accumulates high concentrations of PHA, and out-competes microorganisms that produce sMMO. The ability to cause a methanotrophic culture to generate microorganisms that do not possess or express the gene encoding sMMO by reducing copper concentrations is a surprising and unexpected result, and offers a range of advantages, including superior process stability (microorganisms produce only pMMO, regardless of copper concentration), PHA consistency (the metabolic pathway, pMMO, is unchanging, thereby controlling the characteristics of PHA produced, such as monomer composition, molecular weight, polydispersity, elongation, modulus, viscosity), and increased metabolic efficiency (e.g., rate, oxidation, metabolism, copper requirements). In addition to copper, other nutrients can be used, either individually or in combination, in similar fashion to control for the selective production of microorganisms that do not possess or express the gene encoding soluble methane monooxygenase, such nutrients including: methane, oxygen, phosphorus, magnesium, iron, boron, aluminum, calcium, cobalt, chloride, chromium, EDTA, manganese, molybdenum, sulfur, nickel, zinc, and/or potassium. In one embodiment, more than 10%, 25%, 50%, 75%, or 80% of the culture does not contain or express the gene encoding soluble methane monooxygenase.

In one embodiment, a method is provided for converting a carbon-containing material (e.g., methane, carbon dioxide, propane, ethane, acetone, acetate, formaldehyde, a volatile organic compound, a non-methane organic compound, carbon dioxide) into a polyhydroxyalkanoate (PHA), the method comprising: (a) providing a methanotrophic culture, (b) providing a medium comprising one or more nutrient comprising a carbon-containing material that can be metabolized by the culture, (c) controlling the concentration of the one or more nutrient in the medium to cause the cellular replication of the culture w wherein the gene encoding the ethylmalonyl-CoA pathway is present or expressed in one or more microorganism in said culture, (d) controlling the concentration of said one or more nutrients in said medium to cause said culture to produce PHA, and (e) repeating steps (a) through (d). Applicant has surprisingly discovered that the ethylmalonyl-CoA (EMC) pathway, combined with required and controlled conditions, enables the production of over 50%, 55%, 60%, 65%, 70%, 80%, 85%, 90%, and 95% intracellular PHA concentrations. Applicant has also surprisingly discovered that the ethylmalonyl-CoA (EMC) pathway can enable methanotrophic microorganisms to switch from growth to PHA polymerization and back to growth at high efficiency (that is, at higher efficiency than microorganisms that do not express or utilize the EMC pathway) even when intracellular PHA concentrations exceed over 50%, 55%, 60%, 65%, 70%, 80%, 85%, 90%, and 95% by weight, whereas many cultures with PHA concentrations exceeding 50%, 60%, or 70% cannot effectively return to growth mode following a polymerization period. In several embodiments, the increased growth efficiency of microorganisms expressing the EMC pathway (as compared to those microorganisms that do not express the pathway) is greater than about 1.1-fold, 1.2-fold, 1.5-fold, 2-fold, about 4-fold, about 6-fold, about 8-fold, about 10-fold, or greater. Thus, by subjecting a culture to growth-polymerization-growth cycling, Applicant has found that it is possible to select for preferential growth of microorganisms that possess the gene encoding the EMC pathway. In addition, Applicant has surprisingly discovered that it is possible to selectively produce a culture of microorganisms that express the EMC pathway in sterile or non-sterile conditions, including in the presence of methane, non-methane carbon-containing materials, or other materials that influence the metabolism of the microorganisms, by simultaneously subjecting the culture to growth-PHA polymerization-growth cycling, as described herein, while also controlling the concentration one or more nutrients available to the culture. In one embodiment, the concentration of a nutrient, such as copper, is controlled to selectively favor the production of EMC-pathway microorganisms. In some embodiments, microorganisms that do not possess or express the genetic material encoding soluble methane monooxygenase also possess the genes encoding the EMC-pathway. As used herein the terms "genetic material" and "nucleic acid" shall be given their ordinary meanings and shall also refer to polymer of nucleotides. Non-limiting examples thereof include DNA (e.g. genomic DNA, cDNA), RNA molecules (e.g. mRNA) and chimeras thereof. The nucleic acid molecule can be obtained by cloning techniques or synthesized. DNA can be double-stranded or single-stranded (coding strand or non-coding strand (e.g., anti-sense)). Also, as used herein, the term "expression" shall be given its ordinary meaning and shall be understood to define the process by which a gene is transcribed into mRNA (transcription) and the mRNA is then be translated (translation) into one polypeptide (or protein) or more.

Thus, as described herein, by subjecting the culture to growth-polymerization-growth (GPG) cycling while also controlling or reducing the concentration of copper, or other nutrients that impact the switch between sMMO and pMMO production, it is possible to selectively produce microorganisms that do not possess or express the genetic material encoding soluble methane monooxygenase but do possess the gene encoding the EMC pathway. The ability to selectively produce microorganisms that contain or express the genes encoding the EMC pathway and/or do not contain or express the genes encoding sMMO offers significant process advantages, including process stability (microorganisms produce consistent concentrations of PHA and produce only pMMO, regardless of copper concentration or microorganism contamination), PHA consistency (the metabolic pathway is unchanging, thereby controlling the characteristics of PHA produced, such as monomer composition, molecular weight, polydispersity, elongation, modulus, viscosity), and increased metabolic efficiency (e.g., rate, oxidation, metabolism, nutrient requirements). In some embodiments, such microorganisms and processes may be combined with other microorganisms and processes, wherein a culture may contain microorganisms containing genes encoding or expressing both sMMO and pMMO and genetic packages that do not encode or express the EMC pathway; in some embodiments, microorganisms that do not possess or express one or more gene encoding sMMO comprise less than 1%, less than 5%, less than 10%, less than 20%, less than 50%, less than 75%, more than 75% of a culture; in other embodiments, microorganisms that contain or express genetic material encoding the EMC pathway comprise less than 1%, less than 5%, less than 10%, less than 20%, less than 50%, less than 75%, more than 75% of a culture.

In one embodiment, a method is provided for converting a carbon-containing gas or material into a polyhydroxyalkanoate (PHA) at high efficiency, comprising: (a) providing a methanotrophic culture, (b) providing a medium comprising one or more nutrient comprising a carbon-containing material that can be metabolized by the culture, (c) controlling the concentration of the one or more nutrient in the medium to cause the cellular replication of one or more microorganisms in the culture wherein the gene encoding the soluble methane monooxygenase enzyme is absent in the one or more microorganisms, (d) controlling the concentration of the one or more nutrients in the medium to cause the culture to produce PHA, and (e) repeating steps (a) through (d). Copper is a critical component of many methanotrophic systems, including both sMMO and pMMO, and copper typically controls the switch between sMMO and pMMO production. In several embodiments, reducing copper concentration (below about 0.1, about 1, about 2, about 4, about 10, about 20, about 40, about 100 micromolar, below about 0.0001, about 0.001, about 0.01, about 1, about 2, about 4, about 8, about 10, about 15, about 20, about 40, about 100, about 200 mg/L, or below about 0.001, about 0.01, about 0.1, about 1, about 2, about 4, about 10, about 100 mg/g dry weight of microorganism biomass) typically (or for at least some methanotrophic microorganisms) increases sMMO production. In contrast, increasing copper concentration (above about 0.1, about 1, about 2, about 4, about 10, about 20, about 40, about 100 micromolar, above about 0.001, about 0.01, about 0.1, about 1, about 2, about 4, about 8, about 10, about 15, about 20, about 40, about 100, about 200 mg/L, or, or above about 0.001, about 0.01, about 0.1, about 1, about 2, about 4, about 10, about 100 mg/g dry weight of microorganism biomass) typically (or for at least some methanotrophic microorganisms) increases pMMO production. Copper is generally added to a culture each time water or mineral media is added to a culture, since trace copper is difficult to remove from even purified water, and copper is needed for methanotrophic cellular replication/growth, since MMO generally drives the oxidation of methane to biomass, and MMO is a copper-containing enzyme.

In accordance with several embodiments, Applicant has surprisingly discovered that selective culture conditions can be employed that allow for the dominance of a culture by microorganisms that utilize the pMMO pathway, even at low or reduced copper concentrations (e.g., those conditions in which sMMO would typically be produced). In some embodiments, the pMMO pathway or enzyme is the exclusive pathway or enzyme expressed or used in the microorganism for the production of methane monooxygenase (e.g., the selective pressures of the processes disclosed herein induce a loss of the genetic material encoding the sMMO gene in the culture or microorganism over time, or the selective pressures result in the dominance or growth or metabolic success of microorganisms that do not possess or express the genetic material used for sMMO production). In some embodiments, the pMMO pathway is either preferentially expressed or preferentially active in the culture, such that the microorganisms still retain the genetic material necessary to produce sMMO, but sMMO is either not produced, produced but not used, produced and functionally blocked (e.g., negative feedback mechanisms), produced and functionally deficient under the culture conditions, and/or produced but metabolically outcompeted for substrate by pMMO enzymes. Thus, in several embodiments, microorganisms that have reduced sMMO expression or function unexpectedly produce PHA at high efficiency, and can be selectively cultured, using culture selection pressures, to out-compete microorganisms that do express sMMO (particularly in non-sterile systems, wherein new microorganisms are periodically introduced to the culture) by limiting, controlling, or reducing copper concentrations and simultaneously subjecting the culture to growth-polymerization-growth repetitions, as described herein.

In one embodiment, microorganisms that possess higher concentrations of PHA switch from polymerization to growth mode (wherein the microorganisms produce soluble and/or particulate methane monooxygenase) more quickly and efficiently than microorganisms that possess lower concentrations of PHA, and/or carry out cellular replication more efficiently in general. By reducing copper concentrations to levels that would cause or enable, or traditionally cause or enable, the culture, or at least one or more methanotrophic microorganisms, to express sMMO (e.g., less than about 0.001, about 0.01, about 0.1, about 1, about 10, or about 100 mg/L, or less than about 0.01, about 0.1, about 1, about 10, or about 100 micromolar, or less than about 0.001, about 0.01, about 0.1, about 1, about 10, or about 100 mg per gram microorganism dry weight) while also cycling between growth and polymerization cycles, microorganisms that produce high concentrations of PHA and also grow quickly in low copper concentrations out-compete microorganisms that produce less PHA and grow slower in low copper concentrations. Since pMMO renders a faster metabolism than sMMO, by reducing the copper concentration in the medium (permanently or temporarily) as compared to traditionally pMMO-generating copper concentrations (e.g., to concentrations that could enable or induce one or more methanotrophic microorganisms to produce sMMO if present in the medium), and concurrently (or subsequently) subjecting a culture to growth-polymerization-growth repetitions which select for microorganisms that generate high PHA concentrations and metabolize efficiently in transitioning from polymerization mode to growth mode, Applicant has discovered that a high-efficiency microorganism can be selectively produced and maintained (even in non-sterile conditions) that either does not contain, does not express, does not produce, or expresses or produces at reduced levels sMMO, accumulates high concentrations of PHA, and out-competes microorganisms that produce sMMO. The ability to cause a methanotrophic culture to generate microorganisms that do not possess the genetic material encoding sMMO or express sMMO at reduced levels (or reduced functionality) by reducing copper concentrations is a surprising and unexpected result, and offers a range of advantages. For example, superior process stability (microorganisms produce only pMMO, regardless of copper concentration), PHA consistency (the metabolic pathway, pMMO, is unchanging, thereby controlling the characteristics of PHA produced, such as monomer composition, molecular weight, polydispersity, elongation, modulus, viscosity), and increased metabolic efficiency (e.g., rate, oxidation, metabolism, copper requirements) are achieved. In addition to copper, other nutrients can be used, either individually or in combination, in similar fashion to control for the selective production of microorganisms that do not possess or express the gene encoding soluble methane monooxygenase, such nutrients including: methane, oxygen, phosphorus, magnesium, iron, boron, aluminum, calcium, cobalt, chloride, chromium, EDTA, manganese, molybdenum, sulfur, nickel, zinc, and/or potassium. In one embodiment, more than 10%, 25%, 50%, 75%, or 80% of the culture does not contain the gene encoding soluble methane monooxygenase.

In one embodiment, a method is provided for converting a carbon-containing material (e.g., methane, carbon dioxide, propane, ethane, acetone, acetate, formaldehyde, a volatile organic compound, a non-methane organic compound, carbon dioxide) into a polyhydroxyalkanoate (PHA), the method comprising: (a) providing a methanotrophic culture, (b) providing a medium comprising one or more nutrient comprising a carbon-containing material that can be metabolized by the culture, (c) controlling the concentration of the one or more nutrient in the medium to cause the cellular replication of the culture wherein the genetic material encoding the ethylmalonyl-CoA (EMC) pathway (e.g., the various enzymes or co-factors that are involved in the pathway) is present in one or more microorganism in said culture, (d) controlling the concentration of said one or more nutrients in said medium to cause said culture to produce PHA, and (e) repeating steps (a) through (d). Applicant has surprisingly discovered that the EMC pathway, combined with required and controlled conditions, enables the production of over 50%, 55%, 60%, 65%, 70%, 80%, 85%, 90%, and 95% intracellular PHA concentrations. Applicant has also surprisingly discovered that the microorganisms using the EMC pathway can be switched from growth conditions or metabolism to PHA polymerization conditions or metabolism and back to growth conditions or metabolism at high efficiency, even when intracellular PHA concentrations exceed over 50%, 55%, 60%, 65%, 70%, 80%, 85%, 90%, and 95% by weight, whereas many cultures with PHA concentrations exceeding 50%, 60%, or 70% cannot effectively return to growth mode following a polymerization period. Thus, by subjecting a culture to growth-polymerization-growth cycling, Applicant has found that it is possible to select for microorganisms that possess the gene encoding the EMC pathway. In addition, Applicant has surprisingly discovered that it is possible to selectively produce a culture of microorganisms that express the EMC pathway in sterile or non-sterile conditions, including in the presence of methane, non-methane carbon-containing materials, or other materials that influence the metabolism of the microorganisms, by simultaneously subjecting the culture to growth-PHA polymerization-growth cycling, as described herein, while also controlling the concentration one or more nutrients available to the culture. In one embodiment, the concentration of a nutrient, such as copper, is controlled to selectively favor the production of EMC-pathway microorganisms. In some embodiments, microorganisms that do not possess the genetic material encoding soluble methane monooxygenase (or have the genetic material but express at reduced levels or at reduced levels of activity) also possess the genes encoding the EMC-pathway. Thus, as described herein, by subjecting the culture to growth-polymerization-growth (GPG) cycling while also controlling or reducing the concentration of copper, or other nutrients that impact the switch between sMMO and pMMO production, it is possible to selectively produce microorganisms that do not possess the gene encoding soluble methane monooxygenase (or have the genetic material but express sMMO at reduced levels or at reduced levels of activity) but do possess the gene encoding the EMC pathway. The ability to selectively produce microorganisms that contain the genetic material for and express the gene encoding the EMC pathway and/or do not contain the genetic material for or do not express the gene encoding sMMO offers significant process advantages, including process stability (microorganisms produce consistent concentrations of PHA and produce only pMMO, regardless of copper concentration or microorganism contamination), PHA consistency (the metabolic pathway, is unchanging, thereby controlling the characteristics of PHA produced, such as monomer composition, molecular weight, polydispersity, elongation, modulus, viscosity), and increased metabolic efficiency (e.g., rate, oxidation, metabolism, nutrient requirements). In some embodiments, such microorganisms and processes may be combined with other microorganisms and processes, wherein a culture may contain microorganisms containing genes encoding both sMMO and pMMO and genetic material that does not include material encoding the EMC pathway; in some embodiments, microorganisms that do not possess gene(s) encoding sMMO comprise less than about 1%, less than about 5%, less than about 10%, less than about 20%, less than about 50%, less than about 75%. In other embodiments, microorganisms that contain genetic material encoding the EMC pathway comprise less than about 1%, less than about 5%, less than about 10%, less than about 20%, less than about 50%, or less than about 75%. In some embodiments, microorganisms and processes may be combined with other microorganisms and processes, wherein a culture may contain microorganisms containing genes encoding both sMMO and pMMO and genetic material that does not include material encoding the EMC pathway. In several embodiments, additional selection methods, and/or "spiking" of a culture with microorganisms of a certain type or genetic makeup can be used to achieve microorganism cultures with desired characteristics/demographics.

Several embodiments of the invention comprise a culture or bacterium, or an isolated culture or bacterium, that (a) does not express or contain the genetic material encoding soluble methane monooxygenase, (b) expresses or contains the genetic material encoding the ethylmalonyl-CoA pathway, and (c) produces polyhydroxyalkanoate (PHA) at intracellular concentrations wherein the ratio of PHA to non-PHA biomass exceeds 3:1 on a dry weight basis (e.g., wherein the concentration of PHA exceeds 75% on a total dry cell weight basis). In some embodiments, such culture or bacterium may be mixed with other cultures or bacteria, wherein such culture or bacterium comprise, consists essentially of, or substantially exhibits the properties (a), (b), and (c). In several embodiments, the processes and methods disclosed herein are utilized to produce such cultures and/or bacterium, including as part of a process to produce PHA, including as a measure to continually drive selection pressures to produce such cultures and/or bacterium, particularly, in some embodiments, in the presence of non-sterile input streams. In some embodiments, such culture(s) or bacterium is selected from a group consisting of: *Methylosinus*, *Methylocystis*, *Methylococcus*, *Methylobacterium*, and *Pseudomonas*. In some embodiments, the invention comprises the PHA produced by such a culture or bacterium, and/or the PHA comprising such a culture or bacterium.

Some embodiments of the invention comprise a methanotrophic culture or bacterium having (a) particulate methane monooxygenase activity in the presence of copper ion concentrations between concentrations that can generate soluble methane monooxygenase in some methanotrophs, including 0.001 micromolar and 1000 micromolar, (b) ethylmalonyl-CoA pathway expression in the presence of copper concentrations between 0.001 micromolar and 1000 micromolar, and (c) intracellular concentrations of polyhydroxyalkanoate (PHA) wherein the ratio of PHA to non-PHA biomass exceeds 2.9:1 on a dry weight basis (e.g., greater than 25%, greater than 55%, greater than 59%, greater than 71%, greater than 72.5%, greater than 80%, greater than 85%, greater than 87%, greater than 90%, greater than 95%, greater than 98% as function of total dry cell weight). In some embodiment, such culture(s) or bacterium are selected from a group consisting of: *Methylosinus*, *Methylocystis*, *Methylococcus*, *Methylobacterium*, and *Pseudomonas*. In some embodiments, such culture of bacterium is a Type I, Type II, or Type X methanotroph. In some embodiments, such culture of bacterium is a Type I methanotroph. In some embodiments, such culture of bacterium is a Type II methanotroph. In some embodiments, such culture of bacterium is a Type X methanotroph. In some embodiments, such culture of bacterium is from a *Methylosinus*, *Methylocystis*, or *Methylococcus* genus. In some embodiments, such culture of bacterium is from a *Methylosinus* genus. In some embodiments, such culture of bacterium is from a *Methylocystis* genus. In some embodiments, such culture of bacterium is from a *Methylococcus* genus. In several embodiments, the processes and methods disclosed herein are utilized to produce such cultures and/or bacterium, including as part of a process to produce PHA, including as a measure to continually drive selection pressures to produce such cultures and/or bacterium, particularly, in some embodiments, in the presence of non-sterile input streams. In some embodiments, such culture or bacterium is a mutant, genetically-engineered mutant, genetically-manipulated variant, and/or selection-pressure-induced mutant selected from a group consisting of: *Methylosinus*, *Methylocystis*, *Methylococcus*, *Methylobacterium*, and *Pseudomonas*. In some embodiments, such culture of bacterium is a mutant of a strain in the *Methylosinus* genus. In some embodiments, such culture of bacterium is a mutant of a strain in the *Methylocystis* genus. In some embodiments, such culture of bacterium is a mutant of a strain in the *Methylococcus* genus. In some embodiments, such culture of bacterium is a mutant of a strain in the *Methylobacterium* genus. In some embodiments, such culture of bacterium is a mutant of a strain in the *Pseudomonas* genus. In some embodiments, the invention comprises the PHA produced by such a culture or bacterium, and/or the PHA comprising such a culture or bacterium.

In some embodiments, the invention comprises a method for producing or mutating a methanotrophic culture or bacterium that can produce polyhydroxyalkanoate (PHA) at intracellular concentrations exceeding 71% by weight in a non-sterile environment, the method comprising: (a) providing a culture broth comprising methane, a medium comprising one or more nutrients comprising copper, and a methanotrophic culture or bacterium; (b) controlling the concentration of copper in the medium to a concentration that can enable methanotrophic microorganisms to produce sMMO (e.g. less than 0.001, 0.01, 0.1, 1, 2, 5, 10, or 50 micromolar, or less than 0.001, 0.01, 0.1, 1, 2, 5, 10, 50, or 100 mg/cell dry weight, depending on the culture strain), (c) reducing the concentration of one or more nutrient in said medium (e.g., nitrogen, oxygen, magnesium, phosphate, sulfate) to cause said culture or bacterium to produce PHA, (d) increasing the concentration of said one or more nutrient of step (c) to cause said culture or bacterium to reproduce using essentially only pMMO, and (e) subjecting said culture or bacterium to a repetition of steps (b), (c), and (d). In some embodiments, the invention comprises the PHA of the culture or bacterium of such a process, and/or the PHA comprising the culture or bacterium of such a process.

In some embodiments, the invention comprises using microorganisms to produce polyhydroxyalkanoate (PHA) comprising methanotrophic microorganisms having the following characteristics: (a) the microorganisms produce no soluble methane monooxygenase, or no perceptible soluble methane monooxygenase, at any copper concentration (e.g., at non-detectable concentrations), or do not express or contain the genetic material encoding soluble methane monooxygenase; (b) the microorganisms express the ethylmalonyl-CoA metabolic pathway; and (c) the microorganisms produce polyhydroxyalkanoate at intracellular concentrations exceeding 57% by dry weight, wherein the microorganisms are selected from the a group consisting of *Methylosinus*, *Methylocystis*, *Methylococcus*, *Methylobacterium*, and *Pseudomonas*.

In some embodiments, the invention comprises using microorganisms to produce polyhydroxyalkanoate (PHA) comprising methanotrophic microorganisms having the following characteristics: (a) the microorganisms produce no soluble methane monooxygenase, or no perceptible soluble methane monooxygenase, at any copper concentration (e.g., at non-detectable concentrations), or do not express or contain the genetic material encoding soluble methane monooxygenase; (b) the microorganisms express the ethylmalonyl-CoA metabolic pathway; and (c) the microorganisms produce polyhydroxyalkanoate at intracellular concentrations exceeding 71% by dry weight, wherein the microorganisms are selected from the a group consisting of *Methylosinus*, *Methylocystis*, *Methylococcus*, *Methylobacterium*, and *Pseudomonas*.

In some embodiments, the invention comprises using microorganisms to produce polyhydroxyalkanoate (PHA) comprising methanotrophic microorganisms having the following characteristics: (a) the microorganisms produce no soluble methane monooxygenase, or no perceptible soluble methane monooxygenase, at any copper concentration (e.g., at non-detectable concentrations), or do not express or contain the genetic material encoding soluble methane monooxygenase; (b) the microorganisms express the ethylmalonyl-CoA metabolic pathway; and (c) the microorganisms produce polyhydroxyalkanoate at intracellular concentrations exceeding 23% by dry weight, wherein the microorganisms are selected from the a group consisting of *Methylosinus*, *Methylocystis*, *Methylococcus*, *Methylobacterium*, and *Pseudomonas*.

In some embodiments, the invention comprises using microorganisms to produce polyhydroxyalkanoate (PHA) comprising methanotrophic microorganisms having the following characteristics: (a) the microorganisms produce no soluble methane monooxygenase, or no perceptible soluble methane monooxygenase, at any copper concentration (e.g., at non-detectable concentrations), or do not express or contain the genetic material encoding soluble methane monooxygenase; (b) the microorganisms express the ethylmalonyl-CoA metabolic pathway; and (c) the microorganisms produce polyhydroxyalkanoate at intracellular concentrations exceeding 80% by dry weight, wherein the microorganisms are selected from the a group consisting of *Methylosinus*, *Methylocystis*, *Methylococcus*, *Methylobacterium*, and *Pseudomonas*.

In some embodiments, the invention comprises using microorganisms to produce polyhydroxyalkanoate (PHA) comprising methanotrophic microorganisms having the following characteristics: (a) the microorganisms produce no soluble methane monooxygenase, or no perceptible soluble methane monooxygenase, at any copper concentration (e.g., at non-detectable concentrations), or do not express or contain the genetic material encoding soluble methane monooxygenase; (b) the microorganisms express the ethylmalonyl-CoA metabolic pathway; and (c) the microorganisms produce polyhydroxyalkanoate at intracellular concentrations exceeding 85% by dry weight, wherein the microorganisms are selected from the a group consisting of *Methylosinus*, *Methylocystis*, *Methylococcus*, *Methylobacterium*, and *Pseudomonas*.

In some embodiments, the invention comprises using microorganisms to produce polyhydroxyalkanoate (PHA) comprising methanotrophic microorganisms having the following characteristics: (a) the microorganisms produce no soluble methane monooxygenase, or no perceptible soluble methane monooxygenase, at any copper concentration (e.g., at non-detectable concentrations), or do not express or contain the genetic material encoding soluble methane monooxygenase; (b) the microorganisms express the ethylmalonyl-CoA metabolic pathway; and (c) the microorganisms produce polyhydroxyalkanoate at intracellular concentrations exceeding 90% by dry weight, wherein the microorganisms are selected from the a group consisting of *Methylosinus*, *Methylocystis*, *Methylococcus*, *Methylobacterium*, and *Pseudomonas*.

In some embodiments, the invention comprises using microorganisms to produce polyhydroxyalkanoate (PHA) comprising methanotrophic microorganisms having the following characteristics: (a) the microorganisms produce no soluble methane monooxygenase, or no perceptible soluble methane monooxygenase, at any copper concentration (e.g., at non-detectable concentrations), or do not express or contain the genetic material encoding soluble methane monooxygenase; (b) the microorganisms express the ethylmalonyl-CoA metabolic pathway; and (c) the microorganisms produce polyhydroxyalkanoate at intracellular concentrations exceeding 95% by dry weight, wherein the microorganisms are selected from the a group consisting of *Methylosinus*, *Methylocystis*, *Methylococcus*, *Methylobacterium*, and *Pseudomonas*.

In several embodiments of the invention, methanol is added to a culture of methanotrophic microorganisms utilizing a closed loop recycling gas stream comprising methane. In some embodiments, methanotrophic microorganisms are enabled to grow under conditions of, and consume, very low concentrations of methane by co-utilizing methanol as a carbon substrate. In the past, the growth of methanotrophic microorganisms was significantly reduced under low methane concentrations due to, among other things, low mass transfer rates. In some embodiments, by the addition of methanol in a closed loop gas recycling system, it is possible to effect the substantially complete elimination of methane by methanotrophic microorganisms.

In several embodiments of the invention, the diffusion of light is increased in a liquid growth culture media by reducing the density of the liquid in a light path. In some embodiments the culture comprises autotrophic microorganisms. In some embodiments, the application of gas bubbles into the media decreases the relative solids density of the light path, thus enabling an increased diffusion of light into a liquid culture media from a given light intensity energy.

In several embodiments of the invention, a series of submerged light rods are placed into a liquid culture to manipulate or adjust the culture conditions. In some embodiments, the culture comprises autotrophic microorganisms. In some embodiments, the light rods function to diffuse light, diffuse gas, act as static or dynamic mixers, assist in the circulation of a liquid culture media, and/or facilitate heat exchange through the circulation of a gas, liquid, and/or combination thereof.

Traditionally, pH control in a microorganism growth system is difficult and/or costly to maintain. In some embodiments, pH is controlled by varying the nitrogen source supplied to a microorganism growth system between pH-increasing and pH-reducing nitrogen sources, e.g., $NO_3^-$ and $NH_3^+$, respectively. In some embodiments, nitrogen sources are utilized that do not significantly affect the pH of the system, including, when applicable, complex nitrogen sources such as biomass. In additional embodiments, a closed loop system is employed to reduce changes in pH. In some embodiments, respiration-generated carbon dioxide counterbalances increases in pH caused by the utilization of pH-increasing nitrogen sources, such as nitrates. In one embodiment, nitrogen fixation is used to add hydroxyl ions to the culture medium, which may or may not be counterbalanced by the addition of protons from either biological or chemical sources. In one embodiment, nitrate fixation is used to add hydroxyl ions to the culture medium, which may or may not be counterbalanced by the addition of protons from either biological or chemical sources. In one embodiment, ammonia or ammonium fixation is used to add protons to the culture medium, which may or may not be counterbalanced by the addition of hydroxyl ions from either biological or chemical sources.

A number of methods are known for the induction of gas into liquid, including static mixing, ejector mixing, propeller mixing, and/or a combination thereof. Simultaneously, it is also known that shear can be highly detrimental to microorganism growth, and can often impede or permanently deactivate microorganism metabolism. Thus, mass transfer in a gas-based system is often limited by the need to counterbalance sufficient mixing with shear considerations. In several embodiments of the invention, a vessel comprising liquid culture media is mixed with a gas, e.g. methane, under relatively high shear conditions, and then subsequently transferred to a vessel comprising liquid culture media maintained under relatively low shear conditions. In some embodiments, microorganism growth is primarily induced in the low shear vessel. In some embodiments, high gas transfer rates are effected in the first high shear vessel by mixing while performed in the low shear vessel by gaseous diffusion.

In another embodiment, a closed loop gas recycling system is maintained, wherein a vessel comprising gas-utilizing microorganisms is supplied with gas, wherein the gas is utilized by gas-utilizing microorganisms, and wherein the rate at which gas is added to the system is determined by the rate at which the pressure in the vessel changes in accordance with the conversion of gases into metabolic derivatives (such as biomass, carbon dioxide, and water). For example, a vessel containing methane-utilizing microorganisms may be pressurized to 60 psi with a combination of methane and oxygen; as the pressure in the system drops in accordance with the metabolism of the methane-utilizing microorganisms, additional methane and oxygen is added to the system such that the pressure of the vessel remains at 60 psi. In certain embodiments, higher or lower pressures are maintained. In some embodiments, the system is periodically flushed to remove carbon dioxide. In some embodiments, autotrophic microorganisms and a light injection system may be added to the system in order to convert carbon dioxide into additional oxygen, thereby substantially reducing or eliminating the need to flush the system and/or introduce oxygen. In one embodiment, a device is provided that is capable of carrying out gas-based fermentation, methanotrophic metabolism, bioreaction, autotrophic metabolism, heterotrophic metabolism, and/or biocatalyst-based metabolism at high efficiency, particularly using one or more, and particularly at least two gases as nutrient (e.g., carbon and oxygen) input sources, measured in the following terms: 1) gas capture efficiency, 2) mass transfer efficiency (including in terms of the power required to transfer gas into aqueous/dissolved form), and 3) material synthesis (in terms of grams per liter per hour). In one embodiment, a system is provided for gas input reactions (e.g., methane and oxygen; oxygen and carbon dioxide; carbon dioxide and methane; methane, ammonia, and oxygen; methane, ammonia, oxygen, and dinitrogen; methane, carbon dioxide, and oxygen; or various combinations of such input gasses) that utilizes a system comprising multiple reaction vessels. In one embodiment, one or more vessel may be equipped with a rotating mixer. In one embodiment, the rotating mixer may induce cavitation in the liquid medium. In one embodiment, such cavitation may cause acute induction of gas entrainment into the liquid medium, significantly increasing mass transfer induction. In one embodiment, gas may be injected into one or more of the vessels behind the leading edge of a moving material in liquid medium, in order to reduce and then increase the driving pressure of the gas injection. In one embodiment, the pressure of the liquid medium may be pulsed through periods of high pressure and low pressure to increase the mass transfer of gas into liquid medium. In one embodiment, the pulsation of pressure in a liquid medium may be employed, wherein the high pressure (e.g., up to 100 psi) period may have a duration from 0.001 seconds to 25 minutes, and wherein the low pressure period (e.g., from −25 inches vacuum to 5 psi) may have a duration from 0.001 seconds to 25 minutes. In one embodiment, the rapid induction of pressure pulsation may be effected by fitting a vessel with a means of transferring acoustic energy into the vessel medium. In one embodiment, the rapid induction of pressure pulsation may be effected by fitting a vessel with a transducer. In one embodiment, the rapid induction of pressure pulsation may be effected by fitting a vessel with one or more sonication means, wherein the liquid medium is sonicated, wherein such sonication is diffused throughout a volume sufficient to avoid damage to microorganisms or enzymes in the liquid medium. In one embodiment, silica gel or silica-based liquid is added to the liquid medium to increase the solubility of methane and oxygen in the liquid medium. In one embodiment, the reaction vessels comprise fully or partially enclosed vessels. In one embodiment, the reaction vessels comprise fully or partially-enclosed medium-containing volumes or medium-containing compartments, within or in addition to one or more tanks, compartments, vessels, or other volumes. In one embodiment, the vessels may be plastic or stainless steel enclosed vessels or medium-containing volumes. In one embodiment, the vessels may not be physically connected. In one embodiment, the vessels may be physically connected. In one embodiment, gas may be directed into one or more of the vessels simultaneously. In one embodiment, a reactor, reactor system, or system may comprise multiple vessels combined. In one embodiment, gas may be directed equally into each of vessels. In one embodiment, gas may be directed more into one vessel and less into another vessel. In one embodiment, gas may be directed first into one vessel, and then into another vessel. In one embodiment, gas may be exhausted from all vessels equally. In one embodiment, gas may be exhausted from all vessels individually, or more from one vessel and less from another vessel. In one embodiment, exhaust gas may be directed from one vessel into another vessel. In one embodiment, the liquid medium of the vessels is discrete and not mixed between the vessels. In one embodiment, the liquid medium of the vessels is not discrete and is mixed between the vessels. In one embodiment, gas is directed equally into all vessels, and liquid medium is mixed between the vessels. In one embodiment, gas is directed equally into all vessels, and liquid medium is at least partially mixed between the vessels. In one embodiment, gas is directed equally into all vessels, and liquid medium is at least partially mixed between the vessels. In one embodiment, gas is directed equally into all vessels, and liquid medium is not mixed between the vessels. In one embodiment, gas is directed first into one vessel and then into another vessel, and liquid medium is mixed between the vessels. In one embodiment, gas is directed first into one vessel and then into another vessel, and liquid medium is not mixed between the vessels. In one embodiment, exhaust gas from a first vessel is directed into a second vessel, and liquid medium is mixed between the vessels. In one embodiment, gas is directed individually and discretely into each vessel, and liquid medium is mixed between the vessels. In one embodiment, exhaust gas is directed individually and discretely into each vessel, and liquid medium is not mixed between the vessels. In one embodiment, the concentration of dissolved gas is caused to remain relatively elevated in one vessel and relatively depressed in another vessel. In one embodiment, the concentration of dissolved gas is caused to remain substantially equal in multiple vessels. In one embodiment, the gases are caused to be mixed equally throughout the vessels. In one embodiment, the gases are caused to move sequentially through the vessels. In one embodiment, the gases are caused to be injected individually into through the vessels. In one embodiment, the gases are caused to be injected individually and simultaneously into the vessels. In one embodiment, the gases are caused to move simultaneously through the vessels on an individual basis and medium is caused to not be fully mixed between the vessels, such that the medium remains substantially isolated. In one embodiment, the gases are caused to move sequentially through the vessels and medium is caused to not be fully mixed between the vessels. In one embodiment, the gases are caused to be injected individually and simultaneously into the vessels and medium is caused to be mixed between the vessels, such that the medium remains substantially non-isolated. In one embodiment, the gases are caused to move sequentially through the vessels to cause the medium in the vessels to be substantially non-isolated and gas is caused to move in multiple directions in each vessel. In one embodiment, the gases are caused to be injected simultaneously into the vessels, such that the gases are caused to move the medium in the vessels to be substantially non-isolated. In one embodiment, the gases are caused to be injected simultaneously into the vessels in such a manner that the gases are not caused to move the medium between the vessels. In one embodiment, gas may be moved between vessels by mechanical means, such as a pump. In one embodiment, liquid medium may be moved between vessels by mechanical means, such as a pump. In one embodiment, gas may be injected into a vessel by mechanical means. In one embodiment, liquid medium may be injected into a vessels by mechanical means, such as a pump. In one embodiment, gas and liquid medium may be injected simultaneously into a vessel by mechanical means, such as a pump, nozzle, venturi, compressor, diffusor, vacuum. In one embodiment, the vessels may be equipped with one or more internal cavitation mechanisms. In one embodiment, the vessels may be operated under recurring periods or patterns of pressure and vacuum to induce optimal mass transfer efficiency. In one embodiment, the vessels may be filled with one or more materials, that are more or less dense than liquid medium, that are able to dissolve or absorb high concentrations or amounts of gases, such as methane, oxygen, or carbon dioxide, wherein such materials may be silica-based gels or beads, activated carbon, nickel-plated spheres, polypropylene beads, PES beads, PTFE beads, or ultra high molecular weight polyethylene pellets. In one embodiment, the rapid pulsation of pressure in the vessels causes the absorbent materials to absorb gases at high concentration, and then release at least some of the gases into the medium, causing an increase in mass transfer into the liquid medium. In one embodiment, a vessel is filled with liquid medium containing gas-absorbent material, such as plastic beads, and the vessel is subject to recurring periods of pressurization, such that the vessel acts similar to an oxygen concentration system or other pressure swing absorption system, thereby increasing the solubility, mass transfer, and/or uptake of gases in the vessel by the microorganisms and liquid medium. In one embodiment, such pressure or depressurization cycle may comprise 1-100 minutes per cycle or stage, or 1-300 minutes per complete pressure-depressurization cycle. In one embodiment, the liquid medium and/or concentration of dissolved gases in the reactor is caused to remain relatively constant or homogenous with mixing induced by the action of the cavitation (e.g., cavitation induced by a moving blade or liquid moving over a surface), sonication (e.g., ultrasonication), sonic induction, gases (e.g., gas displacement), liquid displacement, mechanical pumping (e.g., rotary pump), the movement of entrained materials (e.g., the movement of liquid-entrained plastic balls), or other means while the concentration of gases is caused to be reduced on a proximal basis according to the cycle of pressure in the system (e.g., from vacuum pressure to superatmospheric pressure), proximity to an absorbent material (including the associated pressure cycle), sequential location of gas relative to gas flow path (e.g., location in gas vessels), and location or proximity to injection port relative to exhaust port (e.g., retention time of gas). In one embodiment, a reactor may be vertically configured, such that the height of the vessel exceeds the width of the vessel. In one embodiment, a reactor may be horizontally configured, such that the width of the vessel exceeds the height of the vessel.

In several embodiments, PHA synthesis is induced in a microorganism culture comprising methane-utilizing, heterotrophic, and/or carbon dioxide-utilizing microorganisms wherein a PHA inclusion concentration (by dry biomass weight) is generated of between about 0.01% and about 95%. In some embodiments, the inclusion concentration is between about 25% and about 80%, including about 25 to about 35%, about 35% to about 50%, about 50% to about 65%, about 65% to about 80%, and overlapping ranges thereof. In some embodiments, the inclusion concentration is between about 0.01% and about 55%, including, about 0.01% to about 1%, about 1% to about 5%, about 5% to about 10%, about 10% to about 15%, about 15% to about 20%, about 20%, to about 25%, about 25% to about 30%, about 30% to about 35%, about 35% to about 40%, about 40% to about 45%, about 45% to about 50%, about 50% to about 55%, and overlapping ranges thereof. In some embodiments, these inclusion ratios are achieved with reduced carbon input, reduced energy expenditure, or reduced numbers of microorganisms (thereby representing a more efficient generation of PHA). In some embodiments, PHA synthesis is induced in a methanotrophic, heterotrophic, and/or autotrophic microorganism culture wherein a PHA inclusion concentration (by dry biomass weight) is generated of between about 20% and about 80%, between about 30% and about 70%, between about 40% and about 60%, between about 50% and about 70%, including about 50% to about 55%, about 55 to about 60%, about 60% to about 65%, about 65% to about 70%, and overlapping ranges thereof. In some embodiments of the invention, PHA synthesis is induced in microorganism culture comprising methanotrophic, autotrophic, and heterotrophic microorganisms, wherein an average PHA inclusion concentration (by dry biomass weight) is greater than about 5%, greater than about 20%, greater than about 40%, greater than about 65%, or greater than about 70% by dry cell weight.

In some embodiments, the growth culture media is manipulated to induce both i) microorganism growth and ii) PHA synthesis within one or more open, non-sterile, or sterile vessels using a feast-famine culture regime. In some embodiments, the microorganisms are subject to successive alternating periods of nutrient/carbon availability and nutrient/carbon unavailability to encourage the reproductive success of microorganisms that are capable of synthesizing PHA, particularly at high inclusion concentrations. Feast-famine regimes useful for the selection of PHA producing microorganisms, including PHA-producing methanotrophic microorganisms, over microorganisms that either cannot produce PHA, produce PHA slowly, or produce PHA at relatively low concentrations are described in the art (Verlinden, et al., "Bacterial synthesis of biodegradable polyhydroxyalkanoates," Journal of Applied Microbiology, 102 (2007), p. 1437-1449, Frigon, et al., "rRNA and Poly-Hydroxybutyrate Dynamics in Bioreactors Subjected to Feast and Famine Cycles," Applied and Environmental Microbiology, April 2006, p. 2322-2330; Müller, et al., "Adaptive responses of *Ralstonia eutropha* to feast and famine conditions analysed by flow cytometry," J Biotechnol. 1999-10-8; 75(2-3):81-97; Reis, et al., "Production of polyhydroxyalkanoates by mixed microbial cultures," Bioprocess and Biosystems Engineering, Volume 25, Number 6, 377-385, DOI: 10.1007/s00449-003-0322-4.)

In some embodiments of the invention, the classical feast-famine regime is modified to reduce PHA losses. Specifically, in the past, feast-famine regimes were thought to be effective by passing a microorganism culture through a period wherein carbon or nutrients were unavailable or relatively limited for metabolism, thereby forcing the culture to accumulate and/or consume intracellular PHA as a source of carbon to survive, and thereby selecting for microorganisms with the capacity to synthesize and store PHA. Applicant has surprisingly discovered that, some microorganisms with higher concentrations of intracellular PHA reproduce more efficiently than microorganisms with lower concentrations of intracellular PHA in periods of carbon availability and nutrient balance. Thus, in one embodiment, a novel PHA production regime is employed in one or more vessel wherein microorganisms are subjected to two successive and recurring phases: 1) growth, wherein carbon and nutrient availability is optimized for reproduction, and 2) PHA synthesis, wherein carbon is available in excess, and one or more nutrient is reduced or increased relative to the growth period to induce PHA synthesis. In some embodiments, a fraction of the vessel media is removed for downstream PHA extraction and processing after the PHA synthesis period, and that fraction is replaced with lower cell density media, which simultaneously returns carbon and nutrient concentrations to reproductively favorable levels, e.g., the growth phase or growth conditions, and causes microorganisms to enter into a reproductive phase without consuming significant portions of intracellular PHA. As such, efficient PHA producing microorganisms selectively reproduce over inefficient or non-PHA producing microorganisms. As a result, some embodiments, i) increase the speed of the microorganism selection process by removing the PHA consumption step typical to previous feast famine models and ii) reduce the loss of PHA to cellular metabolism. According to such embodiments, the feast famine model is converted to a feast-polymerization-feast process. In several embodiments methanotrophic, autotrophic, and/or heterotrophic cultures are used in the feast-polymerization-feast process.

Removing a Portion of the PHA-Containing Biomass from the Culture, and Extracting PHA from the Removed PHA-Containing Biomass to Produce Isolated PHA and PHA-Reduced Biomass In several embodiments, following the production of a microorganism culture comprising biomass and PHA (discussed above), at least a portion of the PHA-containing biomass is removed from the culture. In several embodiments, a portion ranging from about 20% to about 80% of the PHA-containing biomass is removed, including about 30% to about 70%, about 40% to about 60%, about 45% to about 55%, and overlapping ranges thereof. Removal of PHA-containing biomass may be performed by a number of methods, including centrifugation, filtration, density separation, flocculation, agglomeration, spray drying, or other separation technique. In some embodiments, dewatering (e.g., by centrifugation) results in a biomass having a desirable water content that facilitates downstream processing of the biomass. For example, in some embodiments, centrifugation of the PHA-containing biomass reduces the amount of culture media (increases the relative biomass concentration) to a concentration range between about 100 and about 500 grams of biomass per liter of culture media. In some embodiments, the concentration is of the biomass is adjusted to about 100 to about 200 g/L, about 200 to about 300 g/L, about 300 to about 400 g/L, about 400 to about 500 g/L, and overlapping ranges thereof. Advantageously, such an approach also produces, as an effective by-product, clarified culture media that can be optionally treated, measured, or recycled into one or more culture vessels.

In some embodiments, after a portion of the PHA-containing biomass is removed from the culture, PHA is extracted from the removed PHA-containing biomass to produce isolated PHA and PHA-reduced biomass. In some embodiments, supercritical (SC) fluids, such as SC-CO$_2$ or SC-water are used to purify PHA, such that proteins and/or non-PHA materials are rendered at least partially solubilized in SC-CO$_2$, SC-water, high temperature or high pressure water, and/or mixtures thereof. In some embodiments, compatibilizing extraction agents may be used, such as non-PHA polymers that maintain miscibility with PHA and high solubility in SC-fluids, such that the PHA, miscible polymer, and SC-fluid produce a low viscosity solution capable of separating PHA from non-PHA material.

As used herein, the terms "extraction" and "PHA extraction" shall be given their ordinary meaning and shall be used interchangeably to describe the removal and/or separation of PHA from biomass. PHAs may be extracted from biomass by several processes, including, but not limited to, the use of chemicals (e.g., solvents) alone or in combination with mechanical means and/or enzymes. These processes include the use of: solvents, such as acetone, ethanol, methanol, methylene chloride, dichloroethane, with and/or without the application of pressure and/or elevated temperatures, supercritical carbon dioxide, enzymes, such as proteases, surfactants, pH adjustment, including the protonic or hydroxide-based dissolution of non-PHA biomass, and/or hypochlorite (or another solvent) to dissolve non-PHA biomass, including the use of hypochlorite in conjunction with another solvent, such as methylene chloride or with, carbon dioxide, enzymes, acids, bases, polymers, or surfactants, or combinations thereof. In some embodiments of the invention, PHA is extracted by solvent extraction from a PHA-containing biomass comprising gas-utilizing microorganisms and/or biomass-utilizing microorganisms to produce isolated PHA and PHA-reduced biomass. In some solvent-based embodiments, solvents suitable for dissolving the PHA are used, including carbon dioxide, acetone, methylene chloride, chloroform, water, ethanol, and methanol. In some embodiments, particular ratios of solvent to PHA provide optimal dissolution of PHA from the culture, and therefore lead to improved extraction and isolation efficiency and yield. For example, in some embodiments, ratios of solvent to PHA (in grams) of about 500:1 are used. In some embodiments, ratios of about 0.01:1 are used. In some embodiments, ratios ranging from between about 500:1 and about 0.01:1 are used, such as about 0.05:1, about 1.0:1, about 1.5:1, about 20:1, about 250:1, about 300:1, about 350:1, about 400:1, or about 450:1.

As discussed above, changes in temperature and/or pressure may also be used to facilitate the extraction of PHA from the PHA-containing biomass. In some embodiments, the extraction solvent chosen dictates the limits of temperature, pressure, and/or incubation times that are used. In some embodiments, solvent is combined with PHA-containing biomass and incubated for several minutes up to several hours. For example, in some embodiments, incubation is for about 10 minutes, while in other embodiments, overnight incubation times are used. In some embodiments, incubation times range from 30 minutes to about 1 hour, about 1 hour to about 2 hours, about 2 hours to about 4 hours, about 4 hours to about 6 hours, about 6 hours to about 8 hours, about 8 hours to about 10 hours, and from about 10 hours to overnight. Choice of incubation time is determined by solvent, culture density (e.g., number of microorganisms), type of organisms, expected PHA yield, and other similar factors.

Incubation temperature is also tailored to the characteristics of a given culture. Incubation temperatures can range from below room temperature to elevated temperatures of up to about 150° C. or about 200° C. For example, depending the solvent and other variables of the culture, temperatures are used that range from about 10° C. to 25° C., from about 25° C. to about 40° C., from about 40° C. to about 55° C., from about 55° C. to about 60° C., from about 60° C. to about 75° C., from about 75° C. to about 90° C., from about 90° C. to about 105° C., from about 105° C. to about 120° C., from about 120° C. to about 135° C., from about 135° C. to about 150° C., from about 150° C. to about 200° C., and overlapping ranges thereof.

As can be appreciated, if changes in temperature are made to a culture in a closed vessel, changes in pressure result. In some embodiments, increased pressure provides a shearing effect that aids in the liberation of PHA from the microorganisms. In some embodiments, pressure is regulated within a particular range. For example, in some embodiments, pressure of the reaction of the PHA-containing biomass with solvent occurs between about 40 and 30,000 psi, including about 50 to about 60 psi, about 60 to about 70 psi, about 70 to about 80 psi, about 80 to about 90 psi, about 90 to about 100 psi, about 100 to about 125 psi, about 125 to about 150 psi, about 150 to about 175 psi, about 175 to about 200 psi, about 200 to about 1000 psi, about 1000 to about 5000 psi, about 5000 psi to about 10,000 psi, about 10,000 to about 20,000 psi, about 20,000 to about 30,000 psi, and overlapping ranges thereof. Additional sources of shear (e.g., agitation, pumping, stirring etc.) are optionally used in some embodiments to enhance the extraction of PHA. Any one, or combination, of the PHA extraction methods described herein, or disclosed in the art, may be utilized as a method to carry out PHA extraction and remove PHA from the PHA-containing biomass.

In several embodiments, a solvent-based extraction system is utilized to carry out PHA extraction. In some embodiments, solvents are utilized to carry out PHA extraction at high temperatures, wherein PHA extraction occurs simultaneous with a temperature-enhanced breakdown or dissolution of PHA-containing biomass. In some embodiments, one or more solvent is utilized that is biodegradable and metabolically assimilable by the culture, such that PHA-reduced biomass comprising biomass and one or more biodegradable solvent may be contacted with the culture, and both the PHA-reduced biomass and the solvent may be utilized by the culture as a source of carbon. Non-limiting examples of such solvents include carbon dioxide, acetone, ethanol, methanol, and methylene chloride, among others.

In several embodiments a mixture of solvent and PHA comprises multiple phases, e.g. an aqueous phase and an organic phase. In some embodiments, solvent-based extraction comprises a more uniform mixture of solvent and PHA. In some embodiments, depending on the solvent the phases are separated prior to recovery of the PHA. In some embodiments, a non-PHA polymer is also used, alone or in conjunction with other processes, for separation, flocculation, or other processing. In some embodiments, centrifugation is employed to further distinguish and separate the phases of the mixture (e.g., separation of the solvent-PHA phase from the water-biomass phase). In some embodiments, heat is also employed to maintain the solubility of the PHA in a given solvent.

Depending on the embodiment, the solubility of PHA varies with the solvent used, and therefore the temperature (if adjusted) and the separation techniques are tailored to match the characteristics of a given solvent. Thus, in some embodiments employing centrifugation, for example, a low speed centrifugation is used to separate the solvent-PHA phase from the water-biomass phase. In other embodiments, depending on the solvent, higher speed centrifugation is used. In some embodiments, centrifugation is employed in stages, e.g., low speed centrifugation followed by high speed centrifugation. Any of a variety of centrifuges can be employed, depending on the solvent used, for example, basket centrifuges, swinging bucket centrifuges, fixed rotor centrifuges, disc-back centrifuges, supercentrifuges, or ultracentrifuges.

In some embodiments, adjustable discharge ports suitable for a particular centrifuge are used in order to control the rate and degree of separation of solvent-PHA phase from the water-biomass phase. In some embodiments, the concentration of water in the water-biomass phase is adjusted to allow for suitable flow of the mixture through the centrifuge (or within a centrifuge tube). For example, in some embodiments, flow is suitable for separating the phases when the concentration of biomass (relative to water) is between about 1 and 100 g/L. In some embodiments, the concentration is between about 10 to about 20 g/L, about 20 to about 30 g/L, about 30 to about 40 g/L, about 40 to about 50 g/L, about 50 to about 60 g/L, about 60 to about 70 g/L, about 70 to about 80 g/L, about 80 to about 90 g/L, about 90 to about 100 g/L, about 100 to about 200 g/L, about 200 to about 400 g/L, about 400 to about 600 g/L, and overlapping ranges thereof.

In still additional embodiments, increases in temperature not only facilitate the extraction of the PHA, they also facilitate the isolation of the PHA from the solvent (e.g. increased temperature increases solvent evaporation).

In some embodiments, an extraction process is carried out to remove PHA from a microorganism in such a manner that the microorganism is deactivated. In some embodiments, the deactivation is permanent, while in some embodiments the deactivation is temporary. Without being bound by theory, it is believed that PHA extraction techniques which do not permanently disable microorganisms enable the PHA-reduced biomass generated thereby to contribute to the metabolism of carbon sources after a PHA extraction process, including through intracellular and extracellular metabolism. In one embodiment, methods useful for the temporary disablement of microorganisms include solvent extraction, including solvent extraction carried out below about 100° C., and particularly at intracellular temperatures below about 100° C., including extraction temperatures of about 10° C. to about 30° C., about 30° C. to about 50° C., about 50° C. to about 60° C., about 60° C. to about 70° C., about 70° C. to about 80° C., about 80° C. to about 90° C., about 90° C. to about 100° C., and overlapping ranges thereof.

In several embodiments, the PHA concentration of PHA-containing biomass is reduced as a result of the PHA extraction process. In several embodiments, the PHA concentration of PHA-containing biomass is reduced by at least about 0.01% (by dry cell weight). In some embodiments, the PHA concentration is reduced by about 10% to about 50%, about 50% to about 70%, about 70% to about 75%, about 75% to about 80%, about 80% to about 85%, about 85%, to about 90%, about 90% to about 95%, about 95% to about 99.9%, and overlapping ranges thereof.

While a variety of methods are known to enable the extraction PHA from biomass, most methods can be categorized into one of two classes: a) solvent-based extraction, or b) NPCM (non-polymer cellular material) dissolution-based extraction. NPCM dissolution-based extraction methods utilize chemicals (such as hypochlorite, or bleach), enzymes (such as protease), heat (especially to reach temperatures above 100° C.), pH (acids and bases), and/or mechanical means (such as homogenization) to break down, oxidize, and/or emulsify non-PHA cellular material. In some cases, extraction methods from both categories can be combined, such as the simultaneous utilization of hypochlorite and methylene chloride.

NPCM dissolution-based extraction methods require continuous and non-recoverable chemical inputs, such as hypochlorite, peroxides, enzymes, and pH adjustors, and also generate significant waste disposal issues. Thus, while these methods are effective, the use of solvent-based extraction methods is generally preferred in the industry due to the capacity of solvents to be distilled and recovered for continuous re-utilization in a closed loop cycle. Unfortunately, despite its benefits, some solvent-based extraction methods are energy intensive processes that play a major role in the high cost of PHA production, often accounting for more than 50% of total production costs. Accordingly, there exists a significant need for a novel method to significant increase the energy efficiency of solvent-based extraction.

In several embodiments, a process for the extraction of polyhydroxyalkanoates from biomass using a solvent-based extraction method is provided, wherein the energy required to carry out the process is reduced relative to prior solvent-based extraction methods. Specifically, in one embodiment a high efficiency PHA extraction process is provided comprising providing a PHA-containing biomass comprising PHA and water, mixing the biomass with a solvent at a temperature sufficient to dissolve at least a portion of the PHA into the solvent and at a pressure sufficient to enable substantially all or part of the solvent to remain in liquid phase, thereby producing a PHA-lean biomass phase and a PHA-rich solvent phase comprising solvent, water, and PHA, separating the PHA-rich solvent phase from the PHA-lean biomass phase at a temperature and pressure sufficient to enable substantially all or part of the solvent to remain in the liquid phase and prevent substantially all or part of the PHA within the PHA-rich solvent phase from precipitating, reducing the pressure or increasing the temperature of the PHA-rich solvent phase to cause the solvent to vaporize and the PHA to precipitate or become a solid while maintaining the temperature and/or the pressure of the PHA-rich solvent phase to prevent all or part of the temperature-dependent precipitation of the PHA into water, and collecting the solid PHA material, including optionally separating the precipitated PHA from the solvent and/or the water.

In the past, PHA precipitation has been induced in PHA-rich solvent by a) adding a non-PHA solvent to the solvent phase to reduce the solubility of PHA in the solvent phase and/or b) reducing the temperature of the solvent phase to reduce the solubility of PHA in the solvent. In particular, some methods 1) dissolve PHA in a solvent by increasing the temperature of the solvent and 2) precipitate PHA by reducing the temperature (and, thus, solubility) of the solvent. Other methods require adding water to a solution of PHA-rich solvent comprising dissolved PHA, wherein the addition of water to the solution reduces the solubility of the PHA in the solvent and causes the PHA to precipitate into the solvent and/or water. (For example, U.S. Pat. Nos. 4,562,245; 4,968,611; 5,894,062; 4,101,533, all herein incorporated by reference.) In each of these cases, energy efficiency is compromised; specifically, by adding water or a non-PHA solvent to reduce the PHA solubility of a solvent, additional energy is required for downstream water/non-solvent removal, heating, and/or distillation. By reducing the temperature of the solvent to reduce the solubility of the solvent and induce PHA precipitation, heat energy is redundantly expended, as the solvent must be re-heated for distillation and recovery. Therefore, in several embodiments, rather than adding a non-solvent to a PHA-solvent or reducing the temperature of the PHA-solvent to effect PHA precipitation, pressure and/or an increase in temperature is used to induce the precipitation or solidification of the PHA without redundantly reducing the temperature of solvent. Thus, in such embodiments, there is a significant reduction in the energy required to heat and/or distill non-solvent and/or solvent in downstream PHA processing.

In one embodiment, the extraction process is substantially carried out at intracellular temperatures less than about 100° C. In other embodiments, temperatures for extraction range from about 10° C. to about 30° C., from about 30° C. to about 50° C., from about 50° C. to about 70° C., from about 70° C. to about 90° C., from about 90° C. to about 120° C., from about 100° C. to about 140° C., from about 20° C. to about 150° C., or from about 120° C. to about 180° C., or higher. In one embodiment, cells are reused for polymerization following the extraction process as viable cells. In one embodiment, PHA-containing biomass is treated to one or more chemical treatment steps to control, modify, or increase the concentration or functional characteristics (e.g., molecular weight, monomer composition, melt flow profile, purity, non-PHA residuals concentration, protein concentration, DNA concentration, antibody concentration, antioxidant concentration) of PHA in a PHA-containing material or biomass. In one embodiment, temperature is used to control, modify, reduce, or optimize the molecular weight, polydispersity, melt flow, and other characteristics of PHA. In one embodiment, temperature and/or time is used to control the molecular weight of PHA between the range of 5,000,000 and 10,000 Daltons. In one embodiment, a slurry comprising PHA-containing biomass and a culture media is subject to one or more water removal steps or water addition steps to increase the concentration of PHA in a PHA-containing biomass. In one embodiment, the water removal step is a dewatering step or combination of dewatering steps, such as centrifugation, filtration, spray drying, flash drying, and/or chemical dewatering (e.g., with acetone, ethanol, or methanol), wherein at least a portion of the water concentration relative to the concentration of PHA-containing biomass in the slurry is reduced. In one embodiment, a temperature and/or pressure control step is carried out under atmospheric (0 psi), sub-atmospheric (−100-0 psi), or above-atmospheric pressure (e.g., 0-30,000 psi) and at temperature conditions wherein the PHA-containing biomass, or the liquid in and/or around the PHA-containing biomass, is maintained, for at least a period of time, at a temperature ranging from about −30 to about 10 degrees Celsius, about 10 degrees Celsius to about 100 degrees Celsius, about 10 degrees Celsius to about 150 degrees Celsius, about 20 degrees Celsius to about 250 degrees Celsius, and/or about 100 to about 200 degrees Celsius. In one embodiment, the PHA-containing biomass is subject to a dewatering step before or after the temperature and/or pressure control step, wherein the dewatering step is centrifugation, filtration, and/or spray drying, to produce a fully or partially de-watered PHA-containing biomass or PHA-containing biomass slurry, wherein the water concentration of the dried slurry is less than about 99%, less than about 95%, less than about 80%, less than about 60%, less than about 40%, less than about 30%, less than about 20%, less than about 10%, less than about 5%, less than about 3%, less than about 2%, or less than about 1% water. In one embodiment, the PHA-containing biomass is subject to a temperature control step, wherein the liquid chemicals within and/or around the biomass, e.g., water, methylene chloride, carbon dioxide, and/or ammonia, is controlled and maintained at a temperature of at least −30, at least −10, at least −5, at least −4, at least −3, at least −2, at least −1, at least 0, at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300 degrees Celsius (or overlapping ranges of those temperatures), wherein the solubility, dispersitivity, or homogeneity of non-PHA material increases in the liquid in and/or around the biomass. In one embodiment, the PHA-biomass is not dried prior to such temperature control step. In one embodiment, the PHA-containing biomass is dried or de-watered prior to such temperature control step. In one embodiment, the PHA-containing biomass is filtered or centrifuged following the temperature control step. In one embodiment, the PHA-containing cell slurry is not dewatered, for example, by centrifugation or other drying mechanism, prior to the temperature control step. In one embodiment, a mechanism to impart shear onto or into the PHA-containing biomass is coupled with a temperature control step; such shear may be imparted in the form of one or more shear induction mechanisms, e.g., centrifugal pump, agitator, blender, high shear mixer, vortex mixer, etc. In one embodiment, the PHA-containing biomass is dewatered in one step and the treated PHA-containing biomass is further dewatered in one or more additional steps. In one embodiment, the PHA-containing biomass is dewatered, water and/or other chemicals are added and temperature and/or pressure is controlled, and the treated PHA-containing biomass is further dewatered and/or purified. In one embodiment, the water and/or chemicals within, around, and/or added to the PHA-containing biomass is temperature and/or pressure controlled, and the treated PHA-containing biomass is further purified in one or more purification steps. In one embodiment, the temperature control step process time is approximately 1 second, approximately 5 seconds, approximately 10 seconds, approximately 25 seconds, approximately 60 seconds, approximately 2 minutes, approximately 5 minutes, approximately 20 minutes, approximately 45 minutes, approximately 1 hour, approximately 2 hours, approximately 5 hours, approximately 6 hours, approximately 7 hours, approximately 12 hours, approximately 15 hours, approximately 24 hours, approximately 36 hours, approximately 48 hours, or overlapping ranges of those times. In one embodiment, inorganic materials may be used to effect PHA modification, purification, or extraction, including carbon dioxide and dinitrogen. In one embodiment, the PHA-containing slurry or biomass is treated with carbon dioxide under elevated temperatures and pressures, including supercritical ranges, to induce PHA extraction or functional modification of PHA. In one embodiment, organic solvents, including methylene chloride, acetone, chloroform, dichloroethane, ethanol, and/or methanol are used in conjunction with any of the above steps. In one embodiment, solvents or extraction materials may be used or recycled for biomass production, biogas production, and/or PHA synthesis.

In one embodiment, chemicals are added to a PHA-containing biomass to cause the crystallization of PHA. In one embodiment, methylene chloride, carbon dioxide, acetone, water, dichloroethane, or methanol may be added to a PHA-containing biomass in order to induce the crystallization of PHA in the PHA-containing biomass. In some embodiments, this step may be useful for the downstream processing of PHA, wherein crystallized PHA is less prone than amorphous to degradation, including molecular weight loss, when contacted with extraction chemicals, including solvents, enzymes, acids, bases, and bleach. In one embodiment, silicon, silica, derivatives thereof, and/or chemicals containing silicon may be added to the PHA-containing biomass in order to impact the metabolic status of the culture, and thereby control the functional characteristics of the PHA produced by the culture, including molecular weight, monomer composition, co-polymer structure, melt index, and polydispersity.

The removal of non-PHA materials from PHA often accounts for a significant fraction of PHA production costs. As a specific example, pigments often cause unwanted discoloration of PHA, and must be removed through costly processes, such as ozonation, peroxide washing, acetone washing, ethanol washing, solvent refluxing, hypochlorite digestion, enzymatic degradation, surfactant dissolution, or other methods disclosed in the art. In several embodiments, a non-sterile process is used to select for microorganisms exhibiting minimal pigmentation. Applicant has surprisingly discovered that, by manipulating the concentration of dissolved oxygen in a microorganism system, a culture may be selected wherein white, tan, off-white, light brown, and/or light yellow pigments are exhibited rather than purple, red, pink, dark brown, orange, or other heavy pigments. Specifically, in some embodiments, an excess of dissolved oxygen is introduced into a growth media over successive periods, resulting in selective growth of strains of methanotrophic microorganisms which produce white, tan, off-white, light brown, and light yellow pigments, rather than those producing pink, red, purple, dark yellow, dark brown, and/or other heavy pigments. As a result, such embodiments, reduce the need for costly downstream pigmentation removal.

As used herein, the term "PHA-reduced biomass" or "substantially PHA-reduced biomass" shall be given its ordinary meaning and shall be used to describe a biomass material wherein the concentration of PHA relative to non-PHA material has been reduced in a PHA-containing biomass through the utilization of a PHA extraction process. In some embodiments, PHA-reduced biomass is further treated in a variety of ways. In some embodiments, the further treatment includes, but is not limited to, one or more of dewatering, chemical treatment, sonication, additional PHA extraction, homogenization, heat treatment, pH treatment, hypochlorite treatment, microwave treatment, microbiological treatment, including both aerobic and anaerobic digestion, solvent treatment, water washing, solvent washing, and/or drying, including simple or fractional distillation, spray drying, freeze drying, rotary drying, and/or oven drying.

In one embodiment, PHA-reduced biomass is substantially dried, wherein the resulting dried material comprises less than about 99% liquids, including water, solvents, salts, and/or growth-culture media. In some embodiments, the drying processes disclosed herein yield a dried material containing between about 95% and about 75% liquids, between about 75% and about 50% liquids, between about 50% and about 25% liquids, between about 25% and about 15% liquids. between about 15% and about 10% liquids, between about 10% and about 1% liquids, and overlapping ranges thereof. In some embodiments, drying is complete (e.g., between about 1% and 0.1% liquids, or less). In another embodiment of the invention, a liquid phase comprising PHA-reduced biomass is subjected to filtration, centrifugation, density differentiation, or other method to increase the solids content of the PHA-reduced biomass.

Traditionally, the separation of biomass from liquid growth media is difficult and impractical due to the plugging and fouling characteristics of biomass. In several embodiments, a method enabling the efficient filtration of microorganisms is provided. In some embodiments, a liquid chemical is added to the growth media comprising microorganisms, wherein the liquid chemical is ethanol, acetone, methanol, methylene chloride, ketones, alcohols, and/or chlorinated solvents, or a combination thereof. In some embodiments, microorganisms are then efficiently separated from liquid growth media using standard filtration equipment, such as a Buchner filter, filter press, or similar apparatus. In one embodiment, approximately 2 parts acetone are mixed with one part water, including both intracellular and extracellular water, to effect the efficient filtration of microorganisms comprising the water.

As used herein, the terms "isolated PHA" and "substantially isolated PHA" shall be given their ordinary meaning and shall refer to PHA that has been removed from a biomass material as a result of an extraction process, or a biomass material wherein the concentration of PHA relative to non-PHA material has been increased by an extraction process. In several embodiments, isolated PHA is further treated in one or more of a variety of ways, including, but not limited to, purification, filtration, washing, oxidation, odor removal, pigment removal, lipid removal, non-PHA material removal, and/or drying, including centrifugation, filtration, spray drying, freeze drying, simple or fractional distillation, or density differentiation. Methods for the purification of PHA include the use of peroxides, water, hypochlorite, solvents, ketones, alcohols, and various other agents to separate and remove non-PHA material from PHA material. In some embodiments, PHA is removed from a microorganism culture by solvent extraction to produce isolated PHA in a PHA-rich solvent phase and PHA-reduced biomass in a PHA-lean liquid phase. In some embodiments, the solvent phase is separated from the liquid phase by filtration or centrifugation. In some embodiments, both centrifugation and filtration are used in combination (e.g., sequentially). In some embodiments, centrifugation is optionally followed by filtration. In other embodiments, filtration is optionally followed by centrifugation. Filtration, in some embodiments is performed under vacuum pressure, via gravity feed, under positive pressure, or in specialized filtration centrifuges. In some embodiments, the filter pore size is adjusted based on the species composition of the microorganism culture. In some embodiments, pore sizes of up to 200 µm are used. In some embodiments, smaller pore sizes are used, for example 15 to 20 µm, 10 to 15 µm, 5 to 10 µm, 1 to 5 µm, 0.001 to 1 µm, and overlapping ranges thereof.

In addition to the steps outlined above, additional steps may be taken to remove solvent from the extracted PHA, including evaporation, solvent casting, steam stripping, heat treatment, and vacuum treatment, each of which may be preferential, cost-effective, time-effective, or advantageous depending on the volatility and type of solvent used. In other embodiments, active processes can be used to reduce the solvent content of the solvent-PHA mixture. For example, in certain embodiments, alterations in temperature of certain solvents change the solubility of the PHA in the solvent, which effectively removes solvent from the PHA (e.g., the solvent is now separable from a precipitated PHA). In some embodiments, filtration, solvent temperatures, or vacuum treatment can be increased to reduce a portion of the solvent. In some embodiments, solvent to PHA ratios post extraction, filtration, evaporation, solvent casting, steam stripping, heat treatment, and/or vacuum treatment range from about 0.1:1 to about 1,000:1, including about 0.2:1, about 0.3:1, about 4.0:1, about 5.0:1, about 10.0:1, about 20.0:1, about 60:1, about 70:1, about 80:1, about 90:1, about 100:1, about 200:1, about 500:1, and about 900:1.

As a result of the processes disclosed above, in some embodiments, the solvent is substantially removed from the isolated PHA in the PHA-rich solvent phase and the liquid is substantially removed from the PHA-reduced biomass in the PHA-lean liquid phase. In some embodiments, the isolated PHA is dried in a heated vessel to produce substantially pure isolated PHA (e.g., at least 80% PHA by dry weight, preferably at least 98% PHA by weight, more preferably at least 99% PHA by weight).

Numerous varieties of heated or drying vessels may be used to dry the isolated PHA, including ovens, centrifugal dryers, air dryers, spray dryers, and freeze dryers, among others. In some embodiments, heat is applied to a drying vessel to speed the process and/or to remove (e.g., evaporate traces of solvent from the PHA). The moisture content of the isolated PHA will depend, in some embodiments, on the solvent used, and the corresponding separation technique used (as described above). For example, a volatile solvent in combination with ultracentrifugation would result in a less moist extracted PHA, while a less active separation technique (e.g., gravity phase separation) would yield a more moist extracted PHA. In some embodiments, internal dryer temperatures range from 20° C. to 40° C. to about 200° C. In some embodiments, internal temperatures range from about 50° C. to about 90° C., about 90° C. to about 180° C., about 65° C. to about 175° C. and overlapping ranges thereof. In some embodiments, outlet temperatures are substantially lower than inlet on internal temperatures. In some embodiments, outlet temperatures range from 30° C. to 90° C. In some embodiments, outlet temperatures are between about 35° C. to 40° C., about 40° C. to about 45° C., about 45° C. to about 50° C., about 50° C. to about 55° C., about 55° C. to about 90° C., and overlapping ranges thereof. It shall also be appreciated that the internal and outlet temperatures may be adjusted throughout the drying process (e.g., the temperature difference may initially be large, but decrease over time, or vice versa).

Depending on the embodiment, the type of dryer used, and the temperatures used (if other than atmospheric temperatures) are easily tailored to correspond to the techniques used in the extraction process. In some embodiments, particular dryer components are beneficial in the isolation of PHA. For example, depending on the moisture content of the extracted PHA (e.g., the amount of residual solvent) particular components of an evaporative-type dryer, such as an oven dryer, rotary dryer, spin flash dryer, conveyor dryer, spray dryer (equipped with various types of nozzle types, including rotary atomizer, single flow atomizer, mist atomizer, pressure atomizer, dual-flow atomizer) convection heat dryer, tray dryer, scrape-flash dryer, or other dryer type are used. By way of additional example, if a freeze dryer (e.g., a lyophilizer) is used, in some embodiments a manifold dryer is used, optionally in conjunction with a heat source. Also by way of example, a tray lyophilizer can be used, in some embodiments, with the isolated and dried PHA being stored and sealed in containers (e.g., vials) before re-exposure to the atmosphere. In certain embodiments, such an approach is used when long-term storage of the PHA is desired.

It shall also be appreciated that certain varieties of heated/drying apparatuses have adjustable flow rates that can be tailored to the moisture content of the isolated PHA. For example, an isolated PHA having a high moisture content would be fed into a dryer at a slower input rate to allow a higher degree of drying per unit of PHA inputted into the dryer. Conversely, a low moisture content isolated PHA would likely require less time to dry, and therefore could be input at a faster rate. In some embodiments, input rates of isolated PHA range from several hundred liters of isolated PHA-solvent mixture per minute down to several milliliters per minute. For example, input rates can range from about 10 mL/min to about 6 L/min, including about 10 ml/min to about 50 ml/min, about 50 mL/min to about 100 ml/min, about 100 ml/min to about 500 ml/min, about 500 ml/min to about 1 L/min, about 1 L/min to about 2 L/min, about 2 L/min to about 4 L/min, about 4 L/min to about 6 L/min, and about 100 L/min to about 500 L/min.

A range of PHA functional characteristics can be attained by mixing one PHA molecule, such as PHB, with various PHA polymers, including PHB, at various molecular weights. Therefore, in several embodiments, a first isolated PHA is heated to reduce the molecular weight of the first isolated PHA, and then subsequently mixed with a second PHA wherein the molecular weight of the second PHA is higher than the molecular weight of the first PHA. With such embodiments, Applicant has surprisingly discovered methods to functionalize one or more PHAs, including PHB. In additional embodiments of the invention, the molecular weight of a first PHA is reduced from about 800,000 to about 5,000,000 Daltons to about 30,000 to about 800,000 Daltons and mixed with a second PHA with a molecular weight of about 800,000 to about 5,000,000 Daltons to modify the functionalities of the input PHAs. In yet another embodiment, a first PHA is mixed with a second PHA wherein the molecular weight of the first PHA is at least 0.1% less than the molecular weight of the second PHA. In some embodiments, the difference in molecular weight between the first and second PHA is about 0.1% to about 1%, about 1% to about 10%, about 10% to about 20%, about 20% to about 30%, about 30% to about 40%, about 40% to about 50%, about 50% to about 60%, about 60% to about 70%, and overlapping ranges thereof. In still additional embodiments, PHAs having greater differences in molecular weight are used. In yet another embodiment, the molecular weight of a first PHB is reduced to less than about 100,000-500,000 Daltons and mixed with a second PHA with a molecular weight greater than about 100,000-500,000 Daltons to modify the functionality of the input PHB. Input PHA and PHB weight may vary from the ranges disclosed above, but based on the differences in the molecular weights, the alteration in functionality of the input PHB is still achieved.

In several embodiments, the molecular weight is adjusted in order to tune, alter, or otherwise modify one or more characteristics of the end-product PHA produced. For example, in several embodiments, reduction of the molecular weight of the PHA, in turn, reduces the crystallinity of the PHA. In several embodiments, the molecular weight of a PHA is reduced, such that i) the crystallinity of the PHA is also reduced and/or ii) the onset or rate of crystallization is caused to slow. In several embodiments, this is advantageous because the reduced crystallinity allows use of the PHA in products with reduced brittleness (e.g., increased flexibility and/or durability). In several embodiments, the reduced rate of crystallization increases the ease of manufacturing and reduces associated costs with maintaining PHA in a non-crystallized state. In several embodiments the rate of crystallization is adjusted (via molecular weight variation) such that crystallization occurs within a period of time ranging from about 1 second to about 60 seconds, about 10 seconds to about 2 minutes, about 3 minutes to about 10 minutes, about 1 minute to about 60 minutes, about 10 minutes to 3 hours, about 1 hour to about 12 hours, about 6 hours to about 24 hours, about 18 hours to about 3 days, about 1 day to about 10 days, about 3 days to about 30 days, about 10 days to about 90 days, about 90 days to about 180 days, or more than 365 days (and overlapping time ranges therebetween).

In one embodiment, the molecular weight of a PHA is reduced by about 10%, about 20%, about 50%, about 75%, or about 99%. In several embodiments, the starting molecular weight is in a range from about 100,000 to about 3,000,000 daltons. In several embodiments, post-reduction, the molecular weight ranges from about 50 to about 200,000 daltons, from about 50 to about 50,000 daltons, from about 50 to about 120,000 daltons, from about 50 to about 140,000 daltons, from about 50 to about 160,000 daltons, from about 50 to about 180,000 daltons, from about 500 to about 200,000 daltons, from about 1000 to about 200,000 daltons, from about 5000 to about 200,000 daltons, from about 10,000 to about 200,000 daltons, from about 20,000 to about 200,000 daltons, from about 50,000 to about 200,000 daltons, and overlapping ranges thereof. In one embodiment, the molecular weight of a PHA is reduced from an initial range of about 250,000 to about 1,800,000 daltons to a range of about 20,000 to about 150,000 daltons.

In several embodiments, upon heating such reduced-MW PHA to its melting point or above its melting point, and subsequently cooling the reduce-MW PHA to below its melting point, the crystallinity of the resultant PHA is reduced relative to the crystallinity of non-reduced molecular weight PHA subjected to the same conditions. In several embodiments, the reduction in crystallinity of the reduced-MW PHA is by over about 10%, about 15%, about 25%, about 50%, about 75%, or about 90% relative to the crystallinity of non-reduced MW PHA. In several embodiments, such crystallinity PHAs having reduced crystallinity may optionally include one or more of PHB, PHBV, PHHX, PHV, PHO, and/or a range of other PHAs.

In one embodiment, the invention comprises a PHA comprising carbon derived from PHA-reduced biomass, wherein the PHA-reduced biomass comprises carbon derived from one or more carbon-containing gas and/or one or more source of source of carbon. In one embodiment, PHA is co-mingled and/or melted with biomass, including, as examples, methanotrophic, autotrophic, heterotrophic biomass, and/or PHA-reduced biomass, to improve the functional characteristics of the PHA. In one embodiment, PHA is co-mixed and/or melted with biomass, including, as examples, methanotrophic, autotrophic, heterotrophic biomass, and/or PHA-reduced biomass, to improve the functional characteristics of PHA. In one embodiment, the percentage of non-PHA microorganism biomass included in a PHA, PHA compound, or PHA mixture is about 0.00001% to about 0.001%, about 0.001% to about 0.01%, about 0.01% to about 0.1%, to about 0.1% to about 0.5%, about 0.5% to about 1%, about 1%, to about 2%, about 2% to about 3%, about 3% to about 5%, about 5% to about 7%, about 7% to about 10%, about 10% to about 15%, about 15% to about 20%, about 20% to about 30%, about 30% to about 40%, about 40% to about 50%, about 50% to about 60%, about 60% to about 70%, about 70% to about 80%, about 80% to about 90%, about 90% to about 98%, about 98% to about 99.99%, and overlapping ranges thereof. In some embodiments, the inclusion of microorganism biomass to a PHA improves the functional characteristics of a PHA by acting as one or more of the following: nucleating agent, plasticizer, compatibilizer, melt flow modifier, mold release agent, filler, strength modifier, elasticity modifier, or density modifier. In some embodiments, microscopic size, molecular weight, molecular weight dispersity, and/or chemical nature of microorganism biomass and/or modified, including modified or non-modified nucleic acids and proteins, including biomass that has been subject to a modification step, is particularly and surprisingly effective as a functionalization agent for PHA. In some embodiments, biomass or modified biomass acts as a surprisingly effective compatibilizer and functional modifier for PHA and for PHA and non-PHA polymers, such as polypropylene and polyethylene. In one embodiment, biomass and/or modified biomass is mixed with a PHA material, including PHA and/or other non-PHA polymers, to modify the nucleation, plasticization, compatibilization, melt flow, density, strength, elongation, elasticity, mold strength, mold release, and/or bulk density characteristics of a PHA material, which may be melted, extruded, film blown, die cast, pressed, injection molded, or otherwise processed. In one embodiment, PHA is partially or not removed from PHA-containing microorganism biomass prior to melt processing, e.g., extrusion, injection molding, etc. In one embodiment, non-PHA biomass parts or materials are caused to remain with PHA derived from a PHA-containing biomass in order to modify or control the functional characteristics of a PHA material. In one embodiment, PHA is present in PHA-containing biomass at a concentration ranging from 1-99.99999%, 1-99.99%, 1-99%, 5-99%, 10-99%, 20-99%, 30-99%, 50-99%, 70-99%, 80-99%, 90-99%, 95-99%, or 98-99%, and overlapping ranges thereof. In one embodiment, PHA, biomass, and one or more non-PHA material, polymer, or thermoplastic are mixed, melted, or processed together. In one embodiment, the non-PHA polymer consists of one or more of the following: polypropylene, polyethylene, polystyrene, polycarbonate, acrylonitrile butadiene styrene, polyethylene terephthalate, polyvinyl chloride, fluoropolymers, liquid crystal polymers, acrylic, polyamide/imide, polyarylate, acetal, polyetherimide, polyetherketone, nylon, polyphenylene sulfide, polysulfone, cellulosics, polyester, polyurethane, polyphenylene oxide, polyphenylene ether, styrene acrylonitrile, styrene maleic anhydride, thermoplastic elastomer, ultra high molecular weight polyethylene, epoxy, melamine molding compound, phenolic, unsaturated polyester, polyurethane isocyanates, urea molding compound, vinyl ester, polyetheretherketone, polyoxymethylene plastic, polyphenylene sulfide, polyetherketone, polysulphone, polybutylene terephthalate, polyacrylic acid, cross-linked polyethylene, polyimide, ethylene vinyl acetate, styrene maleic anhydride, styrene-acrylonitrile, poly(methyl methacrylate), polytetrafluoroethylene, polybutylene, polylactic acid, polyvinylidene chloride polyvinyl chloride, polyvinyl acetate, polyvinyl acetate co-polyvinylpyrrolidone, polyvinylpyrrolidone, polyvinyl alcohol, cellulose, lignin, cellulose acetate butyrate, polypropylene, polypropylene carbonate, propylene carbonate, polyethylene, ethyl alcohol, ethylene glycol, ethylene carbonate, glycerol, polyethylene glycol, pentaerythritol, polyadipate, dioctyl adipate, triacetyl glycerol, triacetyl glycerol-co-polyadipate, tributyrin, triacetin, chitosan, polyglycidyl methacrylate, polyglycidyl methacrylate, oxypropylated glycerine, polyethylene oxide, lauric acid, trilaurin, citrate esters, triethyl citrate, tributyl citrate, acetyl tri-n-hexyl citrate, saccharin, boron nitride, thymine, melamine, ammonium chloride, talc, lanthanum oxide, terbium oxide, cyclodextrin, organophosphorus compounds, sorbitol, sorbitol acetal, sodium benzoate, clay, calcium carbonate, sodium chloride, titanium dioxide, metal phosphate, glycerol monostearate, glycerol tristearate, 1,2-hydroxystearate, cellulose acetate propionate, polyepichlorohydrin, polyvinylphenol, polymethyl methacrylate, polyvinylidene fluoride, polymethyl acrylate, polyepichlorohydrin-co-ethylene oxide, polyvinyl idene chloride-co-acrylonitrile, polycyclohexyl methacrylate, cellulose acetate butyrate, cellulose, starch, cellulose acetate butyrate-g-polyethyelene glycol, polyvinylidene chloride co-acrylonitrile, polyvinyl acetate, polyethylene glycol b-poly(e-caprolactone), R-PHB-OH, S-PHB-OH, polyphenol poly(4,4'-dihydroxydiphenyl ester, 4-tert-butylphenol, polyglutamate, acrylonitrile-butadiene-styrene, polystyrene, styrene acrylonitrile, polyethylene 2,6-napthalate, polypropylene oxide, polyethylene terepthalate, polybutylacrylate, poly-y-benzyl-1-glutamate, starch-b-PPG-urethane, ethylene propylene rubber-g-sodium acrylate EPR-g-SA, polypropylene carbonate, polypropylene carbonate-co-polyvinyl acetate, natural starch, starch adipate, starch-b-polyester-urethane, starch-b-PEG-urethane, PHBV, polycaprolactone, PLLA, polyoxymethylene, polyvinyl acetate-co-vinyl alcohol, ethylene-propylene rubber, ethylene-vinyl-acetate copolymer, synthetic poly3-hydroxybutyrate, poly-3-hydroxybutyrate-co-poly-3-hydroxyvalerate, poly-3-hydroxypropionate, polybutylene succinate-co-butylene adipate, polybutylene succinate-co-caprolactone, phenol poly(4,4'-dihydroxydiphenyl ester, and/or other similar materials. In one embodiment, PHA, methanotrophic, autotrophic, and/or heterotrophic microorganism biomass, and a non-PHA polymer are mixed and melted together. In one embodiment, the concentration of non-PHA microorganism biomass in such a mixture ranges from 0.0001% to 90%, 0.1% to 30%, 0.1% to 10%, or 0.5% to 8%, and overlapping ranges thereof. In one embodiment, the functional characteristics of a polyhydroxyalkanoate (PHA) material are augmented, controlled, or optimized, comprising the steps of: (a) providing a PHA and a microorganism biomass, (b) combining the PHA and the biomass in a mixture to form a compound, (c) heating the compound to between 40 degrees Celsius and 250 degrees Celsius. In one embodiment, the biomass is present in said mixture at a concentration of about 0.1 to about 20%. In one embodiment, the biomass is present in said mixture at a concentration of about 0.1 to about 80%. In one embodiment, the biomass is present in said mixture at a concentration of about 0.1 to about 8%. In one embodiment, the biomass is methanotrophic biomass. In one embodiment, the biomass is autotrophic biomass. In one embodiment, the biomass is heterotrophic biomass. In one embodiment, the biomass is present in said mixture at a concentration of about 0.1 to about 20%. In one embodiment, the functional characteristics of a polyhydroxyalkanoate (PHA) material are optimized, controlled, or augmented, comprising the steps of: (a) providing a PHA, a microorganism biomass, and a non-PHA polymer, (b) combining the PHA, the non-PHA polymer, and the biomass in a mixture to form a compound, and (c) heating the compound to between 40 degrees Celsius and 250 degrees Celsius. In one embodiment, the biomass is present in said mixture at a concentration of between about 0.1 to about 20%. In one embodiment, the biomass is present in said mixture at a concentration of between about 0.1 to about 80%. In one embodiment, the biomass is present in said mixture at a concentration of between about 0.1 to about 8%. In one embodiment, the biomass is methanotrophic biomass. In one embodiment, the biomass is autotrophic biomass. In one embodiment, the biomass is heterotrophic biomass. In one embodiment, the biomass is present in said mixture at a concentration of between about 0.1 to about 20%. In one embodiment, the biomass is present in said mixture at a concentration of between about 0.1 to about 20%. In one embodiment, the biomass is present in said mixture at a concentration of between about 0.1 to about 80%. In one embodiment, the biomass is present in said mixture at a concentration of between about 0.1 to about 8%. In one embodiment, the biomass is methanotrophic biomass. In one embodiment, the biomass is autotrophic biomass. In one embodiment, the biomass is heterotrophic biomass. In one embodiment, the non-PHA polymer is one or more of the following: polypropylene, polyethylene, polystyrene, polycarbonate, acrylonitrile butadiene styrene, polyethylene terephthalate, polyvinyl chloride, fluoropolymers, liquid crystal polymers, acrylic, polyamide/imide, polyarylate, acetal, polyetherimide, polyetherketone, nylon, polyphenylene sulfide, polysulfone, cellulosics, polyester, polyurethane, polyphenylene oxide, polyphenylene ether, styrene acrylonitrile, styrene maleic anhydride, thermoplastic elastomer, ultra high molecular weight polyethylene, epoxy, melamine molding compound, phenolic, unsaturated polyester, polyurethane isocyanates, urea molding compound, vinyl ester, polyetheretherketone, polyoxymethylene plastic, polyphenylene sulfide, polyetherketone, polysulphone, polybutylene terephthalate, polyacrylic acid, cross-linked polyethylene, polyimide, ethylene vinyl acetate, styrene maleic anhydride, styrene-acrylonitrile, poly(methyl methacrylate), polytetrafluoroethylene, polybutylene, polylactic acid, and/or polyvinylidene chloride, polyvinyl chloride, polyvinyl acetate, polyvinyl acetate co-polyvinylpyrrolidone, polyvinylpyrrolidone, polyvinyl alcohol, cellulose, lignin, cellulose acetate butyrate, polypropylene, polypropylene carbonate, propylene carbonate, polyethylene, ethyl alcohol, ethylene glycol, ethylene carbonate, glycerol, polyethylene glycol, pentaerythritol, polyadipate, dioctyl adipate, triacetyl glycerol, triacetyl glycerol-co-polyadipate, tributyrin, triacetin, chitosan, polyglycidyl methacrylate, polyglycidyl methacrylate, oxypropylated glycerine, polyethylene oxide, lauric acid, trilaurin, citrate esters, triethyl citrate, tributyl citrate, acetyl tri-n-hexyl citrate, saccharin, boron nitride, thymine, melamine, ammonium chloride, talc, lanthanum oxide, terbium oxide, cyclodextrin, organophosphorus compounds, sorbitol, sorbitol acetal, sodium benzoate, clay, calcium carbonate, sodium chloride, titanium dioxide, metal phosphate, glycerol monostearate, glycerol tristearate, 1,2-hydroxystearate, cellulose acetate propionate, polyepichlorohydrin, polyvinylphenol, polymethyl methacrylate, polyvinylidene fluoride, polymethyl acrylate, polyepichlorohydrin-co-ethylene oxide, polyvinyl idene chloride-co-acrylonitrile, polycyclohexyl methacrylate, cellulose acetate butyrate, cellulose, starch, cellulose acetate butyrate-g-polyethyelene glycol, polyvinylidene chloride co-acrylonitrile, polyvinyl acetate, polyethylene glycol b-poly(e-caprolactone), R-PHB-OH, S-PHB-OH, polyphenol poly(4,4'-dihydroxydiphenyl ester, 4-tert-butylphenol, polyglutamate, acrylonitrile-butadiene-styrene, polystyrene, styrene acrylonitrile, polyethylene 2,6-napthalate, polypropylene oxide, polyethylene terepthalate, polybutylacrylate, poly-y-benzyl-1-glutamate, starch-b-PPG-urethane, ethylene propylene rubber-g-sodium acrylate EPR-g-SA, polypropylene carbonate, polypropylene carbonate-co-polyvinyl acetate, natural starch, starch adipate, starch-b-polyester-urethane, starch-b-PEG-urethane, PHBV, polycaprolactone, PLLA, polyoxymethylene, polyvinyl acetate-co-vinyl alcohol, ethylene-propylene rubber, ethylene-vinyl-acetate copolymer, synthetic poly3-hydroxybutyrate, poly-3-hydroxybutyrate-co-poly-3-hydroxyvalerate, poly-3-hydroxypropionate, polybutylene succinate-co-butylene adipate, polybutylene succinate-co-caprolactone, and/or phenol poly (4,4'-dihydroxydiphenyl ester.

Purifying the Isolated PHA

In some embodiments, isolated PHA is purified to produce a PHA material that is substantially pure PHA. In some embodiments, the isolated PHA is purified to at least 20% pure PHA by dry weight. In some embodiments, the isolated PHA is purified to at least 55% pure PHA by dry weight, while in some embodiments, the isolated PHA is purified to at least 90% pure PHA by dry weight. In additional embodiments, purity of the isolated PHA is between about 90 and 99.9%, including about 91, about 92, about 93, about 94, about 95, about 96, about 97, about 98, and about 99% pure.

In several embodiments, isolated PHA may be recovered by any one, or a combination, of the methods described above, including, but not limited to: washing, filtration, centrifugation, dewatering, purification, oxidation, non-PHA material removal, solvent removal, and/or drying. In some embodiments, isolated PHA is recovered according to the manner in which it has been removed from the culture. For example, in embodiments in which solvent-based extraction is employed, a recovery method may be employed to remove the isolated PHA from the solvent and/or other non-PHA material. In one embodiment, solvent may be used to extract the PHA, wherein the solvent is then substantially removed from the isolated PHA by carrying out PHA precipitation and filtration, excess solvent distillation and/or removal, and/or drying, resulting in the recovery of dry, isolated PHA. In embodiments employing enzyme, surfactant, protonic, hydroxide, and hypochlorite-based extraction techniques wherein the dissolution of non-PHA material is induced, isolated PHA may be filtered, washed, separated, centrifuged, and/or dried, resulting in the recovery of dry, isolated, purified PHA. The resultant PHA, in some embodiments, is further used in downstream processing, including thermoforming. In one embodiment, the concentration of PHA is caused to go high enough (e.g., above about 70%, about 80%, or about 90%) to induce cell fragility and surprisingly cause PHA to be excreted or otherwise liberated extracellularly, through either no cell wall treatment or minimal cell wall treatment (such as, e.g., shear (induced by a liquid pump or agitator), heat (included by water wherein the temperature exceeds 10 degrees Celsius), or pH adjustment (low pH and/or high pH). In one embodiment, a method of causing the cell to become fragile and excrete or enable the extracellular liberation or simple purification of a PHA-biomass material by inducing a very high concentration of PHA is employed to enable an avoidance of the usage of toxic substances in purification or other processing steps, such as chlorine or chlorinated materials (such as chlorinated solvents, sodium hypochlorite, chlorine gas, or other toxic chemicals. In one embodiment, Applicants have surprisingly discovered that by inducing a suppression of an overproduction control switch or otherwise causing methanotrophic microorganisms, autotrophic microorganisms, and/or heterotrophic microorganisms to produce PHA at high concentrations (e.g., above about 60%, above about 70%, above about 80%, and/or above about 90%), it is possible to avoid the use of chlorine in purification or processing steps—e.g., wherein the only chemicals and/or conditions required to produce purified comprise: 1) water, 2) water and pressure, 3) water and carbon dioxide, 4) water and shear, 5) water and heat, 6) heat, 7) shear, 8) liquid-solid separation, 9) solid-solid separation, 10) liquid-liquid separation, 11) spray drying, 12) sonication, 13) flocculation, 14) ultrasonic treatment, 15) lyophilization, 16) water and hydrogen ions, 17) EDTA, 18) water and hydroxide ions, 19) sub or super critical carbon dioxide, 20) sub or super critical water, and/or 21) a combination of these chemicals and/or conditions. In one embodiment, PHA is separated from biomass or other non-PHA materials, including whole-cell microorganisms, enzymes, cell-surface attached enzymes, isolated enzymes, and/or a combination thereof, and non-PHA materials are recycled for use as a catalyst, nutrient, carbon source, nitrogen source, nutrient source, mineral source, whole-cell catalyst, isolated enzyme, or other material for further polymerization, cell growth, or chemical synthesis. In one embodiment, water is removed from or reduced in the PHA solution by using a batch, semi-batch, semi-continuous, and/or continuous water removal system, such as a spray dryer (including co-current, counter-current, pressure nozzle, rotary disc, or otherwise), extruder (including single screw or twin screw), lyophilizer, filter (including filter press, pressurized filter, rotary filter, screw filter, anionic, cationic, and/or other material-coagulating or polymer-assisted filter), flocculator, dissolved air flotation mechanism, and/or a combination of each of these water reducing mechanisms.

Returning PHA-Reduced Biomass to the PHA-Producing Culture to Convert PHA-Reduced Biomass into PHA In several embodiments of the invention, the PHA-reduced biomass is returned to the culture to cause the biomass-utilizing microorganisms within the culture to convert the carbon within the PHA-reduced biomass into PHA. By using PHA-reduced biomass as a source of carbon for the production of microorganisms in a microorganism fermentation system, a series of biochemical enzymatic pathways are generated in situ by the microorganism culture to carry out the metabolic utilization of PHA-reduced biomass for growth, reproduction, and PHA synthesis.

Without being limited by theory, it is believed that gas-utilizing microorganisms and biomass-utilizing microorganisms are able to co-exist as a single microorganism consortium because they utilize sources of carbon that require distinctly different bioenzymatic assimilation pathways. For instance, while methane metabolism requires the methane monooxygenase enzyme to catalyze the conversion of methane into methanol for cellular assimilation, and methane monooxygenase is competitively inhibited by a wide range of compounds, it is not inherently deactivated by high concentrations of cellular biomass, including PHA-reduced biomass. Similarly, the chlorophyll-based metabolic assimilation systems required for the conversion of carbon dioxide into biomass and PHA are not inherently deactivated or competitively inhibited by high concentrations of cellular biomass, including PHA-reduced biomass. Likewise, the enzymatic architecture enabling the metabolic utilization, breakdown, and/or assimilation of PHA-reduced biomass is not inherently deactivated or competitively inhibited by high concentrations of methane and/or carbon dioxide, particularly as the process requires neither methane monooxygenase nor chlorophyll. Without being limited by theory, Applicant believes that the relatively noncompetitive, and in some cases commensal or mutualistic relationships between microorganisms consuming a carbon-containing gas and a PHA-reduced biomass, make it possible to create a microorganism culture comprising biomass-utilizing microorganisms and gas-utilizing microorganisms, wherein both carbon-containing gases and PHA-reduced biomass may be metabolized as simultaneously assimilable sources of carbon.

In the case of autotrophic, methanotrophic, and/or biomass-utilizing microorganisms, Applicant has found that a mutualistic, positive-feedback loop relationship can be created in a single (or optionally multiple) reaction vessel. In such embodiments, the oxygen created by autotrophic metabolism is utilized by methanotrophic and/or biomass-utilizing microorganisms for metabolic functions, the carbon dioxide created by methanotrophic and/or biomass-utilizing microorganism metabolism is utilized for autotrophic metabolism, the methane and/or carbon dioxide created by anaerobic methanogenic microorganisms is utilized by methanotrophic microorganisms, and the biomass created by methanotrophic, autotrophic, and/or heterotrophic microorganisms is used to provide a source of carbon to methanogenic and/or other heterotrophic microorganisms. Due to the microscopic-level induction of oxygen and/or carbon dioxide created therein, mass transfer efficiencies in several embodiments are significantly improved over traditional gas induction means, such as gas sparging, mechanical mixing, static mixing, or other means known in the art. To applicant's knowledge, prior to the disclosure herein, the use of autotrophic microorganisms cultured in association with heterotrophic microorganisms has never been suggested as a means to improve mass transfer efficiencies, supply oxygen, and/or augment microorganism growth rates in a positive feedback loop system.

In several further embodiments of the invention, PHA-reduced biomass is used by heterotrophic microorganisms, including acidogenic, acetogenic, and methanogenic microorganisms, to produce methane, which is further utilized by methanotrophic microorganisms to produce biomass, including PHA. In some embodiments of the invention, anaerobic microorganisms coexist with aerobic microorganisms under microaerobic conditions (e.g., mean dissolved oxygen concentrations approximately 0.00-1.0 ppm, including about 0.001 to about 0.002 ppm, about 0.002 to about 0.03 ppm, about 0.03 to about 0.04 ppm, about 0.04 to about 0.5 ppm, about 0.5 to about 0.6 ppm, about 0.6 to about 0.7 ppm, about 0.7 to about 0.8 ppm, about 0.8 to about 0.9 ppm, about 0.9 to about 1.0 ppm, and overlapping ranges thereof.

In some embodiments of the invention, heterotrophic, methanotrophic, methanogenic, and/or autotrophic microorganisms are divided into multiple stages and vessels, in particular, anaerobic and aerobic stages, in order to carry out the conversion of PHA-reduced biomass into methane and PHA. In further embodiments of the invention, PHA-reduced biomass is returned to the culture using one or more vessels, whereby it is first converted to carbon dioxide, methane, and/or volatile organic compounds by a heterotrophic, e.g., methanogenic, microorganism consortium under anaerobic conditions and then converted to PHA by methanotrophic microorganisms under aerobic conditions, whereby carbon dioxide is also metabolized or otherwise used by autotrophic microorganisms, methanotrophic microorganisms, and heterotrophic microorganisms.

In several embodiments, light intensity is utilized to regulate the growth rate of heterotrophic and/or methanotrophic microorganisms. In some embodiments, light intensity is manipulated to regulate the generation of oxygen by autotrophic microorganisms. In some embodiments, the rate of oxygen generated by autotrophic microorganisms is subsequently used to control the growth and metabolism of heterotrophic and methanotrophic microorganisms.

In several embodiments, carbon dioxide is supplied to autotrophic microorganisms in the form of carbon dioxide created by methanotrophic and/or heterotrophic microorganisms. In some embodiments, each of these varieties of microorganism is cultured in a single vessel. In some embodiments, methane, sugar, biomass, and/or another non-carbon dioxide source of carbon is used to grow autotrophic microorganisms. To applicant's knowledge, autotrophic microorganisms have never been cultured using methane as a sole carbon input.

Some gas-utilizing microorganisms are unable to produce high concentrations of intracellular PHA. However, according to several embodiments, certain microorganism consortiums utilizing PHA-reduced biomass, or derivatives thereof, as a source of carbon are able to generate high intracellular PHA concentrations and thus effectively convert low PHA concentration biomass derived from a carbon-containing gas into a high PHA concentration biomass material under the conditions disclosed herein. In several embodiments, the concentration (by weight) of intracellular PHA is between about 10% to about 30%, about 30% to about 50%, about 50% to about 70%, about 70% to about 80%, about 80% to about 90%, about 90% or more, and overlapping ranges thereof. Thus, in one embodiment, the culture is contacted with the PHA-reduced biomass and then manipulated, according to the processes described herein, to effect PHA synthesis, wherein the PHA-reduced biomass is converted into PHA by biomass-utilizing microorganisms. In some embodiments, PHA synthesis is induced by nutrient limitation, nutrient excess, nutrient imbalance, or large shifts in nutrient concentration. In still further embodiments, PHA synthesis is induced by reducing the availability of nitrogen, oxygen, phosphorus, or magnesium to the culture. In some embodiments, these nutrients are simultaneously reduced (to varying or similar degrees). In some embodiments, the nutrients are reduced sequentially. In some embodiments, only one of the nutrients is reduced. For example, in certain embodiments, PHA synthesis is induced by reducing the availability of oxygen to the culture. In some embodiments, this is achieved by manipulating the flow rate of air or oxygen into the growth medium. In some embodiments, manipulation of the flow rate of other carbon-containing gases, such as methane and/or carbon dioxide, into the growth medium, or otherwise manipulating the rate of gas transfer in a system (e.g., by adjusting mixing rates or light injection rates) is employed. In one embodiment, oxygen limitation is induced by reducing the flow rate of oxygen into the growth medium. In another embodiment, oxygen limitation is induced by reducing the rate of light transmission into the medium to reduce the production of oxygen by autotrophic microorganisms. In some embodiments of the invention, the concentration of PHA generated in a biomass-utilizing microorganism culture utilizing PHA-reduced biomass as a source of carbon is at least 5%, at least 20%, or at least 50% by dry cell weight; in particularly preferred embodiments of the invention, the concentration of PHA in a biomass-utilizing microorganism is at least 80% by dry cell weight.

In some embodiments, a PHA-reduced biomass recycling system is utilized wherein substantially all (e.g., at least 50%, at least 60%, at least 70%, at least 80%, at least 90%, or at least 98%) of the PHA-reduced biomass produced is contacted with the culture until it is converted into PHA. In some such embodiments, solid sources of carbon are substantially output from the process or culture only in the form of isolated PHA.

In several embodiments, as carbon-containing gases are continually added to the medium to effect the production of biomass, the process disclosed above is repeated. Specifically, as the process continues, a portion of the PHA-containing biomass from the culture is removed from the medium, PHA is extracted from the PHA-containing biomass, PHA-reduced biomass is separated from isolated PHA, isolated PHA is recovered, purified, and dried, and PHA-reduced biomass is sent back to the culture and converted by the culture into PHA. In one embodiment, substantially all PHA-reduced biomass produced is contacted with the culture until it is converted into isolated PHA, and solid sources of carbon are substantially output from the process only in the form of isolated PHA. In other embodiments, carbon is substantially output from the system only in the form of PHA and methane, carbon dioxide, and/or volatile organic compounds.

The following example is provided to further illustrate certain embodiments within the scope of the invention. The example is not to be construed as a limitation of any embodiments, since numerous modifications and variations are possible without departing from the spirit and scope of the invention.

Example 1

A fermentation system comprising one or more vessels are partially filled with one or more liquid growth mediums, wherein the medium comprises methanotrophic, autotrophic, methanotrophic, and/or other heterotrophic or biomass-utilizing microorganisms containing PHA, and, per liter of water, 0.7-1.5 g $KH_2PO_4$, 0.7-1.5 g $K_2HPO_4$, 0.7-1.5 g $KNO_3$, 0.7-1.5 g NaCl, 0.1-0.3 g $MgSO_4$, 24-28 mg $CaCl_2*2H_2O$, 5.0-5.4 mg EDTA $Na_4(H_2O)_2$, 1.3-1.7 mg $FeCl_2*4H_2O$, 0.10-0.14 mg $CoCl_2*6H_2O$, 0.08-1.12 mg $MnCl_2*2H_2O$, 0.06-0.08 mg $ZnCl_2$, 0.05-0.07 mg $H_3BO_3$, 0.023-0.027 mg $NiCl_2*6H_2O$, 0.023-0.027 mg $NaMoO_4*2H_2O$, 0.011-0.019 mg $CuCl_2*2H_2O$. One or more of the mediums are anaerobic and/or aerobic, and carbon containing gases, including methane, carbon dioxide, and volatile organic compounds, as well as optionally air or oxygen, are fed into all or part of the system to induce the growth and reproduction of microorganisms through the utilization of carbon-containing gases, as well as the production of PHA.

Next, a portion of the media volume of the fermentation system is passed through a basket centrifuge to increase the solids content of the medium to approximately 167 g/L. The solids-containing centrate phase of the centrifuged solution is then transferred to a PHA extraction vessel, and the substantially solids-free filtrate phase of the centrifuged solution is recycled back to the fermentation system.

In some embodiments, the solids-containing centrate phase is optionally chemically pre-treated prior to extraction. In some embodiments, one or more of acids, bases, chloride, ozone, and hydrogen peroxide is added. In several embodiments, chemical pre-treatment increases the efficiency and yield of the subsequent extraction process. In some embodiments, the chemical pre-treatment functions to break down the cell well (partially or fully), thereby liberating a greater portion of the intracellular PHA. In some embodiments, chemical pre-treatment dissolves and/or removes impurities that negatively impact the PHA extraction process. In some embodiments, chemical pre-treatment enhances cell agglomeration, which increases the percentage of microorganisms that are extracted (e.g., cells in an agglomerated mass are not separated or lost in transfer steps). Next, following optional chemical pre-treatment, solvent is added into the PHA extraction vessel to create a solvent solution, and the solvent solution is then mixed for a period of time to cause the PHA in both the microorganisms to dissolve into the solvent, and thereby create PHA-rich solvent and PHA-reduced biomass. Over the course of a defined mixing period (e.g., 0.1-10 hours), the PHA content of the microorganisms is reduced by about 80% as it is dissolved into the solvent.

Next, the solvent solution comprising the PHA-rich solvent and PHA-reduced biomass is passed through a filter located at the bottom of the PHA extraction vessel, and the PHA-rich solvent is thereby separated from the PHA-reduced biomass. Water is then added to the PHA extraction vessel to create a water-biomass solution, and the water-biomass solution is then heated to 75° C. to cause any remaining solvent associated with the PHA-reduced biomass to exit the PHA extraction vessel as a gaseous vapor. The vapor discharged from the PHA extraction vessel is then passed through a heat exchanger and recovered as liquid solvent. Meanwhile, the PHA-rich solvent is transferred to a PHA purification vessel and mixed with room temperature water to create a water-solvent solution. The water-solvent solution is then heated to cause i) the solvent to exit the PHA extraction vessel as a gaseous vapor and ii) the isolated PHA to precipitate into the water and/or become a solid. The solvent vapor created by heating the water-solvent solution is then passed through a heat exchanger and converted into liquid solvent.

The isolated PHA is then substantially dewatered by filtration in a Nutsche filter, and the Nutsche filter containing the substantially dewatered isolated PHA is then heated to remove any additional volatile compounds, including trace water and/or solvent. Following heat drying in the Nutsche filter, the isolated PHA is recovered as substantially pure PHA (e.g., greater than about 90% PHA).

Concurrently, the water-biomass solution comprising PHA-reduced biomass and water is transferred from the PHA extraction vessel back into the fermentation system, where the PHA-reduced biomass is contacted with one or more of the microorganism cultures. Next, the medium of the fermentation system is manipulated to cause the one or more microorganisms within the system to metabolize the PHA-reduced biomass as a source of carbon and nutrients.

Depending on the embodiment, the culture conditions are adjusted to determine the point at which the inception of the growth or PHA metabolism phase occurs. As discussed herein, manipulation of the concentration of one or more growth culture media nutrients can alter the metabolic pathways favored by certain microorganisms. Additionally, the use of PHA-reduced biomass-derived carbon for the production of additional biomass versus the production of PHA can be tailored based on whether the intent is to grow the culture (e.g., increase the overall biomass) or to harvest PHA (e.g., shift the culture from growth phase to production of PHA). As such, the reduction, increase, or adjustment of the concentration certain growth nutrients, and the timing of such adjustment, plays a role in the metabolic state and PHA production of the culture. Adjustment of growth nutrients can occur at any point after the PHA-reduced biomass is returned to the microorganism system. In some embodiments, adjustment is immediate (e.g., within minutes to a few hours). In some embodiments, a longer period of time elapses. In some embodiments, adjustment in one or more growth nutrients occurs after about 2 to 4 hours, after about 4 to 6 hours, after about 6 to 8 hours, after about 8 to 10 hours, after about 10 to 12 hours, after about 12 to 14 hours, after about 14 to 18 hours, after about 18 to 24 hours, and overlapping ranges thereof. In still additional embodiments, adjustment in one or more growth nutrients occurs after about 2 to about 5 days, about 5 to about 10 days, about 10 to about 15 days, about 15 to about 20 days, about 20 to about 30 days, about 30 to about 50 days, and overlapping ranges thereof. In some embodiments, longer times elapse prior to adjusting one or more growth nutrients to induce PHA polymerization.

After a desired period of time has elapsed, the dissolved oxygen and/or nitrogen concentration (or concentration of another nutrient) of one or more parts of the medium is reduced or adjusted to cause one or more of the microorganisms within the system to utilize the PHA-reduced biomass in the medium as a source of carbon for the synthesis of PHA. In some embodiments, the percent adjustment ranges from about 20% to about 100%, including about 20% to about 30%, about 30% to about 40%, about 40% to about 50%, about 50% to about 60%, about 60% to about 70%, about 70% to about 80%, about 80% to about 90%, about 90% to about 100%, and overlapping ranges thereof. In several embodiments, depending on the characteristics of a culture in a given embodiment, a specific percentage reduction, increase, or adjustment in nutrient may not be necessary, but a reduction, increase, or adjustment is used that is sufficient to convert certain cells from a relative growth phase to a relative PHA synthesis phase. After approximately 12-24 hours of PHA synthesis, substantially all of the PHA-reduced biomass within the growth medium has been metabolized into biomass-utilizing microorganism biomass, including PHA. In certain embodiments, greater or lesser PHA synthesis times result in varying percentages of the PHA-reduced biomass within the growth medium being metabolized into biomass, including PHA.

As carbon containing gases are continually added to the fermentation system to effect the production of biomass, the process is repeated, wherein solid sources of carbon substantially exit the system only in the form of PHA. Specifically, as the process continues, a portion of the PHA-containing biomass from the fermentation vessel is passed through a dewatering centrifuge to increase the solids content of the PHA-containing biomass, PHA is extracted from the removed PHA-containing biomass using a solvent-based extraction system to create PHA-reduced biomass and isolated PHA, PHA-reduced biomass is separated from isolated PHA, isolated PHA is recovered, purified, and dried, and PHA-reduced biomass is sent back to the fermentation system and converted by microorganisms into PHA, such that substantially all PHA-reduced biomass produced is contacted with the culture until it is converted into isolated PHA, and wherein solid sources of carbon are substantially output from the process only in the form of isolated PHA.

While the above description of several compositions, systems, and methods contains many specificities, it should be understood that the embodiments of the present invention described above are illustrative only and are not intended to limit the scope of the invention. Numerous and various modifications can be made without departing from the spirit of the embodiments described herein. Accordingly, the scope of the invention should not be solely determined by the embodiments described herein, but also by the appended claims and their legal equivalents.

What is claimed is:

1. A method for generating a culture of methanotrophic microorganisms exhibiting enhanced polyhydroxyalkanoate (PHA) production via particulate methane monooxygenase (pMMO), the method comprising:
   (a) contacting a culture of methanotrophic microorganisms with a medium comprising copper and one or more additional nutrients and a carbon-containing gas that can be metabolized by said culture;
   (b) incubating said culture in said medium to cause growth of said culture; and
   (c) limiting the concentration of copper in said medium;
   (d) allowing or causing, for a first period of time, at least one of said one or more additional nutrient to decrease to a concentration to cause said methanotrophic microorganisms to generate PHA;
   (e) causing said PHA-producing microorganisms of step (d) to grow using pMMO by exposing, for a second period of time, said PHA-producing microorganisms to the culture medium of (a); and
   (f) subjecting said culture to at least one additional repetition of steps (a)-(e) resulting in a culture wherein PHA is generated by pMMO at a greater rate as compared to soluble methane monooxygenase (sMMO).

2. The method of claim 1, wherein said culturing is performed under non-sterile conditions.

3. The method of claim 1, wherein said culture of methanotrophic microorganisms is capable of producing intracellular PHA concentrations of at least 71% of total dry cell weight of said methanotrophic microorganisms.

4. The method of claim 1, wherein said copper concentration is limited to be between about 0.001 micromolar and about 1000 micromolar.

5. The method of claim 1, wherein said first period of time ranges from about 2 to 24 hours.

6. The method of claim 1, wherein said second period of time ranges from about 12 to 24 hours.

7. The method of claim 1, wherein said additional nutrient comprises at least one of the nutrients selected from the group consisting of aluminum, boron, calcium, carbon, carbon dioxide, cobalt, iron, magnesium, molybdenum, nitrogen, oxygen, phosphorus, potassium, sodium, and zinc.

8. The method of claim 1, wherein the culture of methanotrophic microorganisms with enhanced PHA production through pMMO is characterized by:
   (a) lack of the genetic material encoding soluble methane monooxygenase (sMMO), failure to transcribe DNA encoding sMMO or translate mRNA encoding sMMO, and/or failure to produce a functional sMMO enzyme;
   (b) having the genetic material encoding the ethylmalonyl-CoA pathway, transcribing DNA encoding the ethylmalonyl-CoA pathway, and translating mRNA encoding the ethylmalonyl-CoA pathway; or
   (c) the capability of producing polyhydroxyalkanoate (PHA) at intracellular PHA concentrations with a ratio of PHA to non-PHA biomass exceeding 3:1 on a dry weight basis.

9. The method of claim 1, wherein the culture of methanotrophic microorganisms with enhanced PHA production through pMMO is characterized by:
   (a) lack of the genetic material encoding soluble methane monooxygenase (sMMO), failure to transcribe DNA encoding sMMO or translate mRNA encoding sMMO, and/or failure to produce a functional sMMO enzyme;
   (b) having the genetic material encoding the ethylmalonyl-CoA pathway, transcribing DNA encoding the ethylmalonyl-CoA pathway, and translating mRNA encoding the ethylmalonyl-CoA pathway; and
   (c) the capability of producing polyhydroxyalkanoate (PHA) at intracellular PHA concentrations with a ratio of PHA to non-PHA biomass exceeding 3:1 on a dry weight basis.

10. The method of claim 1, wherein the culture of methanotrophic microorganisms comprises microorganisms from a genus selected from a group consisting of: *Methylosinus, Methylocystis, Methylococcus, Methylobacterium*, and *Pseudomonas*.

11. A method for generating a culture of methanotrophic microorganisms capable to polyhydroxyalkanoate (PHA) production at intracellular PHA concentrations with a ratio of PHA to non-PHA biomass exceeding 3:1 on a dry weight basis, the method comprising:
   (a) providing a culture of methanotrophic microorganisms capable of metabolizing a carbon-containing gas;

(b) providing a culture a medium comprising copper and one or more additional nutrient;
(c) providing a carbon-containing gas that can be metabolized by said culture;
(d) incubating the culture of methanotrophic microorganisms in the culture medium and in the presence of the carbon-containing gas to cause growth of said culture;
(e) limiting the concentration of copper in said medium;
(f) for a first period of time, allowing or causing at least one of said one or more additional nutrients to decrease to a concentration that results in the methanotrophic microorganisms generating PHA;
(g) causing said PHA-producing microorganisms of step (f) to grow using pMMO by exposing, for a second period of time, said PHA-producing microorganisms to the culture medium of (b) and the carbon-containing gas of (c) and incubating the culture as in step (d); and
(h) repeating steps (e)-(g) a plurality of times to result in a culture producing progressively less sMMO and progressively more pMMO, thereby yielding intracellular PHA concentrations with a ratio of PHA to non-PHA biomass exceeding 3:1 on a dry weight basis.

12. The method of claim 1, wherein the culture of methanotrophic microorganisms comprises microorganisms from a genus selected from a group consisting of: *Methylosinus*, *Methylocystis*, *Methylococcus*, *Methylobacterium*, and *Pseudomonas*.

13. The method of claim 11, wherein the limited copper concentration is between about 0.001 micromolar and about 1000 micromolar.

14. The method of claim 11, wherein the resulting culture of methanotrophic microorganisms lacks the genetic material encoding soluble methane monooxygenase (sMMO), fails to transcribe DNA encoding sMMO or translate mRNA encoding sMMO, and/or fails to produce a functional sMMO enzyme.

15. The method of claim 11, wherein the culture of methanotrophic microorganisms exhibits particulate methane monooxygenase activity in the presence of copper ion concentrations between 0.001 micromolar and 1000 micromolar.

16. The method of claim 11, wherein said methanotrophic microorganisms exhibit ethylmalonyl-CoA pathway activity in the presence of copper concentrations between 0.001 micromolar and 1000 micromolar.

17. The method of claim 11, wherein said one or more additional nutrient comprises at least one of the nutrients selected from the group consisting of aluminum, boron, calcium, carbon, carbon dioxide, cobalt, iron, magnesium, molybdenum, nitrogen, oxygen, phosphorus, potassium, sodium, and zinc.

18. The method of claim 11, wherein at least one of said one or more additional nutrient comprises dissolved oxygen and wherein the method further comprises increasing the concentration of dissolved oxygen in said culture media to preferentially select for methanotrophic microorganisms exhibiting reduced pigmentation.

19. The method of claim 1, wherein at least one of said one or more additional nutrient comprises dissolved oxygen and wherein the method further comprises increasing the concentration of dissolved oxygen in said culture media to preferentially select for methanotrophic microorganisms exhibiting reduced pigmentation.

20. A composition comprising isolated microorganisms obtained from the method of claim 1.

\* \* \* \* \*